(12) United States Patent
Anderson et al.

(10) Patent No.: US 8,728,458 B2
(45) Date of Patent: May 20, 2014

(54) COMBINATION ANTI-HIV VECTORS, TARGETING VECTORS, AND METHODS OF USE

(75) Inventors: Joseph Anderson, Davis, CA (US); Gerhard Bauer, Davis, CA (US); Jan A. Nolta, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/266,236

(22) PCT Filed: Apr. 29, 2010

(86) PCT No.: PCT/US2010/033042
§ 371 (c)(1),
(2), (4) Date: Dec. 2, 2011

(87) PCT Pub. No.: WO2010/127166
PCT Pub. Date: Nov. 4, 2010

(65) Prior Publication Data
US 2012/0076763 A1    Mar. 29, 2012

Related U.S. Application Data

(60) Provisional application No. 61/174,419, filed on Apr. 30, 2009.

(51) Int. Cl.
*A61K 48/00* (2006.01)

(52) U.S. Cl.
USPC .................. 424/93.21; 435/320.01; 435/325; 514/44

(58) Field of Classification Search
None
See application file for complete search history.

(56) References Cited

U.S. PATENT DOCUMENTS

| 2004/0248296 A1 | 12/2004 | Beresford et al. |
| 2007/0141679 A1 | 6/2007 | Sodroski et al. |
| 2008/0003682 A1 | 1/2008 | Lois-Caballe et al. |
| 2008/0227736 A1 | 9/2008 | Chen et al. |

FOREIGN PATENT DOCUMENTS

| WO | WO-2004/094642 A2 | 11/2004 |
| WO | WO-2005/081911 A2 | 9/2005 |
| WO | WO 2007/000668 A2 | 1/2007 |
| WO | WO-2008/109837 A2 | 9/2008 |
| WO | WO-2008/150814 A2 | 12/2008 |

OTHER PUBLICATIONS

Cronin et al. (Curr Gene Therapy 2005: 387-398).*
An et al., "Stable reduction of CCR5 by RNAi through hematopoietic stem cell transplant in non-human primates," Proc. Natl. Acad. Sci. 104(32):13110-13115 (2007).
Anderson et al., "Complete knockdown of CCR5 by lentiviral vector-expressed siRNAs and protection of transgenic macrophages against HIV-1 infection", Gene Therapy 14:1287-1297 (2007).
Anderson et al., "Human immunodeficiency virus type 1 restriction by human-rhesus chimeric tripartite motif 5α (TRIM 5α) in CD34+ cell-derived macrophages in vitro and in T cells in vivo in severe combined immunodeficient (SCID-hu) mice transplanted with human fetal tissue," Hum Gene Ther 19:217-228 (2008).
Anderson et al., "Preintegration HIV-1 inhibition by a combination lentiviral vector containing a chimeric TRIM5α protein, a CCR5 shRNA, and a TAR decoy," Molecular Therapy 17(12):2103-2114 (2009).
Anderson et al., "Safety and efficacy of a lentiviral vector containing three anti-HIV genes-CCR5 ribozyme, tat-rev siRNA, and TAR decoy-in SCID-hu mouse-derived T cells," Mol. Ther. 15:1182-1188 (2007).
Bai et al., "Characterization of anti-CCR5 ribozyme-transduced CD34 hematopoietic progenitor cells in vitro and in a SCID-hu mouse model in vivo," Mol. Ther. 1(3):244-254 (2002).
Bauer et al., "Gene therapy for pediatric AIDS," Ann. NY Acad. Sci. 918:318-329 (2000).
Bonyhadi et al., "RevM10-expressing T cells derived in vivo from transduced human hematopoietic stem-progenitor cells inhibit human immunodeficiency virus replication," J Virol; 71(6):4707-4716 (1997).
Castanotto et al., "Functional siRNA expression from transfected PCR products," RNA 8:1454-1460 (2002).
Cordelier et al., "Targeting CCR5 with siRNAs: using recombinant SV40-derived vectors to protect macrophages and microglia from R5-tropic HIV," Oligonucleotides 13:281-294 (2003).
Ding et al., "A combination anti-HIV-1 gene therapy approach using a single transcription unit that expresses antisense, decoy, and sense RNAs, and *trans*-dominant negative mutant GAG and ENV proteins," Front. Biosci. 7:a15-28 (2002).
Fire et al., "Potent and specific genetic interference by double-stranded RNA in *Caenorhabditis elegans*," Nature 391:806-811 (1998).
Huang et al., "The role of a mutant CCR5 allele in HIV-1 transmission and disease progression," Nat. Med. 2(11):1240-1243 (1996).

(Continued)

*Primary Examiner* — Kimberly Chong
(74) *Attorney, Agent, or Firm* — Foley & Lardner LLP; Antoinette F. Konski

(57) ABSTRACT

Recombinant lentiviral vectors containing at least: a lentiviral backbone comprising essential lentiviral sequences for integration into a target cell genome; a nucleic acid encoding a CCR5 RNAi; and an expression control element that regulates expression of the nucleic acid encoding the CCR5 RNAi element, are provided by this invention. In an alternative aspect, the vector also contains polynucleotides encoding TRIM5 alpha and HIV TAR decoy sequences along with gene expression regulation elements such as promoters operatively linked to the polynucleotides. The vectors are combined with packaging plasmid and envelope plasmids and optionally conjugated to cell-specific targeting antibodies. Diagnostic and therapeutic methods for using the compositions are further provided herein.

48 Claims, 17 Drawing Sheets

(56) References Cited

OTHER PUBLICATIONS

Humeau et al., "Efficient lentiviral vector-mediated control of HIV-1 replication in CD4 lymphocytes from diverse HIV+ infected patients grouped according to CD4 count and viral load," Mol. Ther. 9(6):902-13 (2004).

Hütter et al., "Long-term control of HIV by CCR5 Delta32/Delta32 stem-cell transplantation," N. Engl. J. Med. 360:692-698 (2009).

Iijima et al., "Cell-specific targeting of a thymidine kinase/ gancyclovir gene therapy system using a recombinant Sindbis virus vector," Int. J. Cancer. 80:110-118 (1999).

Kohn et al., "A clinical trial of retroviral-mediated transfer of a *rev*-responsive element decoy gene into CD34+ cells from the bone marrow of human immunodeficiency virus-1-infected children," Blood 94(1):368-371 (1999).

Kumar et al., "T cell-specific siRNA delivery suppresses HIV-1 infection in humanized mice," Cell 134:577-586 (2008).

Lee et al., "Expression of small interfering RNAs targeted against HIV-1 rev transcripts in human cells," Nat. Biotechnol. 20:500-505 (2002).

Liang et al., "Targeted transduction of CD34+ hematopoietic progenitor cells in nonpurified human mobilized peripheral blood mononuclear cells," J. Gene Med. 11:185-196 (2009).

Liu et al., "Homozygous defect in HIV-1 coreceptor accounts for resistance of some multiply exposed individuals to HIV-1 infection," Cell 86:367-377 (1996).

Marks et al., "New antiretroviral agents for the treatment of HIV infection," Curr. HIV/AIDS Rep. 1:82-88 (2004).

Martínez et al., "Suppression of chemokine receptor expression by RNA interference allows for inhibition of HIV-1 replication," AIDS 16(18):2385-2390 (2002).

Michienzi et al., "A nucleolar TAR decoy inhibitor of HIV-1 replication," Proc. Natl. Acad. Sci. 99(22):14047-14052 (2002).

Mitsuyasu et al., "Phase 2 gene therapy trial of an anti-HIV ribozyme in autologous CD34+ cells," Nat. Med. 15(3):285-292 (2009).

Morizono et al., "Antibody-directed targeting of retroviral vectors via cell surface antigens," J. Virol. 75(17):8016-8020 (2001).

Morizono et al., "Lentiviral vector retargeting to P-glycoprotein on metastatic melanoma through intravenous injection," Nat. Med. 11(3):346-352 (2005).

Morizono et al., "Targeted gene delivery by intravenous injection of retroviral vectors," Cell Cycle 4(7):854-856 (2005).

Naif et al., "A human immunodeficiency virus type 1 isolate from an infected person homozygous for CCR5Δ32 exhibits dual tropism by infecting macrophages and MT2 cells via CXCR4," J. Virol. 76(7):3114-3124 (2002).

Novina et al., "siRNA-directed inhibition of HIV-1 infection," Nat. Med. 8(7):681-686 (2002).

Ohno et al., "Cell-specific targeting of Sindbis virus vectors displaying IgG-binding domains of protein A," Nat. Biotechnol. 15:763-767 (1997).

Rossi, "RNAi as a treatment for HIV-1 infection", Biotechniques 40:S25-S29 (2006).

Rossi, "The application of ribozymes to HIV infection," Curr. Opin. Mol. Ther. 1(3):316-322 (1999).

Sawyer et al., "Positive selection of primate *TRIM5α* identifies a critical species-specific retroviral restriction domain," Proc Natl Acad Sci 102(8): 2832-2837 (2005).

Stremlau et al., "The cytoplasmic body component TRIM5α restricts HIV-1 infection in Old World monkeys," Nature 427:848-853 (2004).

ter Brake et al., "Evaluation of safety and efficacy of RNAi against HIV-1 in the human immune system (Rag-2$^{-/-}$y$_c^{-/-}$) mouse model," Gene Ther. 16:148-153 (2009).

\* cited by examiner

COMBINATION ANTI-HIV VECTORS, TARGETING VECTORS, AND METHODS OF USE

CROSS-REFERENCE TO RELATED APPLICATIONS

The present application is a national stage application under 35 U.S.C. §371 of International Application Serial No, PCT/US2010/033042, filed Apr. 29, 2010, which claims priority under 35 U.S.C. §119(e) to U.S. Provisional Application Ser. No. 61/174,419, filed Apr. 30, 2009, the disclosures of which are hereby incorporated by reference in their entireties for all purposes.

BACKGROUND

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

HIV infection continues to spread worldwide in both developed and underdeveloped countries with no effective vaccine available. Current antiretroviral drug therapies have been successful in suppressing viral infection as long as the patient is compliant with the prescribed regimen. However, with prolonged use, these treatments can become toxic and drug resistant viral escape mutants arise [1-5]. New and innovative therapies need to be developed that overcome the limitations of current small drug antiretrovirals. Gene therapy offers a promising alternative or supplement to current treatments due to advantages which include the possibility of a one-time treatment, controlled or constitutive anti-HIV gene expression, and long-term viral inhibition particularly if hematopoietic progenitor cells (HPCs) are targeted. Many anti-HIV genes have been evaluated for their efficacy in inhibiting viral infection including antisense RNAs, riboyzymes, RNA decoys, siRNAs, intrabodies, transdominant proteins, and restriction factors [8-23, 42-43]. These molecules have been targeted to both viral genes and proteins and also cellular genes critical for viral infection and replication. Several groups, including ours, have been involved with human clinical trials using a select number of these anti-HIV genes transferred into HPCs by retroviral and lentiviral vectors [19-23]. However, improvements in stem cell transduction efficiency and in the effectiveness of the vector to interfere with different stages of the HIV life cycle are still needed.

However, none of these prior art approaches have effectively eliminated HIV entry and replication in vivo. This invention satisfies this need and provides related advantages as well.

SUMMARY OF THE INVENTION

HIV-1 gene therapy offers a promising alternative to small molecule antiretroviral treatments and current vaccination strategies by transferring, into HIV-1 susceptible cells, the genetic ability to resist infection. The need for novel and innovative strategies to prevent and treat HIV-1 infection is critical due to devastating effects of the virus in developing countries, high cost, toxicity, and generation of escape mutants from antiretroviral therapies and the failure of past and current vaccination efforts. To that end, applicants provide an HIV-1 susceptible cell-specific targeting vector to selectively transfer, into CCR5 positive target cells, an anti-HIV CCR5-shRNA gene for subsequent knockdown of CCR5 expression and protection from HIV-1 infection. Using a ZZ-domain/monoclonal antibody conjugated Sindbis virus glycoprotein pseudotyped lentiviral vector, applicants demonstrated the utility of this strategy for HIV-1 gene therapy by specifically targeting HIV-1 susceptible cells and engineering these cells to resist HIV-1 infection. CCR5 positive human cells were successfully and specifically targeted and in vivo for transduction by a lentiviral vector expressing a highly potent CCR5 shRNA which conferred resistance to HIV-1 infection.

This invention provides a lentiviral vector comprising, or alternatively consisting essentially of, or yet further consisting of: a lentiviral backbone comprising essential lentiviral sequences for integration into a target cell genome; a nucleic acid encoding a CCR5 RNAi that, in one aspect, inhibits integration of a human immunodeficiency virus (HIV) into a mammalian cell; and an expression control element that regulates expression of the nucleic acid encoding the CCR5 RNAi element. In a further aspect, the lentiviral vector also contains a nucleic acid encoding a TRIM5alpha sequence and an HIV TAR decoy sequence.

The invention also provides a lentiviral vector as described above and a packaging plasmid which contains the nucleoside, capsid and matrix proteins. In a further aspect, the invention further comprise an envelope plasmid and in a further aspect, a packaging cell line is provided.

Also provided are pseudotyped lentiviral particles that are optionally conjugated to cell-specific targeting antibodies. The particles optionally can be conjugated to cells.

The vectors and particles are useful to inhibit, ex vivo and in vivo, the replication of HIV in a cell system, such as a cell culture, or in a subject in need thereof by administering an effective amount of the vector, the particle or the cell conjugated to the particle. In one aspect, the methods not only inhibit HIV replication but also prevent replication in a subject infected with the virus. Specific details of the various embodiments of this invention are provided herein.

BRIEF DESCRIPTION OF SELECTED SEQUENCE LISTINGS

Figure 1:
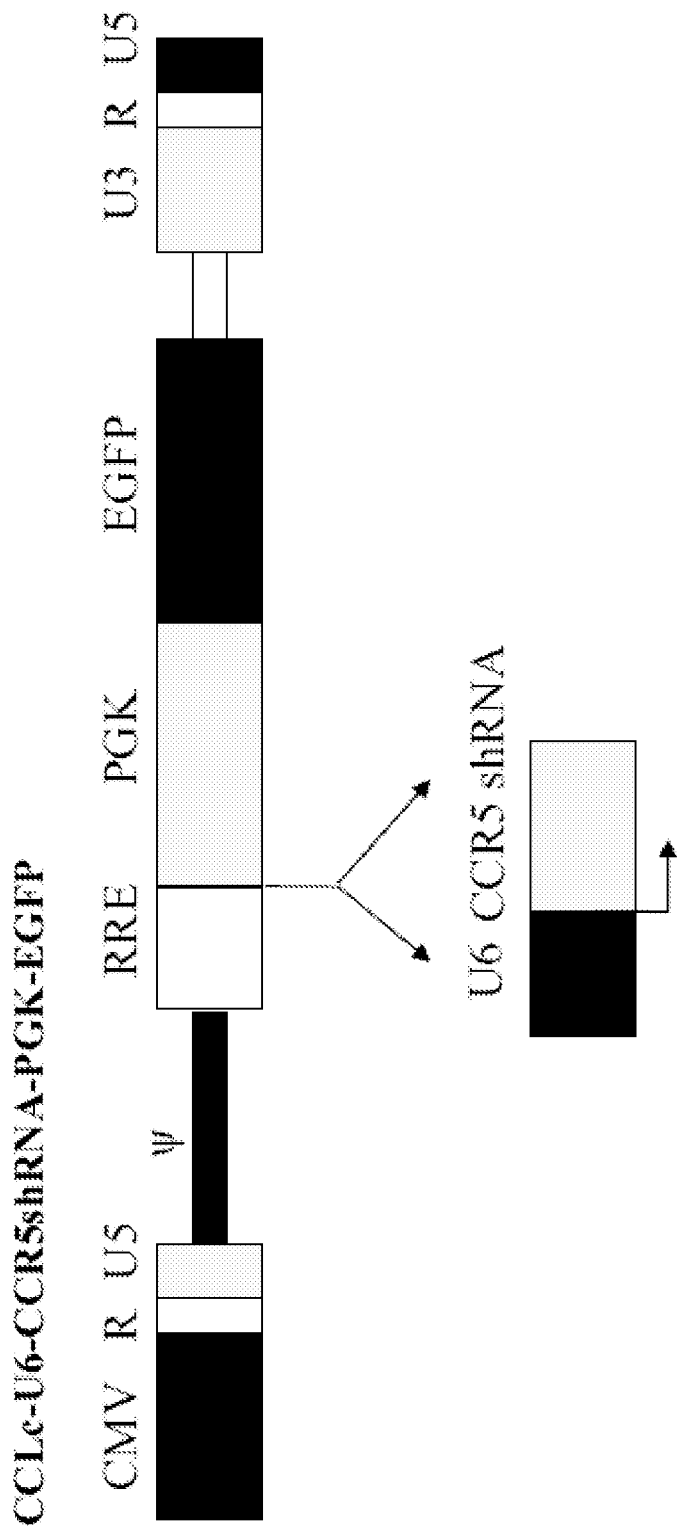
FIG. 1 shows a CCR5 shRNA lentiviral vector: A third generation lentiviral vector, CCLc-x-PGK-EGFP, containing an EGFP reporter gene was used to generate the CCR5 shRNA construct. The CCR5 shRNA was expressed under the control of the human polymerase-III U6 small RNA promoter and was inserted upstream of the EGFP reporter gene.

SEQ ID NO: 11 is the nucleotide sequence of the CCR5 expression cassette. Nucleotides 1-283 corresponds to the polymerase-III U6 promoter followed by the CCR5 shRNA sequence (nucleotides 284-330) which is followed by a string of 6 thymidines (nucleotides 331-336) which is the "transcriptional stop signal" for the U6 promoter. Alternative CCR5 RNAi for use in this invention are also shown in SEQ ID NOS: 12-15, as well as a full length coding sequence for Human G-Protein Chemokine Receptor (CCR5), SEQ ID NO: 16 that is reproduced from GenBank Accession No. DM068065, last accessed on Apr. 29, 2009.

SEQ ID NO: 17 is a polynucleotide encoding a human/rhesus macaque chimeric TRIM5alpha sequence. The first six nucleotides are the Kozak sequence followed by the ATG start codon. The nucleotides corresponding to the rhesus macaque 13 amino acids inserted into the human TRIM5alpha sequence to make the chimeric protein (994-1032). The last 39 nucleotides at the end of the sequence (1492-1530) correspond to a hemmaglutinin tag which was put on the end of the protein coding sequence for detection of expression. These 39 nucleotides are followed by the TGA stop codon. The chimeric TRIM5alpha protein was inserted just downstream from the MNDU3 polymerase-II promoter in the CCLc-MNDU3-x-PGK-EGFP lentiviral vector. Additional Polymerase-II promoters for use in this invention include a) EF1-alpha; b) PGK (phosphoglycerate kinase promoter); c) CMV (minimal cytomegalovirus promoter); and d) LTRs from lentiviral and lentiviral vectors.

SEQ ID NO: 18 is the sequence of a lentiviral backbone of this invention. The HIV genes were inserted into the EcoRI site (e.g. at nucleotides 5208-5213). SEQ ID NO: 25 is a portion of the lentiviral backbone sequence of SEQ ID NO: 18, without certain promoter and reporter sequences from SEQ ID NO: 18.

SEQ ID NO: 19 is an HIV TAR decoy sequence for use in the embodiments of this invention. The polymerase-III U6 promoter is shown as nucleotides 1-283 followed by the TAR decoy sequence (284-415). The TAR decoy sequence is followed by a string of 6 thymidines which is the "transcriptional stop signal" for the U6 promoter. Additional TAR sequences for use in this invention include: a) 5'-cgacttaaaatcgctagcca-gatctgagcctgggagctctctggctag-3' (SEQ ID NO: 1) or b) 5'-gggtctctctggttagacca-gatttgagcctgggagctctctggctaactagggaaccc-3' (SEQ ID NO: 2) or c) 5'-acgaagcttgatcccgtttgccggtcgatcgcttcga-3' (SEQ ID NO: 3).

SEQ ID NO: 20 is the sequence of a packaging plasmid sequence for use in this invention.

SEQ ID NO: 26 is an embodiment of polynucleotides encoding the pSINDBIS-ZZ envelope plasmid and transcribed by the polymerase-II CMV promoter into one messenger RNA. The pSINDBIS-ZZ plasmid comprises the E3 gene (SEQ ID NO: 21), the E2 gene (SEQ ID NO: 22) (the ZZ domain is between nucleotides 220 and 597), the 6K gene (SEQ ID NO: 23) and the E1 gene (SEQ ID NO: 24).

MODES FOR CARRYING OUT THE INVENTION

Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Sohail (ed.) (2004) Gene Silencing by RNA Interference: Technology and Application (CRC Press).

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

An equivalent nucleic acid, polynucleotide or oligonucleotide is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, or oligonucleotide.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

A "gene" refers to a polynucleotide containing at least one open reading frame (ORF) that is capable of encoding a particular polypeptide or protein after being transcribed and translated.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell. In one aspect, this invention provides promoters operatively linked to the downstream sequences, e.g., HIV TAR, CCR5, siRNA and TRIM5alpha.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "probe" when used in the context of polynucleotide manipulation refers to an oligonucleotide that is provided as a reagent to detect a target potentially present in a sample of interest by hybridizing with the target. Usually, a probe will comprise a detectable label or a means by which a label can be attached, either before or subsequent to the hybridization reaction. Alternatively, a "probe" can be a biological compound such as a polypeptide, antibody, or fragments thereof that is capable of binding to the target potentially present in a sample of interest.

"Detectable labels" or "markers" include, but are not limited to radioisotopes, fluorochromes, chemiluminescent compounds, dyes, and proteins, including enzymes. Detectable labels can also be attached to a polynucleotide, polypeptide, antibody or composition described herein.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

The lentiviral vectors of this invention are based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the invention may be based on a genetically or otherwise (e.g. by specific choice of packaging cell system) altered version of a particular retrovirus.

That the vector particle according to the invention is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell; in this case, a stem cell.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. It also includes in some aspects, antibody variants, polyclonal antibodies, human antibodies, humanized antibodies, chimeric antibodies, antibody derivatives, a bispecific molecule, a multispecific molecule, a heterospecific molecule, heteroantibodies and human monoclonal antibodies.

Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "bispecific molecule" is intended to include any agent, e.g., a protein, peptide, or protein or peptide complex, which has two different binding specificities. The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"RNA interference" (RNAi) refers to sequence-specific or gene specific suppression of gene expression (protein synthesis) that is mediated by short interfering RNA (siRNA).

"Short interfering RNA" (siRNA) refers to double-stranded RNA molecules (dsRNA), generally, from about 10 to about 30 nucleotides in length that are capable of mediating RNA interference (RNAi), or 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, or 29 nucleotides in length. As used herein, the term siRNA includes short hairpin RNAs (shRNAs).

"Double stranded RNA" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides in length. For example, the stem can be 10-30 nucleotides in length, or alternatively, 12-28 nucleotides in length, or alternatively, 15-25 nucleotides in length, or alternatively, 19-23 nucleotides in length, or alternatively, 21-23 nucleotides in length.

Tools to assist siRNA design are readily available to the public. For example, a computer-based siRNA design tool is available on the internet at www.dharmacon.com, Ambion-www.ambion.com/jp/techlib/misc/siRNA_finder.html; Thermo Scientific-Dharmacon-www.dharmacon.com/DesignCenter/DesignCenterPage.aspx; Bioinformatics Research Center-sysbio.kribb.re.kr:8080/AsiDesigner/menuDesigner.jsf; and Invitrogen-rnaidesigner.invitrogen.com/rnaiexpress/.

Without being bound by theory, it is generally believed that the primary cellular receptor for HIV entry is the CD4 receptor. In addition to CD4 expression, CXCR4, and CCR5 are necessary co-factors that allow HIV entry when co-expressed with CD4 on a cell surface.

CXCR4, or fusin, is expressed on T cells (Feng et al. (1996) Science 10:272(5263):872-7. Co-expression of CXCR4 and CD4 on a cell allow T-tropic HIV isolates to fuse with and infect the cell. HIV gp120 interacts with both CD4 and CXCR4 to adhere to the cell and to effect conformational changes in the gp120/gp41 complex that allow membrane fusion by gp41.

CCR5 is another co-receptor that is expressed on macrophages and on some populations of T cells, can also function in concert with CD4 to allow HIV membrane fusion (Deng et al. (1996) Nature, June 20; 381(6584):661-6.

TRIM5alpha is 493 amino acid protein that is found in most primate cells that appears to act to interfere with the replication of retrovirus in infected cells. Human protein sequence is published in GenBank (Accession number NP_149023) and the mRNA sequence also has been published (NM_033034). Murine protein sequence is available at NP_783608 and mRNA is available at NM_175677. (All last accessed Apr. 29, 2009).

An "shRNA CCR5" is an interfering RNA that down regulates or suppresses expression of the CCR5 polynucleotide, examples of which are shown in SEQ ID NO: 11. CCR5 is also known as Human G-protein Chemokine Receptor HDGNR10. Isolated polynucleotides encoding this protein are known in the art and described, for example in U.S. Pat. No. 7,501,123.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present invention is also useful for veterinary treatment of companion mammals, exotic animals and domesticated animals, including mammals, rodents, and the like which is susceptible to RNA and in particular, HIV viral infection. In one embodiment, the mammals include horses, dogs, and cats. In another embodiment of the present invention, the human is an adolescent or infant under the age of eighteen years of age.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "disease," "disorder," and "condition" are used inclusively and refer to any condition mediated at least in part by infection by an RNA virus such as HIV.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to infection or a disease incident to infection. A patient may also be referred to being "at risk of suffering" from a disease because of active or latent infection. This patient has not yet developed characteristic disease pathology.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo.

The term administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

Descriptive Embodiments

Lentiviral Vectors

This invention provides a lentiviral vector comprising, or alternatively consisting essentially of, or yet further consisting of: a lentiviral backbone. In one aspect, the backbone contains essential lentiviral sequences for integration into a target cell genome. The vector also comprises, or alternatively consists essentially of, or yet further consists of a nucleic acid encoding a CCR5 RNAi and an expression control element that regulates expression of the nucleic acid encoding the CCR5 RNAi element.

In one aspect, the term "lentiviral vector" intends a recombinant vector that retains the ability to infect and transduce non-dividing and/or slowly-dividing cells and integrate into the target cell's genome. In several aspects, the lentiviral vector is derived from or based on a wild-type lentivirus. Examples of such, include without limitation, human immunodeficiency virus (HIV), equine infectious anaemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the invention need not be confined to the components of a particular virus. The viral vector may comprise components derived from two or more different viruses, and may also comprise synthetic components. Vector components can be manipulated to obtain desired characteristics, such as target cell specificity.

The recombinant lentiviral vectors of this invention are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of lentiviral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the lentiviral vector particles may be introduced into the host cell by transient transfection, or they may be integrated into the host cell genome, or they may be provided in a mixture of ways. The techniques involved are known to those skilled in the art.

In one aspect, the lentiviral backbone comprises, or alternatively consists essentially of, or yet further consists of, the backbone sequence of SEQ ID NO: 18 or an equivalent thereof. Alternative retroviral vectors for use in this invention include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

The lentiviral vector also comprises, or alternatively consists essentially of, or yet further consists of, a nucleic acid encoding a CCR5 RNAi. The RNAi may be any one or more of RNA interfering molecules as described herein, e.g., shRNA, siRNA, miRNA or dsRNA. In one particular aspect, the RNAi is one or more of a shRNA or siRNA sequence shown in SEQ ID NO: 11 or a polynucleotide having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity. Alternate sequences for use in this invention are available using the publicly available CCR5 polynucleotide sequence (see U.S. Pat. No. 7,501,123 or that disclosed in SEQ ID NOS: 11-15) and a computer-based siRNA design tool available on the internet at one or more of www.dharmacon.com, Ambion-www.ambion.com/jp/techlib/misc/siRNA_finder.html; Thermo Scientific-Dharmacon-www.dharmacon.com/DesignCenter/DesignCenterPage.aspx; Bioinformatics Research Center-sysbio.kribb.re.kr:8080/AsiDesigner/menuDesigner.jsf; and Invitrogen-rnaidesigner.invitrogen.com/rnaiexpress/.

To produce RNAi for use in this invention, one can follow conventional techniques as described in the art using published sequences or that provided by the applications. dsRNA and siRNA can be synthesized chemically or enzymatically in vitro using the methods disclosed in Micura, R. (2002) Agnes Chem. Int. Ed. Emgl. 41: 2265-9; Betz, N. (2003) Promega Notes 85:15-18; Paddison, P. J. and Hannon, G. J. (2002) Cancer Cell. 2:17-23. Chemical synthesis can be performed via manual or automated methods, both of which are well known in the art. Micura, R. (2002) Agnes Chem. Int. Ed. Emgl. 41: 2265-9. siRNA can also be endogenously expressed inside the cells in the form of shRNAs. Yu, J-Y. et al. (2002) Proc. Natl. Acad. Sci. USA 99: 6047-52; McManus, M. T. et al. (2002) RNA 8:842-50. Endogenous expression has been achieved using plasmid-based expression systems using small nuclear RNA promoters, such as RNA polymerase III U6 or H1, or RNA polymerase II U1. Brummelkamp, T. R. et al. (2002) Science 296:550-3; Novarino, G. et al. (2004) J. Neurosci. 24:5322-30.

In vitro enzymatic dsRNA and siRNA synthesis can be performed using an RNA polymerase mediated process to produce individual sense and antisense strands that are annealed in vitro prior to delivery into the cells of choice. Fire A. et al. (1998) Nature 391:806-811; Donze, O. and Picard, D. (2002) Nucl. Acids Res. 30 (10):e46; Yu, J-Y. et al. (2002) Proc. Natl. Acad. Sci. USA 99: 6047-52; Shim, E. Y. et al. (2002) J. Biol. Chem. 277:30413-6. Several manufacturers (Promega Corp. (Madison, Wis.); Ambion, Inc. (Austin, Tex.); New England Biolabs (Ipswich, Mass.); and Stragene (La Jolla, Calif.) provide transcription kits useful in performing the in vitro synthesis.

Alternatively, one can use a Polymerase-II promoter to express CCR5 miRNA. For this embodiment, microRNAs are initially transcribed from Pol-II promoters as long transcripts called primary-miRNAs which are processed into small pre-miRNAs. These pre-miRNAs are further processed intracellularly into miRNAs which are the mediators of gene regulation. CCR5 shRNAs or siRNAs can be converted to miRNAs by swapping in the exact CCR5 siRNA sequence in place of the original miRNA sequence. Hence, the CCR5 siRNA can be expressed via a Pol-II promoter in the context of a miRNA backbone for efficient processing and regulation/knockdown of gene expression. The original CCR5 siRNA sequence will be found within the entire miRNA sequence but will be surrounded by the original miRNA secondary structure generated from the extra nucleotides found in the miRNA backbone. Alternative Polymerase II promoters include, but are not limited to EF1-alpha; PGK (phosphoglycerate kinase promoter); CMV (minimal cytomegalovirus promoter) and LTRs from retroviral and lentiviral vectors.

In a further embodiment, the retroviral vector further comprise, or alternatively consists essentially of, or yet further consists of a nucleic acid encoding a TRIM5alpha polynucleotide and a sequence the regulates expression of the TRIM5alpha sequence operatively linked to it. For the purpose of illustration only, a nucleic acid that encodes TRIM5alpha for use in this invention is one that encodes either of the amino acid sequences for human TRIM5α 11-amino acid patch (GARGTRYQTFV (SEQ ID NO: 4)) or the rhesus macaque TRIM5α 13-amino acid patch (QAPGTLFTFPSLT (SEQ ID NO: 5)) or equivalents to these sequences. A TRIM5expression cassette having the TRIM5alpha sequence operatively linked to a polymerase-III promoter is provided in SEQ ID NO: 17. Alternative nucleic acids include, but are not limited to a polynucleotide having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the TRIM5alpha sequence shown in SEQ ID NO: 17 as long as the 11 amino acid (human) or the 13 amino acid sequence (rhesus macaque) remains.

In a yet further embodiment, the lentiviral vector further comprise, or alternatively consists essentially of, or yet further consists of a nucleic acid encoding an HIV TAR decoy polynucleotide. For the purpose of illustration only, a nucleic acid for use in this invention are provided in SEQ ID NO: 19 or an equivalent thereof, along with the sequence of a suitable regulation element such as polymerase-II promoter operatively linked to the sequence. Alternative nucleic acids include, but are not limited to a polynucleotide having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the TAR decoy sequence shown in SEQ ID NO: 19. Alternative sequences for use in this invention are disclosed in U.S. Patent Publication Nos. 2004/013167 and 2003/0013669 and U.S. Pat. Nos. 6,995,258; 5,994,108; and 5,693,508. HIV TAR mRNA sequences are also available on the GenBank database, available under Accession Nos. NM_134324 (*Homo sapiens* TAR (HIV-1) RNA binding protein 2, transcript variant 2) and NM_004178 ((*Homo sapiens* TAR (HIV-1) RNA binding protein 2, transcript variant 3), each last accessed on Apr. 29, 2009. These sequences are incorporated by reference into this application. Further additional sequences include: a) 5'-cgacttaaaatcgctagcca-gatctgagcctgggagctctctggctag-3' (SEQ ID NO: 1) or b) 5'-gggtctctctggttagacca-gatttgagcctgggagctctctggctaactagggaaccc-3' (SEQ ID NO: 2) or c) 5'-acgaagcttgatcccgtttgccggtcgatcgcttcga-3' (SEQ ID NO: 3).

In a further aspect, the lentiviral vector further comprises a marker or detectable label such as a gene encoding an enhanced green fluorescent protein (EGFP), red flouresence protein (RFP), green fluorescent protein (GFP) and yellow fluorescent protein (YFP) or the like. These are commercially available and described in the technical art.

Packaging Systems

The invention also provides a lentiviral vector as described above and a packaging plasmid which contains the nucleoside, capsid and matrix proteins. As an example, SEQ ID NO: 20 provides the sequence of a packaging plasmid that can be used in this invention. Alternatives include, but are not limited to a polynucleotide having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 20. Alternatives are also described in the patent literature, e.g., U.S. Pat. Nos. 7,262,049; 6,995,258; 7,252,991 and 5,710,037, incorporated herein by reference.

The system also contains a plasmid encoding a pseudotyped envelope protein provided by an envelope plasmid. Pseudotyped lentiviral vectors consist of vector particles bearing glycoproteins derived from other enveloped viruses or alternatively constaining functional portions. See, for example U.S. Pat. No. 7,262,049, incorporated herein by reference. In a preferred aspect, the envelope plasmid encodes an envelope protein that does not cause the viral particle to unspecifically bind to a cell or population of cells. The specificity of the viral particle is conferred by the antibody binding domain that is inserted into the particle. Examples of suitable envelope proteins include, but are not limited to those containing the *Staph. aureus* ZZ domain, the sequence of which is provided in SEQ ID NO: 26 or a polynucleotide having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to that shown in SEQ ID NO: 26. The choice of glycoprotein for use in the envelope is determined in part, by the antibody to which the particle may be conjugated.

This invention also provides the suitable packaging cell line. In one aspect, the packaging cell line is the HEK-293 cell line. Other suitable cell lines are known in the art, for example, described in the patent literature within U.S. Pat. Nos. 7,070,994; 6,995,919; 6,475,786; 6,372,502; 6,365,150 and 5,591,624, each incorporated herein by reference.

Pseudotyped Lentiviral Particles

This invention further provides a method for producing a pseudotyped lentiviral particle, comprising, or alternatively consisting essentially of, or yet further consisting of, transducing a packaging cell line with the lentiviral system as described above, under conditions suitable to package the lentiviral vector. Such conditions are known in the art and briefly described herein. The pseudotyped lentiviral particle can be isolated from the cell supernatant, using methods known to those of skill in the art, e.g., centrifugation. Such isolated particles are further provided by this invention.

This invention further provides the isolated pseudotyped lentiviral particle produced by this method. The pseudotyped lentiviral particle comprises, or alternatively consists essentially of, or yet further consists of a polynucleotide encoding a CCR5 RNAi and envelope protein comprising the pre-selected domain such as the ZZ *S. aureus* domain alone or in combination with a TRIM5alpha sequence and an HIV TAR decoy polynucleotide.

The isolated pseudotyped particles can be conjugate to one or more of an antibody or an antibody fragment (e.g. an fragment containing at least the Fc domain) that retains the ability to bind a pre-selected cell receptor selected from the group consisting of CCR5, CD4, CD34 and CXCR4. Such antibodies include anti-CCR5 antibody, an anti-CD4 antibody, an anti-CD34 antibody and a CXCR4 antibody. Anti-CCR5 antibodies are commercially available from Invitrogen; abcam; ProSci Inc. and eptitomics, and described in the patent literature within U.S. Pat. Nos. 7,122,185; 7,175,988; 7,160,546; and 6,930,174, each incorporated herein by reference. Anti-CD34 antibodies are commercially available from R&D Systems, Invitrogen; Biolegend; and Miltenyi Biotec, and described in the patent literature within U.S. Pat. No. 4,965,204, incorporated herein by reference. Anti-CD4 antibodies are commercially available from R&D Systems, Invitrogen; Biolegend; and Miltenyi Biotec, and described in the patent literature within U.S. Pat. No. 4,965,204, incorporated herein by reference. Anti-CXCR4 antibodies are commercially available from Leinco Technologies, Capralogics and BioLegend, and described in the patent literature within U.S. Pat. Nos. 7,521,045; 6,949,243 and 6,485,929, and U.S. Patent Publication No. 2005/0271665, each incorporated herein by reference.

The antibodies are not species specific. In other words, the antibodies can be polyclonal or monoclonal and can be murine, ovine, human or other species. In addition, they can be chimeric or humanized.

When used in combination, the particles can be combination of CD4/CCR5 or CD4/CXCR4 or CD4/CCR5/CXCR4 or CD4/CD34 or CD34/CCR5 or CD34/CXCR4 or CD4/CD34/CCR4/CXCR4, which target multiple populations of HIV susceptible cells.

Methods to Produce the Pseudotyped Particles

This invention also provides methods to prepare a pseudotyped lentiviral particle by transducing a packaging cell line, as described herein with the vector, the envelope plasmid and the packaging plasmid under conditions that facilitate packaging of the vector into the envelope particle. In one aspect, the pseudotyped lentiviral particle is a pseudotyped lentiviral particle. In a further aspect, the particles are separated from the cellular supernatant and conjugated to an antibody for cell-specific targeting.

In one aspect, the complete vector particle is a lentiviral, or alternatively a retroviral vector pseudotyped with a Sindbis virus glycoprotein envelope containing the ZZ domain of Protein A from *Staphylococcus aureus*.

The genetic information of the lentiviral vector particle is RNA which contains, on the 5' and 3' ends, the minimal LTR regions required for integration of the vector. In between the two LTR regions is the psi region which is required for packaging of the vector RNA into the particle. This region is followed by the RRE and cPPT sequences which enhance vector production by transporting the full length vector transcript out of the nucleus for efficient packaging into the vector particle. Next is the polymerase-II promoter MNDU3 which drives the expression of the chimeric TRIM5alpha gene. The polymerase-III U6 promoter driven CCR5 shRNA gene follows immediately downstream. Next is the polymerase-III U6 promoter driven TAR decoy gene. The last gene in the vector is an EGFP gene (enhanced Green Fluorescent Protein) which is driven by the polymerase-II PGK promoter. The EGFP gene is used as a reporter gene to detect transduced cells. The above listed genetic elements are transcribed into a full length RNA molecule which is packaged into the vector particle and contains all of the genetic information that will be integrated into the transduced cells.

The full length RNA transcript is packaged inside the capsid of the vector particle which contains the nucleocapsid, capsid, and matrix proteins which are generated from the packaging plasmid delta-8.91. The reverse transcriptase polymerse which is generated from the packaging plasmid delta-8.91 is also located within the capsid with the RNA transcript. The capsid encases and protects the full length RNA transcript.

Surrounding the capsid/RNA complex is the Sindbis-ZZ glycoprotein envelope which is generated from the Sindbis-ZZ plasmid. This envelope, when conjugated with a specific monoclonal antibody, will direct the vector particle to specifically transduce a cell of interest that expresses a cell surface receptor recognized by the chosen monoclonal antibody.

The vector particle is generated by a transient transfection protocol which includes a packaging cell line (HEK-293T cells), a lipofection reagent (Transit-293T), and the three plasmids encoding the parts of the vector particle (delta-8.91 (packaging plasmid), CCLc-MNDU3-TRIM5alpha-U6-CCR5shRNA-U6-TARdecoy (lentiviral vector plasmid), and Sindbis-ZZ (envelope plasmid).

HEK-293T cells are plated at 75% confluency in complete DMEM media 24 hours prior to transfection. After at least 24 hours post-plating of cells, the transfection mixture should be prepared. Three milliliters of serum free media is incubated with 150 ul of the lipofection reagent for 20 minutes at room temperature. The three plasmids are then added to the media/lipofection reagent mixture at a ratio of 5:5:2 (packaging plasmid: lentiviral vector plasmid: envelope plasmid) and incubated for 30 minutes. After this final incubation period, the media/lipofection reagent/DNA mixture is then added to the HEK-293T cells and left overnight for the transfection to occur. The next day, the transfection media is removed and fresh complete DMEM is added. Seventy-two hours later, the cell culture supernatant is collected and concentrated by ultracentrifugation at 20,000 rpm for 1.5 hours.

In one aspect, the 13-amino acid patch sequence required for the TRIM5alpha molecule to inhibit HIV infection is N terminal---QAPGTLFTFPSLT---C terminal. Thus, any TRIM5alpha polynucleotide must encode this primary amino acid sequence.

To construct the ZZ domain containing Sindbis virus glycoprotein, the ZZ domain from *S. aureus* was inserted in between the amino acids #71-#74 of the E2 region of the Sindbis glycoprotein gene. In the wild-type Sindbis glycoprotein E2 region, this is where normal cell surface receptor recognition occurs. By inserting the ZZ domain here, normal cell binding is abolished. After the ZZ domain was inserted into the E2 region in a BsteII restriction enzyme site, the entire E3-E2ZZ-6K-E1 glycoprotein gene was PCR amplified and TOPO cloned into the pcDNA3.1 expression plasmid. By inserting the glycoprotein genes into this expression plasmid, the genes are under the control of the highly active polymerase-II CMV promoter.

Once the vector particle buds from the packaging cells and is released into the supernatant, this vector particle is conjugated to an antibody as defined herein.

Isolated Host Cells

Yet further provided is an isolated cell or population of cells, comprising, or alternatively consisting essentially of, or yet further consisting of, a retroviral particle of this invention, which in one aspect, is a lentiviral particle. In one aspect, the isolated host cell is a packaging cell line.

In another aspect, the invention provides a pseudotyped lentiviral particle conjugated to an antibody as described herein which is further conjugated to a host cell expressing a receptor to which the lentiviral particle as described herein. In one aspect, the host cell is a cell expressing one or more of CD4, CD34, CXCR4 and/or CCR5. The cell can be any of a cell of a species of the group of: murine, rats, rabbit, simians, bovines, ovine, porcine, canines, feline, farm animals, sport animals, pets, equine, and primate, and in particular a human cell. Cells that are known to express such receptors include blood cell and in particular lymphocyte cells such as peripheral blood lymphocytes and mobilized blood lymphocytes. In another aspect, the host cell is an adult stem cell such as an hematopoietic stem cell "HSC" ($CD34^+$ and/or $CD34^+/Thy-1^-$ HSC)

Compositions, Screens and Therapeutic Uses

Also provided by this invention is a composition or kit comprising any one or more of the lentiviral vectors, packaging system, pseudotyped lentiviral, lentiviral particle conjugated to an antibody or fragment thereof which in turn may optionally be conjugated to a cell and a carrier. In one aspect, the carrier is a pharmaceutically acceptable carrier. These compositions can be used diagnostically or therapeutically as described herein and can be used in combination with other known anti-HIV therapies.

The compositions can be used in vitro to screen for small molecules and other agents that may modify HIV infectivity and replication by adding to the composition varying amounts of the agent to be tested and comparing it to a companion system that does not have the agent but which exhibits the desired therapeutic effect. For example, if it is known that the lentiviral particle inhibits HIV infection in a system, then the system can be used to test alternative therapies to determine if it is a substitute to the lentiviral particle. Alternatively, one can test agents in the lentiviral particle system itself to determine if the agent acts competitively, additively or synergistically with the lentiviral particle system. After an in vitro screen, the test agent or combination therapy can be assayed in an appropriate animal model.

When the particles and/or antibody conjugated cells (to the particles) are administered to an appropriate animal subject, the animal subject can be used as an animal model to test alternative therapies in the same manner as the in vitro screen. This invention also provides a method to inhibit HIV replication in vivo or ex vivo, comprising, or alternatively consisting essentially of, or yet further consisting of administering to a subject in need thereof an effective amount of the pseudotyped lentiviral particle or the pseudotyped lentiviral particle conjugated to the antibody as describe herein. In another aspect, a method to prevent HIV replication in vivo or ex vivo is provided comprising, or alternatively consisting essentially of, or yet further consisting of administering to a subject in need thereof an effective amount of the pseudotyped lentiviral particle or the pseudotyped lentiviral particle conjugated to the antibody as describe herein. The pseudotyped lentiviral particle or the pseudotyped lentiviral particle conjugated to the antibody as describe herein can be combined with other anti-lentiviral therapies that are known in the art. When combined with other therapies, administration of the therapies can be concurrent or sequential as determined by the treating physician. In one aspect, bone marrow, mobilized bone marrow cells or peripheral blood lymphocytes are removed from the patient to be treated and cultured with the pseudotyped lentiviral particle conjugated to the one or more antibodies. After an appropriate amount of time to allow for the particle to bind to the appropriate receptor, the cells are then re-administered to the subject or patient to which they were isolated. As noted above, this therapy can be combined with other anti-lentiviral therapies or the like.

This invention also provides a method to treat a subject at risk of developing an active infection or infected with HIV (AIDs) by administrering to the subject an effective amount of one of the compositions as described herein. For the purpose of this aspect, a subject is as described herein and therefore includes mammals, animals and humans, for example. Additional effective therapies can combined with this invention and/or added as necessary.

Further provided are methods to inhibit or prevent HIV replication in a cell infected with HIV, by contacting the cell with an effective amount of one or more of pseudotyped lentiviral vector particle as described herein or or the psuetotyped lentiviral vector as described herein. In one aspect, the contacting is in vitro. In another aspect it is in vivo.

This invention also provides the use of a compositions as described herein to prevent or treat an HIV infection and/or AIDs by administering to a subject an effective amount of one or more compositions described herein. Further provided is the use of a composition as described herein in the manufacture of a medicament to treat or prevent HIV infection and/or AIDs. Additional effective therapies can combined with this invention and/or added as necessary.

Having been generally described herein, the follow examples are provided to further illustrate this invention.

Experiment A—Specific Targeting of HIV Susceptible Cells

Background

More than 25 years after its discovery, the Human Immunodeficiency Virus (HIV) continues to be a major public health problem with more than 30 million people infected worldwide. Current small molecule antiretroviral therapies have been successful in suppressing viral replication and reducing morbidity and mortality from HIV, however, after prolonged use, toxicity can occur and viral escape mutants can arise from a continued low level of viral replication [1-5]. Vaccine strategies including live attenuated, whole inactivated virus, protein subunits, DNA vaccines, and viral expression vectors encoding HIV proteins have failed due to the broad diversity of HIV-1 strains and the ability of the virus to evade immune responses [6]. Gene therapy provides an alternative approach to current therapies and prophylactic strategies by offering the potential of long-term and constitutive protection from HIV infection and spread. Numerous anti-HIV RNA molecules have been developed and used to inhibit HIV infection and replication in gene therapy protocols including antisense RNAs, RNA decoys, ribozymes, and small interfering RNAs (siRNAs) [7-18]. Many of these anti-HIV genes have proven to be highly potent HIV inhibitors both in vitro and in vivo with a select few proceeding to clinical trials [19-23].

RNA-interference (RNAi) utilizes an innate cellular mechanism to silence gene expression by degradation of mRNA [24]. RNAi is highly effective in targeted gene knockdown for both gene discovery and the development of therapeutics by using 19-28 bp siRNAs to seek out homologous mRNA for destruction [25]. In numerous studies, this technology has been harnessed to inhibit HIV-1 infection by targeting viral genes [10, 17-18, 22]. Cellular genes necessary for HIV-1 attachment and fusion to target cells, such as the major receptor CD4 and the two main coreceptors CCR5 and CXCR4, have also been previously targeted by siRNAs [11, 13-17]. By blocking the attachment and fusion of HIV with the target cell membrane, viral entry and productive infection can be inhibited. Due to a naturally occurring 32-base pair deletion in the CCR5 gene, both homozygous and heterozygous individuals harboring this mutant allele are highly resistant to HIV-1 infection [26-28]. Individuals harboring this deletion are physiologically normal thus designating CCR5 as an excellent candidate for knockdown by siRNA for HIV gene therapy. Recently, long-term control of HIV-1 replication was observed in an infected individual who received a stem cell transplant for acute myeloid leukemia with donor stem cells from an individual homozygous for the CCR5 Δ32-bp mutant allele [29]. The results provided from this study demonstrated the importance of developing anti-HIV molecules to block the availability of CCR5, thus preventing HIV-1 infection.

Current gene therapy protocols rely on ex vivo transduction of hematopoietic stem cells or peripheral blood mononuclear cells (PBMCs) using retroviral or lentiviral vectors pseudotyped with amphotropic or pantropic envelopes. These procedures require either apheresis of PBMCs, mobilization of peripheral blood stem cells, or bone marrow aspirations. Clinical grade methods to isolate the target cells, tissue culture methods to introduce the vector, and finally re-administration of the gene modified cells into the patient are also required. The development of cell specific targeting vectors capable of selectively transducing cells of interest upon direct injection, in vivo, would greatly simplify and enhance HIV gene therapy applications by bringing them to areas where sophisticated laboratories and clinics are not available.

Several vector targeting approaches have focused on generating chimeric proteins with receptor ligands or single chain antibodies fused to membrane spanning molecules such as amphotropic retroviral glycoproteins and the influenza hemagglutinin protein [30-41]. Another novel method utilizes the ability of Sindbis virus glycoproteins to pseudotype lentiviral vectors. By modifying the Sindbis virus envelope through insertion of the ZZ-domain from the *Staphylococcus aureus* Protein A into the receptor binding region of the glycoprotein E2 gene, pseudotyped vectors acquired the ability to bind purified antibodies [42-43]. The ZZ-domain encodes an immunoglobulin binding domain allowing for a direct conjugation between the selected monoclonal antibody and the vector particle. These antibody-modified envelopes can then direct the lentiviral vectors to specific cells of interest for targeted transduction. These engineered vectors have been shown to transduce specific cell types such as CD34+ cord blood stem cells, metastatic melanoma cells, tumor cell lines, and cells expressing CD4 or the human leukocyte antigen (HLA) [48-53].

For improved in vivo HIV gene therapy to prevent the spread of viral infection and disease, innovative strategies need to be evaluated to provide pre-exposure protection for patients in both developed and developing countries. In this disclosure, applicants evaluated the capacity of the Sindbis-ZZ envelope design to protect HIV-1 susceptible cells in a gene therapy setting by delivering an anti-HIV CCR5 shRNA specifically to cells expressing CCR5 on the cell surface. Targeted transduction was achieved in mixed cell populations with both cultured and primary cells. Potent knockdown of CCR5 expression (>93%) was observed thus conferring HIV-1 resistance in CCR5 shRNA vector transduced cells.

Example No. 1

Lentiviral Vector Design and Production

A third generation HIV derived lentiviral vector containing an EGFP reporter gene was used in this study, pCCLc-x-PGK-EGFP (FIG. 1). The CCR5 shRNA gene driven by the human polymerase-III U6 small RNA promoter was generated, as described previously, and inserted upstream of the PGK-EGFP reporter gene cassette [47]. Sequencing of clones was confirmed by Laragen Inc., Los Angeles, Calif.

Lentiviral vectors were generated in HEK-293T cells by lipofection with 25 μg of the packaging construct, pΔ8.9 (packaging plasmid containing the gag and pol genes), 25 μg of pCCLc-x-PGK-EGFP (control empty vector) or the CCR5 shRNA construct pCCLc-CCR5shRNA-PGK-EGFP (transfer vector), and 12 μg of pSindbis-ZZ (envelope). Vector supernatants were collected at 72 hours post-transfection and concentrated by ultracentrifugation at 20,000 rpm.

Lentiviral vectors pseudotyped with the Sindbis-ZZ envelope were incubated with a purified CCR5 monoclonal antibody (mAb) (BD Biosciences, San Jose, Calif.) on ice for one hour. Vectors were titered on Ghost-R5-X4-R3 cells which express CCR5 on the cell surface. These cells were obtained from the AIDS Reference and Reagent Program and cultured in complete DMEM with 10% FBS and supplemented with hygromycin, puromycin, and G418 according to the supplier's protocol. CCR5 targeting vectors were incubated on Ghost-R5-X4-R3 cells for two hours at 37° C. with 8 μg/ml protamine sulfate. Complete DMEM containing 10% FBS was then added to the transduced cells. Forty-eight hours post-transduction, cells were analyzed by FACS for EGFP expression. Vector titers ~$1.0*10^7$ TU/ml were routinely achieved.

Example No. 2

Targeted Transduction of Mixed Cell Populations

A mixed population of cultured cells including HEK-293T and Ghost-R5-X4-R3 cells were plated in complete DMEM including 10% FBS. Cells were transduced with the CCR5 targeting vectors, either EGFP-alone or the CCR5-shRNA vector (MOI 10) for two hours at 37° C. with 8 μg/ml protamine sulfate. Peripheral blood mononuclear cells were isolated from whole blood by Ficoll-Paque (GE Healthcare, Piscataway, N.J.). Total white blood cells were cultured in complete RPMI media containing 10% FBS and supplemented with 10 ng/ml IL-2. Cells were either left unstimulated or were stimulated with 1 ug/ml PHA for four days prior to transduction. Both unstimulated and stimulated PBMCs were transduced with the CCR5 targeting vectors, either EGFP-alone or the CCR5-shRNA vector (MOI 10) for two hours at 37° C. with 8 μg/ml protamine sulfate. Four days post-transduction, both cultured cells and primary human PBMCs were analyzed by flow cytometry for EGFP expression and down regulation of CCR5 expression.

Example No. 3

Flow Cytometry Analysis and QRT-PCR

To determine the cell-specific targeted transduction and the subsequent CCR5 down regulation conferred by the CCR5 shRNA, transduced cell populations were analyzed by FACS. Four days post-transduction, nontransduced, EGFP-alone, and CCR5-shRNA lentiviral vector transduced cells, both cultured cells and PBMCs, were analyzed by FACS for EGFP expression. Cultured HEK-293T/Ghost-R5-X4-R3 mixed cells were stained with anti-human PE-conjugated CD4 and CCR5 antibodies (BD Biosciences, San Jose, Calif.) to determine the specificity of transduction and also the down regulation of CCR5 expression in the CCR5-shRNA vector transduced cells. PBMCs were stained with anti-human CD3-APC (T cells), CD19-PE (B cells), CD14-PE (monocyte/macrophage), and CCR5-PE (BD Biosciences, San Jose, Calif.) to determine cell specific targeted transduction and CCR5 down regulation. All FACS data was obtained on a Beckman Coulter Cytomics FC500 flow cytometer and analyzed using CXP analysis software.

To more accurately quantitate the down regulation of CCR5 in CCR5-shRNA transduced cells, quantitative real-time PCR (QRT-PCR) was performed on total RNA extracted from transduced cells using RNA-STAT-60 (Tel-Test, Friendswood, Tex.). First strand cDNA synthesis was generated using the High Capacity cDNA Reverse Transcription Kit (Applied Biosystems, Foster City, Calif.). QRT-PCR was then performed using the SYBR Green PCR Master Mix Kit (Applied Biosystems, Foster City, Calif.) using the primer set, 5'-ACTGCAAAAGGCTGAAGAGC-3' (SEQ ID NO: 6) and 5'-AGCATAGTGAGCCCAGAAGG-3' (SEQ ID NO: 7). GAPDH was used as an internal control.

Example No. 4

HIV-1 Challenge of Transduced Cells

To determine whether the CCR5 targeted transduction and the successive down regulation of CCR5 expression could confer HIV-1 resistance, transduced cells were challenged with BaL-1, an R5-tropic strain of HIV-1. Transduced cells, both HEK-293T/Ghost-R5-X4-R3 mixed cells (MOI 0.01 and 0.05) and PBMCs (MOI 0.01), were challenged with BaL-1 for two hours at 37° C. with 8 μg/ml polybrene. On various days post-infection, cell culture supernatants were sampled for use in p24 antigen ELISA and infectious virus assays. Supernatant aliquots were quantified for p24 by ELISA according to the manufacturer's protocol (Zeptometrix Corp., Buffalo, N.Y.). Challenged cell culture supernatants were also analyzed for infectious virus by the Ghost Cell assay. Briefly, 75 μl of challenge culture supernatant was added to uninfected Ghost-R5-X4-R3 cells ($1.0*10^6$) with 8 μg/ml polybrene for two hours. Forty-eight hours post-infection, infected Ghost-R5-X4-R3 cells were analyzed by flow cytometry for EGFP expression to determine levels of infectious virus particles.

Example No. 5

In Vivo CCR5 Cell Specific Targeting

To determine the in vivo targeting ability of the CCR5 cell specific vector, the immunodeficient NOD/SCID-IL2r-γ knockout mouse model was used to evaluate targeted transduction. Adult mice, at least four months old were sublethally irradiated with 300 rads total body irradiation. Freshly isolated primary human PBMCs were injected retro-orbitally (RO) with $1*10^7$ cells. Cells were allowed to engraft for two weeks and were followed by RO injection with $1*10^6$ TU of the EGFP-alone CCR5 targeting vector. Five days post-injection of vector, single cell suspensions from mouse organs were analyzed for cell specific transduction of engrafted human cells using the PBMC antibody staining panel described above. FACS data was collected on a Beckman Coulter Cytomics FC500 flow cytometer and analyzed with CXP analysis software.

Experimental Results

Figure 2:
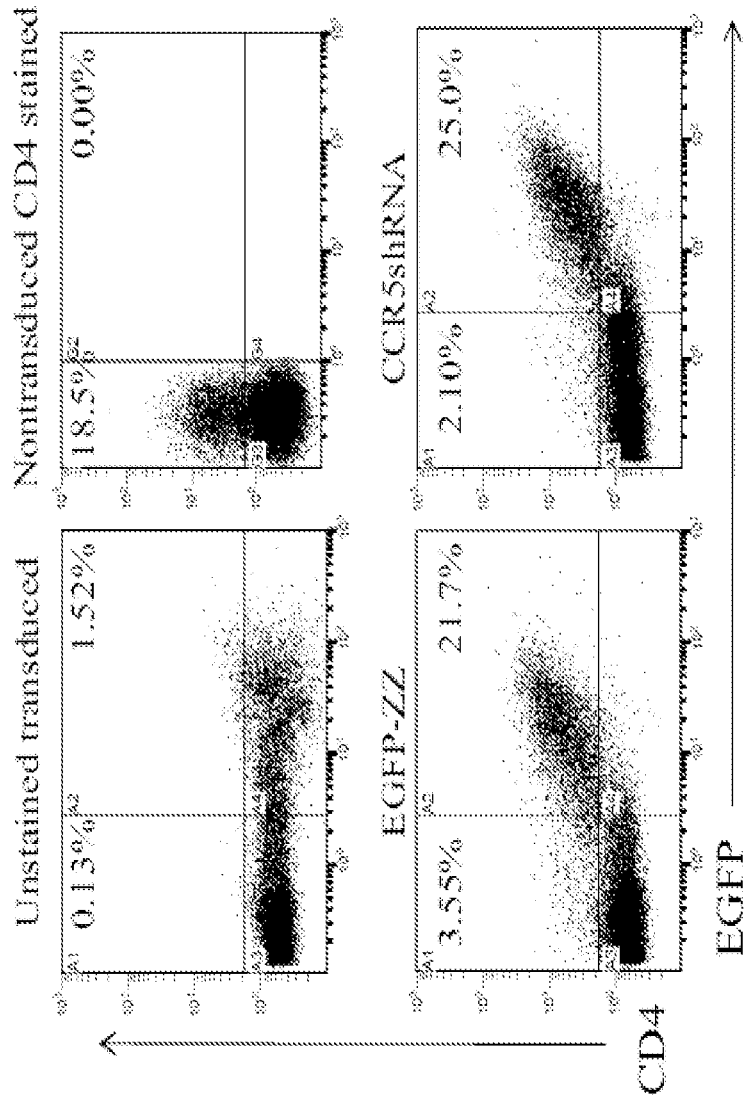
FIG. 2 shows CCR5-positive cell specific targeting of Ghost-R5-X4-R3 cultured cells: a mixed culture of Ghost-R5-X4-R3 and HEK-293T cells was transduced with the CCR5 targeting vectors, EGFP-ZZ and CCR5shRNA-ZZ. Seventy-two hours post-transduction, the cells were stained with a PE-conjugated anti-human CD4 antibody. Cells were analyzed by FACS for CD4 and EGFP expression.
Figure 3:
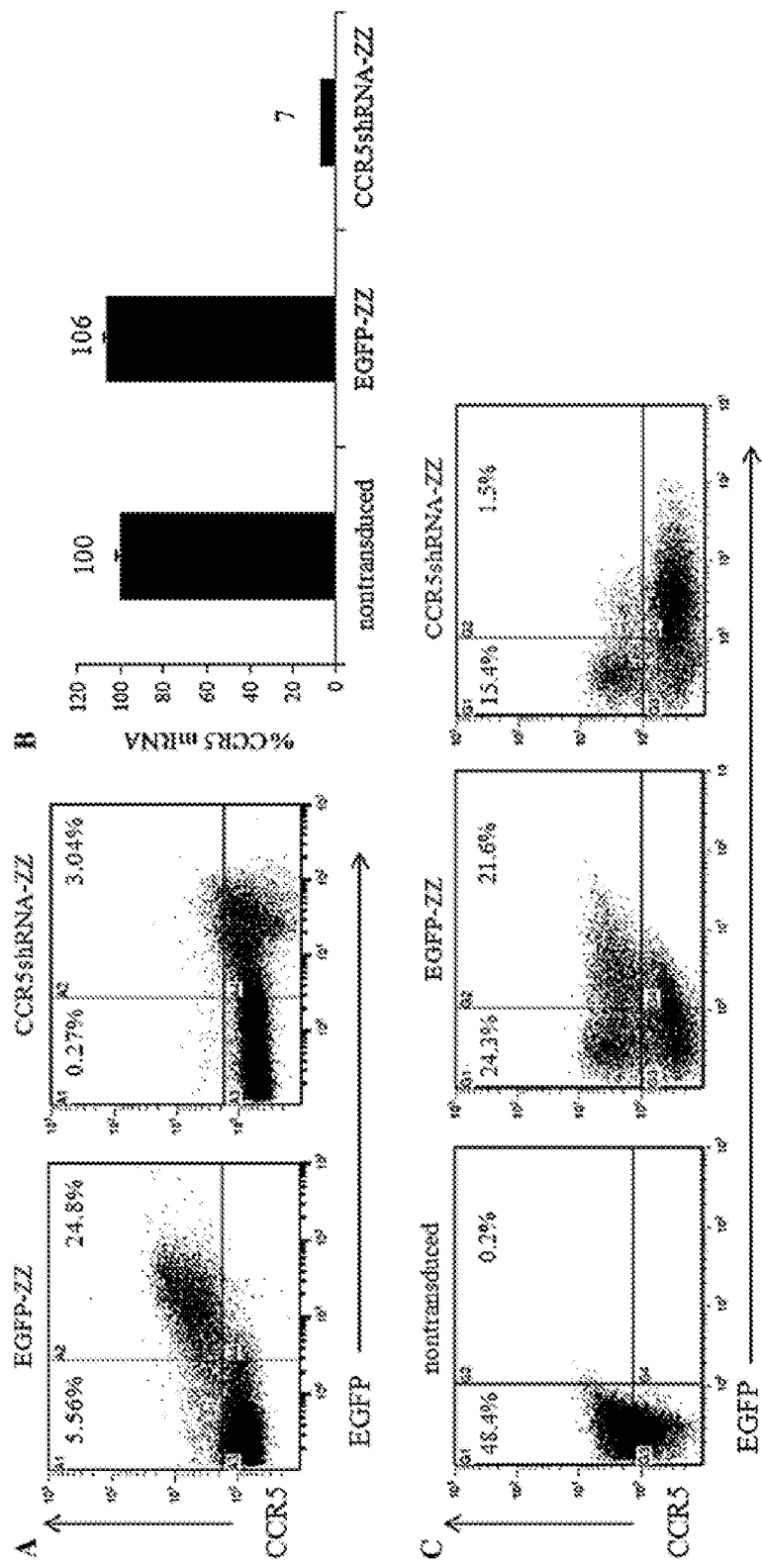
FIG. 3 shows down regulation of CCR5 protein and mRNA levels in transduced Ghost-R5-X4-R3 cells: A mixed culture of Ghost-R5-X4-R3 and HEK-293T cells was transduced with the CCR5 targeting vectors, EGFP-ZZ and CCR5shRNA-ZZ. A) Seventy-two hours post-transduction, the cells were stained with a PE-conjugated anti-human CCR5 antibody and analyzed by FACS for CCR5 and EGFP expression. B) Cells were also analyzed by QRT-PCR for intracellular CCR5 mRNA. C), Human PBMCs were transduced with the CCR5-targeting vectors, EGFP-ZZ and CCR5shRNA-ZZ, and analyzed by FACS for CCR5 and EGFP expression.

CCR5 Cell Specific Transduction and CCR5 Down Regulation:

Lentiviral vectors, both the CCLc-EGFP alone and CCLc-CCR5shRNA, were pseudotyped with the Sindbis virus envelope containing the ZZ-domain from Protein A of *S. aureus* and were evaluated for their ability to specifically transduce CCR5-positive cells when conjugated with a CCR5 mAb. A mixed population of cultured cells including HEK-293T cells (CD4 and CCR5 negative) and Ghost-R5-X4-R3 cells (CD4 and CCR5 positive) were transduced with the CCR5 targeting vectors. Cells were analyzed four days post-transduction for EGFP expression to determine cell specific targeted transduction. Ghost-R5-X4-R3 cells express CCR5 and should be selectively transduced in the mixed cell culture. Another surface molecule, CD4, expressed in the Ghost-R5-X4-R3 cells but not HEK-293T cells, was used as an additional cell detector to analyze targeting specificity using flow cytometry. Only cells expressing CCR5 were transduced as displayed by the double positive staining for CD4 and EGFP expression (FIG. 2). Ghost-R5-X4-R3 cells were selectively transduced by both the EGFP-alone and CCR5-shRNA CCR5 targeting vectors as compared to nontransduced cells in the same cultures which were negative for CD4 and EGFP expression. The transduced mixed cultures of Ghost-R5-X4-R3 and HEK-293T cells were also stained for CCR5 cell surface expression and analyzed by flow cytometry (FIG. 3a). The Ghost-R5-X4-R3 cells transduced with the EGFP-ZZ vector were selectively transduced as displayed by double positive staining for CCR5 and EGFP expression. The CCR5 positive cells were also specifically transduced with the CCR5shRNA-ZZ vector, however, due to the expression of the CCR5 shRNA, a subsequent knock down of CCR5 expression was observed by negative staining for CCR5 within the EGFP positive transduced population. A knockdown level of >93% was observed as compared to nontransduced and EGFP-alone vector transduced cells.

To further quantitate the level of CCR5 knockdown in shRNA transduced Ghost-R5-X4-R3 cells, quantitative real-time PCR (QRT-PCR) was performed to analyze the intracellular levels of CCR5 mRNA. Intracellular CCR5 mRNA levels were decreased in CCR5-shRNA transduced cells, >93%, as compared to control nontransduced and EGFP-alone transduced cells (FIG. 3b). These results correlated with the CCR5 flow cytometry data (FIG. 3a). CCR5 down-regulation, 91%, was also observed in primary PBMC cultures transduced with the CCR5shRNA-ZZ vector (FIG. 3c). The above results established that CCR5-expressing cells can be specifically targeted by the CCR5 antibody-conjugated vector and that these cells, when transduced with the CCR5shRNAZZ vector, have decreased levels of CCR5 expression.

Figure 4:
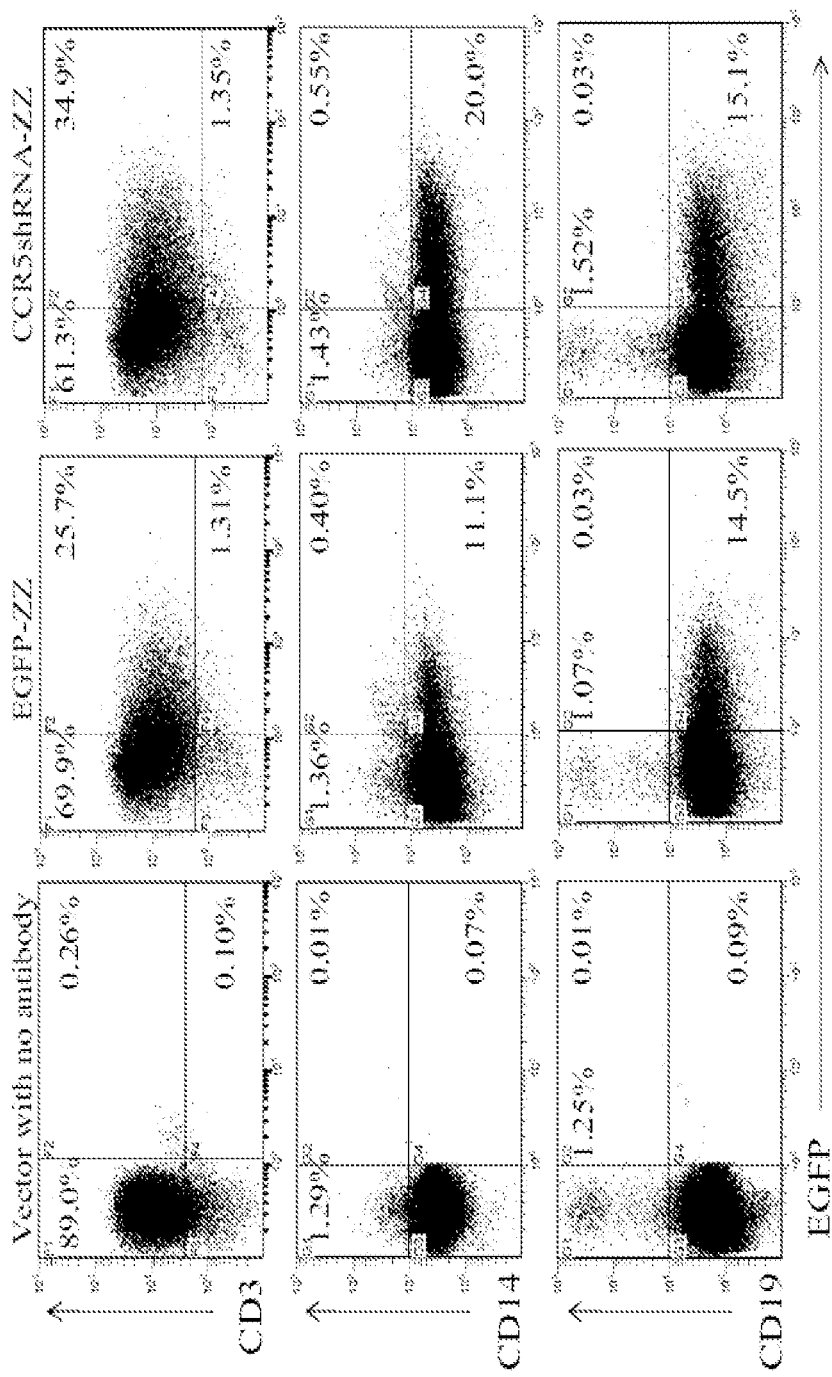
FIG. 4 shows CCR5-positive cell specific targeting of human primary PBMCs: Freshly isolated peripheral blood mononuclear cells were transduced with the CCR5 targeting vectors. Seventy-two hours post-transduction, cells were stained with either an APC-conjugated anti-human CD3 (T cells), PE-conjugated anti-human CD14 monocyte/macrophages), or a PE-conjugated anti-human CD19 (B cells) antibody and analyzed by FACS.

Primary PBMCs, both unstimulated and phytohemagglutinin (PHA) stimulated, were transduced with the CCR5 targeting vector as described above. Both T cell (CD3+) and monocyte/macrophage (CD14+) cell populations were selectively transduced since these cell populations express CCR5 in contrast to B cells (CD19+) which were used as an internal negative control (FIG. 4). Targeted transduction was observed for both the EGFP-ZZ and CCR5shRNA-ZZ vectors as compared to cells transduced with Sindbis-ZZ pseudotyped vector which was not conjugated to the CCR5 mAb. Both unstimulated and stimulated PBMCs displayed similar transduction patterns in both transduction efficiency and specificity (unstimulated cell data not shown). These data confirm the ability of this vector to specifically transduce CCR5 expressing cells and demonstrate that these cells, after transduction with a CCR5-shRNA lentiviral vector, displayed potent knockdown of CCR5 surface expression.

Figure 5:
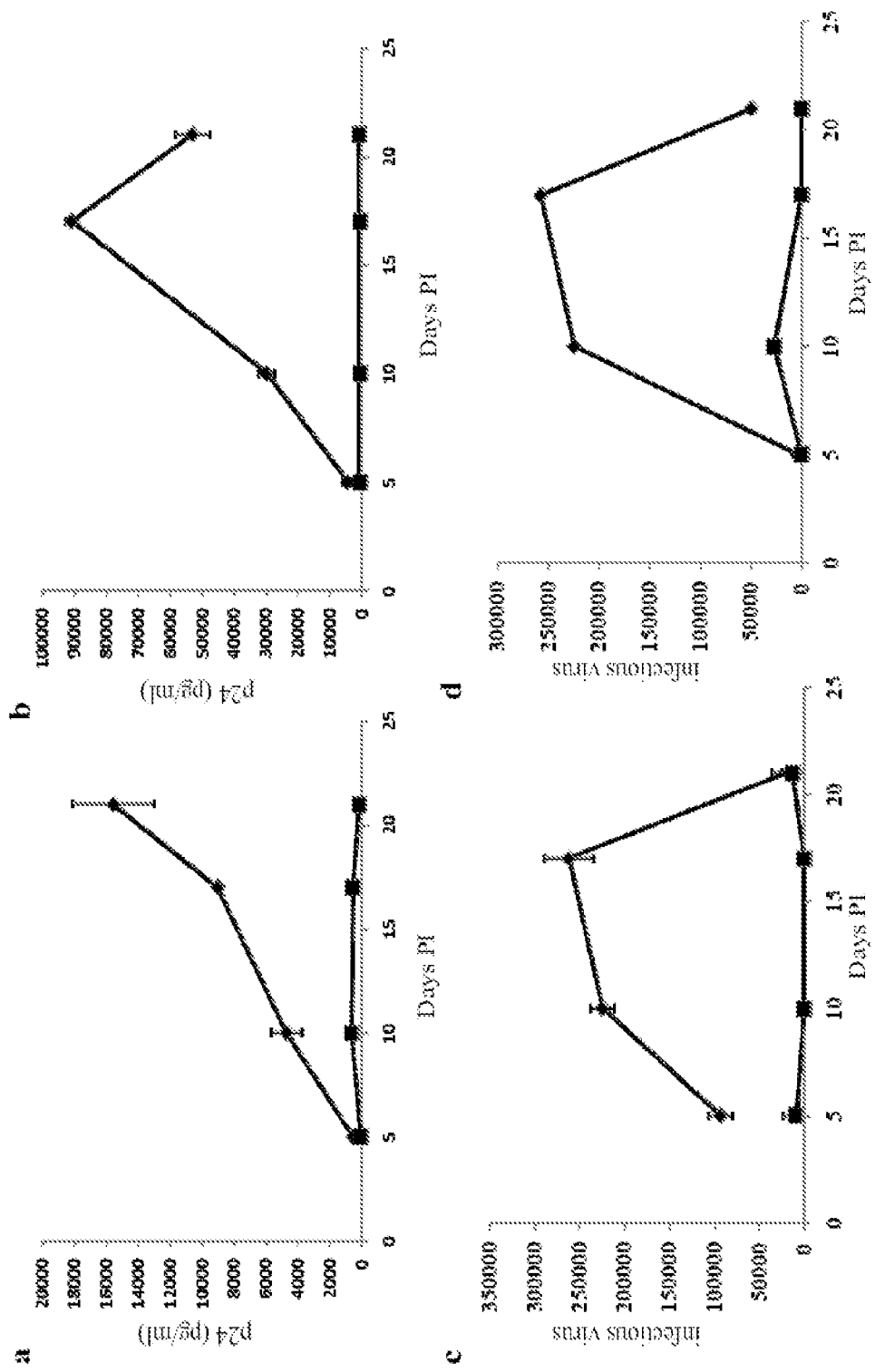
FIG. 5 shows HIV-1 challenge of CCR5 shRNA vector transduced Ghost-R5-X4-R3 cells: Mixed culture Ghost-R5-X4-R3/HEK-293T cells transduced with the EGFP-alone (♦) or CCR5shRNA (■) vector were challenged with an R5-tropic BaL-1 strain of HIV-1. Cell culture supernatants were sampled on various days post-infection and analyzed for p24 antigen by ELISA; (a) MOI and (b) MOI 0.05. Challenge supernatants were also quantitated for infectious virus by a Ghost cell assay; (c) MOI 0.01 and (d) MOI 0.05.
Figure 6:
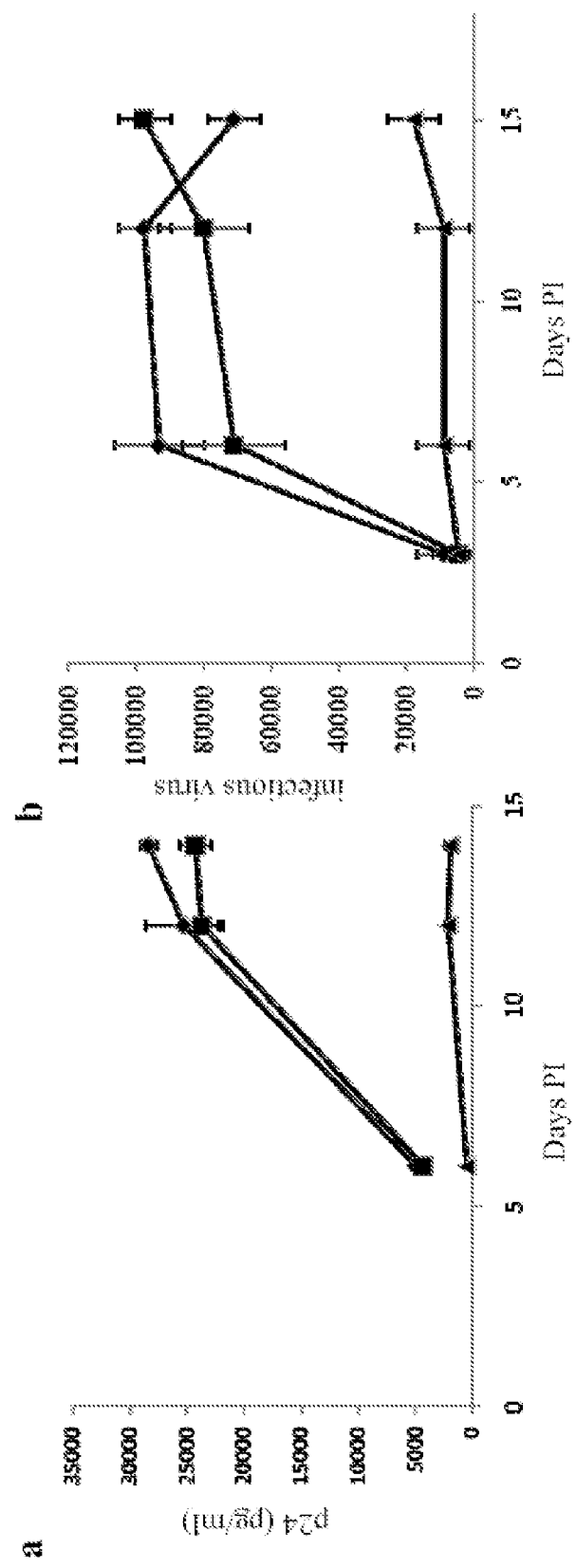
FIG. 6 shows HIV-1 challenge of CCR5 shRNA vector transduced PBMCs: PBMCs, nontransduced (♦), EGFP-alone (■), and CCR5shRNA (▲) vector transduced, were challenged with HIV-1 BaL-1 at an MOI of 0.01. Cell culture supernatants were sampled on various days post-infection and assayed for (a) p24 antigen by ELISA and (b) quantitated for infectious virus by a Ghost cell assay.

HIV-1 Inhibition of CCR5-shRNA Transduced Cells:

To determine whether CCR5 targeted CCR5-shRNA vector transduced cells were capable of resisting HIV-1 infection upon down regulation of cell surface CCR5 expression, cells were challenged with BaL-1, an R5-tropic strain of HIV-1. Challenge experiments were performed at two different multiplicities of infection (MOI), 0.01 and 0.05 to evaluate the level of protection afforded by the potent knockdown of cell surface CCR5. Strong inhibition of viral infection was observed in cultured Ghost-R5-X4-R3 cells transduced with the CCR5-shRNA vector (>1.5 log inhibition) as compared to EGFP-alone transduced cells as measured by p24 antigen ELISA (FIGS. 5a and 5b) and quantitation of infectious virus (FIGS. 5c and 5d). Upon challenge of CCR5 vector targeted PBMCs (MOI 0.01), viral inhibition was observed in CCR5-shRNA transduced cells as compared to nontransduced and EGFP-alone vector transduced cells. Strong protection levels (>1 log) were observed at the peak of viral replication (day 14 post-infection) as measured by p24 antigen ELISA (FIG. 6a) and quantitation of infectious virus (FIG. 6b). These data confirm that targeted transduction of HIV-1 susceptible cells can confer pre-exposure protection to HIV-1 infection by the selective down regulation of CCR5 expression in successfully transduced CCR5 positive cells.

Figure 7:
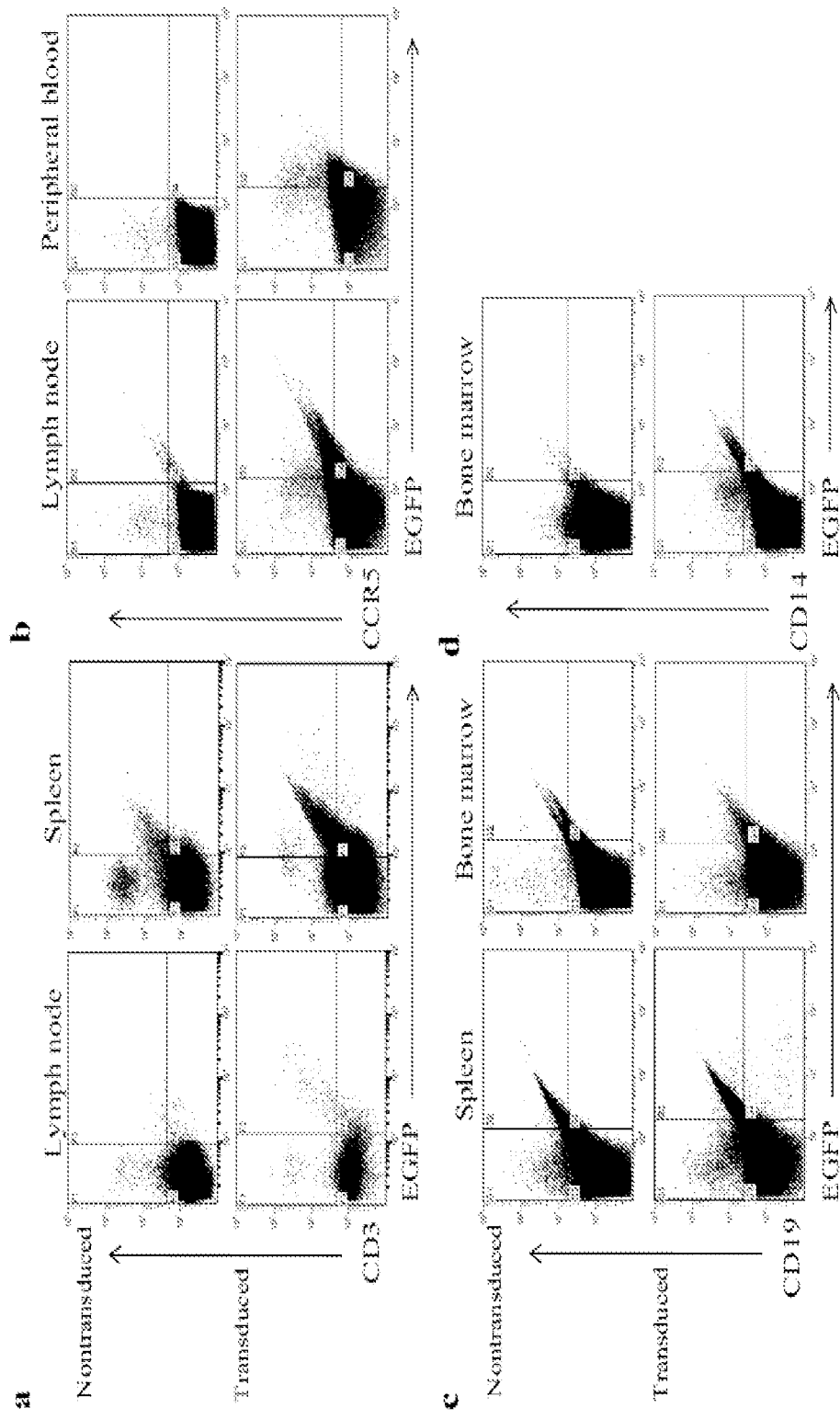
FIG. 7 shows in vivo CCR5-positive cell specific targeting: Adult NOD-SCID-IL2r-γ knockout mice were injected retro-orbitally with fresh PBMCs followed two weeks later by injection with the CCR5 targeting vector. Cells from various lymphoid organs were analyzed for cell transduction by staining for (a) T cells, (b) CCR5, (c) B cells, (d) macrophages and EGFP by FACS.

In Vivo Targeted Transduction of CCR5 Expressing Cells:

The above data confirmed the CCR5 targeting ability of this vector system to selectively transduce cells that are positive for CCR5 expression in vitro. To further evaluate the potential of this targeting vector, the in vivo efficacy was assessed in a NOD/SCID-IL2r-γ knockout mouse model engrafted with freshly isolated human PBMCs. Sublethally irradiated adult mice were injected retro-orbitally (RO) with $1*10^7$ unstimulated PBMCs. Two weeks after cell injection, to allow for human cell engraftment, $1*10^6$ transducing units of the CCR5 targeting vector were injected RO. Five days post-injection with the vector, single cell suspensions from mouse peripheral blood and lymphoid organs were analyzed by FACS to evaluate the in vivo targeted transduction efficiency. Human T cells (CD3+) in the lymph node and spleen (FIG. 7a) and macrophages (CD14+) in the bone marrow (FIG. 7d) were successfully transduced with the CCR5 targeting vector in vivo as displayed by an increase in EGFP expression as compared to engrafted mice not injected with vector. B cells (CD19+) in the spleen and bone marrow (FIG. 7c), however, were not transduced since they do not express CCR5. FACS analysis for CCR5 positive cells was also performed to determine targeting efficiency. Only those cells that were positive for CCR5 expression in the lymph node and peripheral blood were successfully transduced in vivo (FIG. 7b). These results confirm that this novel targeting vector has predictable and reproducible efficacy to target and transduce CCR5 expressing human cells in vivo.

Experimental Discussion

HIV gene therapy can be a very attractive and much needed alternative approach to current small molecule antiretroviral therapies and vaccination strategies for HIV-1 due to its potential for a one-time treatment and long-term HIV-1 protection. Previous and current HIV vaccination strategies including live attenuated, whole inactivated virus, protein subunits, DNA vaccines, and viral expression vectors encoding HIV proteins require a broad response from cells of both the humoral and cytotoxic immune system [6]. However, due to the wide diversity of HIV-1 strains and their ability to evade the host immune response, these techniques have failed to provide effective protection.

Current ex vivo cellular transduction protocols for clinical gene therapy which include bone marrow harvesting, apheresis of PBMCs, and manipulation in a clean room setting, are not feasible in developing countries where sophisticated laboratories and equipment necessary to perform these procedures are unavailable. Therefore, new and innovative ways to transduce and protect HIV-1 susceptible cells, in vivo, need to be developed. Cell specific targeting vectors capable of selectively transducing a particular population of cells of interest, after direct injection into the body, have the potential to protect cells and can provide an "off the shelf" therapy. Numerous strategies have been evaluated for their ability to specifically target cells in vitro and in vivo [30-41]. One approach utilizes the ability of the Sindbis virus envelope to pseudotype lentiviral vectors. By inserting the immunoglobulin binding ZZ-domain of Protein A from *S. aureus* into the binding region of the Sindbis virus E2 glycoprotein, these envelopes are then able to bind monoclonal antibodies [48-49]. This strategy is simple yet ingenious since only one type of vector needs to be manufactured in large scale, certified, and stored. Depending on which cell population will be targeted, one specific, well characterized monoclonal antibody can be selected and conjugated to a small portion of the vector to render a cell-specific vector preparation which is then suitable for in vivo targeting and transduction.

Mainly R5-tropic strains of HIV-1 which utilize CCR5 as a coreceptor are primarily responsible for viral transmission and early stage infection [48]. These strains establish a primary infection and viral reservoir in an infected individual. Targeting CCR5 through therapeutic approaches utilizing either small molecule HIV-1 entry inhibitors or gene silencing by siRNAs in a gene therapy setting, offers a promising way to inhibit and possibly prevent initial HIV-1 infection. As observed with the natural Δ32-bp deletion mutant allele occurring in individuals resistant to HIV-1 infection, a targeted approach to knockdown expression of CCR5 in the HIV susceptible population could provide protection from HIV infection. The Sindbis-ZZ strategy was applied to construct a CCR5 positive cell-specific targeting vector for inhibition of initial HIV-1 infection by intracellular immunization with a CCR5 shRNA.

Upon incubation with the CCR5 targeting vector, only those cells expressing CCR5 were selectively transduced with a lentiviral vector expressing a highly potent CCR5 shRNA capable of potent knockdown of CCR5 gene expression. This approach was successful in mixed cell populations of both cultured and primary human cells. Transduction of freshly isolated PBMCs with the CCR5 targeting vector demonstrated transduction of only T cells and monocyte/macrophage populations which express CCR5 on the cell surface and are the major cell types normally infected by HIV-1. B cells in the culture remained nontransduced since they do not express CCR5, demonstrating specificity. Transduction was also shown to be dependent on vector conjugation with a monoclonal antibody. When cells were incubated with vector not conjugated to any antibody, no transduction was observed (FIG. 4). These data confirm the necessity for a specific mAb for the vector to elicit an effect, and also verify the lack of nonspecific transduction by unconjugated vector particles. Also, PBMCs, both unstimulated and stimulated with PHA displayed similar levels of transduction efficiency with the EGFP-ZZ and CCR5shRNA-ZZ vectors. This suggests that the targeting efficacy and transduction ability of the CCR5 targeting vector is independent of cell stimulation. Targeted transduction of CCR5 expressing cells with the CCR5 shRNA vector conferred to HIV-1 target cells a potent ability to down regulate the expression of CCR5 and to be protected from HIV-1 infection as measured by p24 antigen ELISA and by quantitating infectious virus (FIGS. 5 and 6). A slight rise in viral replication was observed in the CCR5 shRNA transduced population due to infected nontransduced cells, however, a subsequent decrease in detection of virus followed after the infected cells were killed. This observation highlights the selective survival advantage of CCR5 shRNA transduced cells which were able to resist infection during the course of the virus challenge and to eventually take over the culture.

The efficacy of this targeting strategy was further evaluated, in vivo, in a NOD/SCID-IL2r-γ knockout mouse model engrafted with freshly isolated human PBMCs. Upon irradiation, injection of cells, and engraftment of the PBMCs, the mice were injected with the CCR5 targeting lentiviral vector. Cell specific transduction was observed in both the T cell and monocyte/macrophage cell populations in a similar manner as seen in the in vitro PBMC transductions. Specific cell targeting could be demonstrated in vivo by the fact that none of the human B cells were transduced, as measured by EGFP expression (FIG. 7*c*). This lack of B cell transduction could also be observed in the in vitro experiments, and is due to the absence of the CCR5 receptor on B cells. Upon retro-orbital injection, the CCR5 targeting vector will first drain into the lymphatics and selectively transduce cells in the lymph nodes followed by transduction of cells in other lymphoid organs and in the peripheral blood. The flow of vector particles from the retro-orbital capillary beds to the lymphatics was confirmed by the high T cell transduction efficiency observed in the lymph nodes (FIG. 7*a*).

The results presented here offer an encouraging and alternative method to provide pre-exposure prophylaxis for HIV-1 infection by utilizing an HIV-1 susceptible cell-specific targeting strategy via direct injection of vector particles. This innovative strategy could potentially be applied as a pre-exposure protection for highly susceptible human populations, even in areas where sophisticated laboratories are not available. Upon injection with the CCR5 cell-specific targeting vector and after transduction of a sufficient number of CCR5 expressing cells, individuals coming in contact with HIV could potentially resist the initial infection due to expression of the CCR5 shRNA to silence CCR5 and thus block HIV-1 entry. Gene therapy could therefore aid in transferring the genetic ability to resist HIV-1 infection to susceptible individuals by silencing the expression of CCR5, mimicking the natural ability of individuals harboring the Δ32-bp mutant allele to resist infection.

Experiment B—from Pre-Integration HIV-1 Inhibition

Background

Pre-entry and pre-integration inhibition of infection is an ideal method to elicit resistance to HIV-1 infection. Therapies aimed at blocking HIV-1 integration will combat the generation of provirus and the further establishment of a viral reservoir which is the main reason for the failure to cure an HIV infected individual. A number of pre-integration anti-HIV transgenes have been previously tested as individual constructs and have displayed strong resistance to HIV-1 infection [5, 9, 11, 14, 15, 16, 43]. By combining multiple anti-HIV genes in a single vector, a novel anti-HIV vector could be produced which not only provides strong inhibition of HIV-1 infection but would also provide a block to the generation of escape mutants by creating a difficult environment for HIV to mutate around the multiple anti-HIV molecules.

In the initial stages of HIV-1 infection, attachment and fusion to target cells occurs via interaction of the viral envelope gp120 and gp41 glycoproteins with the cellular major receptor CD4 and a minor coreceptor, two of these being CCR5 and CXCR4 which are members of the chemokine receptor family. CCR5 is utilized by R5-tropic strains of HIV-1 primarily during the initial stages of infection, followed by a switch in tropism to X4-tropic HIV-1 which is mainly detected during late stage infection [44]. In a small percentage of the human population, a mutant allele of the CCR5 gene, containing a 32-base pair deletion, renders the protein defective and therefore the receptor is absent from the cell surface. Homozygous and heterozygous individuals harboring this allele have been reported to be resistant to HIV-1 infection and remain physiologically normal due to receptor redundancy in the chemokine system [26-28]. Recently, long term control of viral replication was observed in an HIV-1 infected individual who received a stem cell transplant for acute myeloid leukemia [29]. The transplanted allogeneic stem cells were from an individual who was homozygous for the CCR5 Δ32-bp deletion. The results provided from this study demonstrate the importance in developing anti-HIV molecules which block the use of CCR5 during HIV-1 infection. Based on this natural phenotype of CCR5 null, CCR5 knockdown for HIV gene therapy offers a promising approach to inhibit viral infection at the level of viral entry.

The mechanism of RNA interference using small interfering RNAs is a highly potent method to silence gene expression and offers an ideal approach to knock down expression of CCR5 [24]. Numerous reports have evaluated the efficacy of CCR5 gene knockdown using small interfering RNAs (siRNAs) and have demonstrated protection from HIV-1 infection [11, 14-16]. However, the silencing of CCR5 gene expression, alone, will not be sufficient to completely inhibit HIV infection and also would not inhibit infection from X4-tropic or dual-tropic viral strains. Other anti-HIV strategies added to the CCR5 knockdown would therefore greatly enhance viral protection.

Another naturally occurring molecule, TRIM5α, has been shown to inhibit HIV-1 infection at the post-entry/pre-integration stage by disrupting the uncoating of the viral capsid upon entering the cytoplasm [45]. Certain isoforms of TRIM5α found in Old World monkeys are capable of strongly restricting HIV-1 infection. Humans also naturally express a distinct isoform of TRIM5α but it does not afford protection from HIV-1 infection. A recently developed human/rhesus macaque chimeric TRIM5α isoform, incorporating a small number of key HIV-restrictive amino acids, was demonstrated to inhibit HIV-1 infection in a hematopoietic stem cell gene therapy setting [43, 46]. If used in a clinical application, the design of this chimeric TRIM5α molecule, which consists of mainly human amino acid sequences, will help to avoid immune rejection which would occur with the use of wild-type rhesus macaque TRIM5α. A third molecule, a TAR decoy, has been previously described to inhibit transactivation of proviral transcription [12]. By mimicking the structure of the viral transcriptional responsive element (TAR), the TAR decoy is able to bind the viral Tat protein and sequester it away from its normal action of aiding efficient proviral HIV transcription.

In the present study, applicants describe the construction and pre-clinical evaluation of a triple combination anti-HIV lentiviral vector that focuses on the pre-integration block of HIV-1 infection to minimize the formation of integrated provirus and the generation of escape mutants. The three highly potent anti-HIV transgenes, a chimeric TRIM5α molecule, a CCR5 shRNA capable of almost complete knockdown of CCR5 expression, and a TAR decoy, combined in a single vector, displayed complete protection from productive viral infection and integration of multiple strains of HIV-1 upon transduction into HIV target cells. These results establish the future application of this vector for use in a clinical setting.

HIV infection continues to spread worldwide in both developed and underdeveloped countries with no effective vaccine available. Current antiretroviral drug therapies have been successful in suppressing viral infection as long as the patient is compliant with the prescribed regimen. However, with prolonged use, these treatments can become toxic and drug resistant viral escape mutants arise [1-5]. New and innovative therapies need to be developed that overcome the limitations of current small drug antiretrovirals. Gene therapy offers a promising alternative or supplement to current treatments due to advantages which include the possibility of a one-time treatment, controlled or constitutive anti-HIV gene expression, and long-term viral inhibition particularly if hematopoietic progenitor cells (HPCs) are targeted. Many anti-HIV genes have been evaluated for their efficacy in inhibiting viral infection including antisense RNAs, riboyzymes, RNA decoys, siRNAs, intrabodies, transdominant proteins, and restriction factors [8-23, 42, 43]. These molecules have been targeted to both viral genes and proteins and also cellular genes critical for viral infection and replication. Several groups, have been involved with human clinical trials using a select number of these anti-HIV genes transferred into HPCs by retroviral and lentiviral vectors [19-23]. However, improvements in stem cell transduction efficiency and in the effectiveness of the vector to interfere with different stages of the HIV life cycle are still needed.

Pre-entry and pre-integration inhibition of infection is an ideal method to elicit resistance to HIV-1 infection. Therapies aimed at blocking HIV-1 integration will combat the generation of provirus and the further establishment of a viral reservoir which is the main reason for the failure to cure an HIV infected individual. A number of pre-integration anti-HIV transgenes have been previously tested as individual constructs and have displayed strong resistance to HIV-1 infection [5, 9, 11, 14, 15, 16, 43]. By combining multiple anti-HIV genes in a single vector, a novel anti-HIV vector could be produced which not only provides strong inhibition of HIV-1 infection but would also provide a block to the generation of escape mutants by creating a difficult environment for HIV to mutate around the multiple anti-HIV molecules.

In the initial stages of HIV-1 infection, attachment and fusion to target cells occurs via interaction of the viral envelope gp120 and gp41 glycoproteins with the cellular major receptor CD4 and a minor coreceptor, two of these being CCR5 and CXCR4 which are members of the chemokine receptor family. CCR5 is utilized by R5-tropic strains of HIV-1 primarily during the initial stages of infection, followed by a switch in tropism to X4-tropic HIV-1 which is mainly detected during late stage infection [44]. In a small percentage of the human population, a mutant allele of the CCR5 gene, containing a 32-base pair deletion, renders the protein defective and therefore the receptor is absent from the cell surface. Homozygous and heterozygous individuals harboring this allele have been reported to be resistant to HIV-1 infection and remain physiologically normal due to receptor redundancy in the chemokine system [26-28]. Recently, long term control of viral replication was observed in an HIV-1 infected individual who received a stem cell transplant for acute myeloid leukemia [29]. The transplanted allogeneic stem cells were from an individual who was homozygous for the CCR5 Δ32-bp deletion. The results provided from this study demonstrate the importance in developing anti-HIV molecules which block the use of CCR5 during HIV-1 infection. Based on this natural phenotype of CCR5 null, CCR5 knockdown for HIV gene therapy offers a promising approach to inhibit viral infection at the level of viral entry.

The mechanism of RNA interference using small interfering RNAs is a highly potent method to silence gene expression and offers an ideal approach to knock down expression of CCR5 [24]. Numerous reports have evaluated the efficacy of CCR5 gene knockdown using small interfering RNAs (siRNAs) and have demonstrated protection from HIV-1 infection [11, 14-16]. However, the silencing of CCR5 gene expression, alone, will not be sufficient to completely inhibit HIV infection and also would not inhibit infection from X4-tropic or dual-tropic viral strains. Other anti-HIV strategies added to the CCR5 knockdown would therefore greatly enhance viral protection.

Another naturally occurring molecule, TRIM5α, has been shown to inhibit HIV-1 infection at the post-entry/pre-integration stage by disrupting the uncoating of the viral capsid upon entering the cytoplasm [45]. Certain isoforms of TRIM5α found in Old World monkeys are capable of strongly restricting HIV-1 infection. Humans also naturally express a distinct isoform of TRIM5α but it does not afford protection from HIV-1 infection. A recently developed human/rhesus macaque chimeric TRIM5α isoform, incorporating a small number of key HIV-restrictive amino acids, was demonstrated to inhibit HIV-1 infection in a hematopoietic stem cell gene therapy setting [43, 46]. If used in a clinical application, the design of this chimeric TRIM5α molecule, which consists of mainly human amino acid sequences, will help to avoid immune rejection which would occur with the use of wild-type rhesus macaque TRIM5α. A third molecule, a TAR decoy, has been previously described to inhibit transactivation of proviral transcription [12]. By mimicking the structure of the viral transcriptional responsive element (TAR), the TAR decoy is able to bind the viral Tat protein and sequester it away from its normal action of aiding efficient proviral HIV transcription.

In the present study, the construction and pre-clinical evaluation of a triple combination anti-HIV lentiviral vector is described that focuses on the pre-integration block of HIV-1 infection to minimize the formation of integrated provirus and the generation of escape mutants. The three highly potent anti-HIV transgenes, a chimeric TRIM5α molecule, a CCR5 shRNA capable of almost complete knockdown of CCR5 expression, and a TAR decoy, combined in a single vector, displayed complete protection from productive viral infection and integration of multiple strains of HIV-1 upon transduction into HIV target cells. Our results establish the future application of this vector for use in a clinical setting.

Example No. 6

Lentiviral Vector Design and Production

Figure 8:
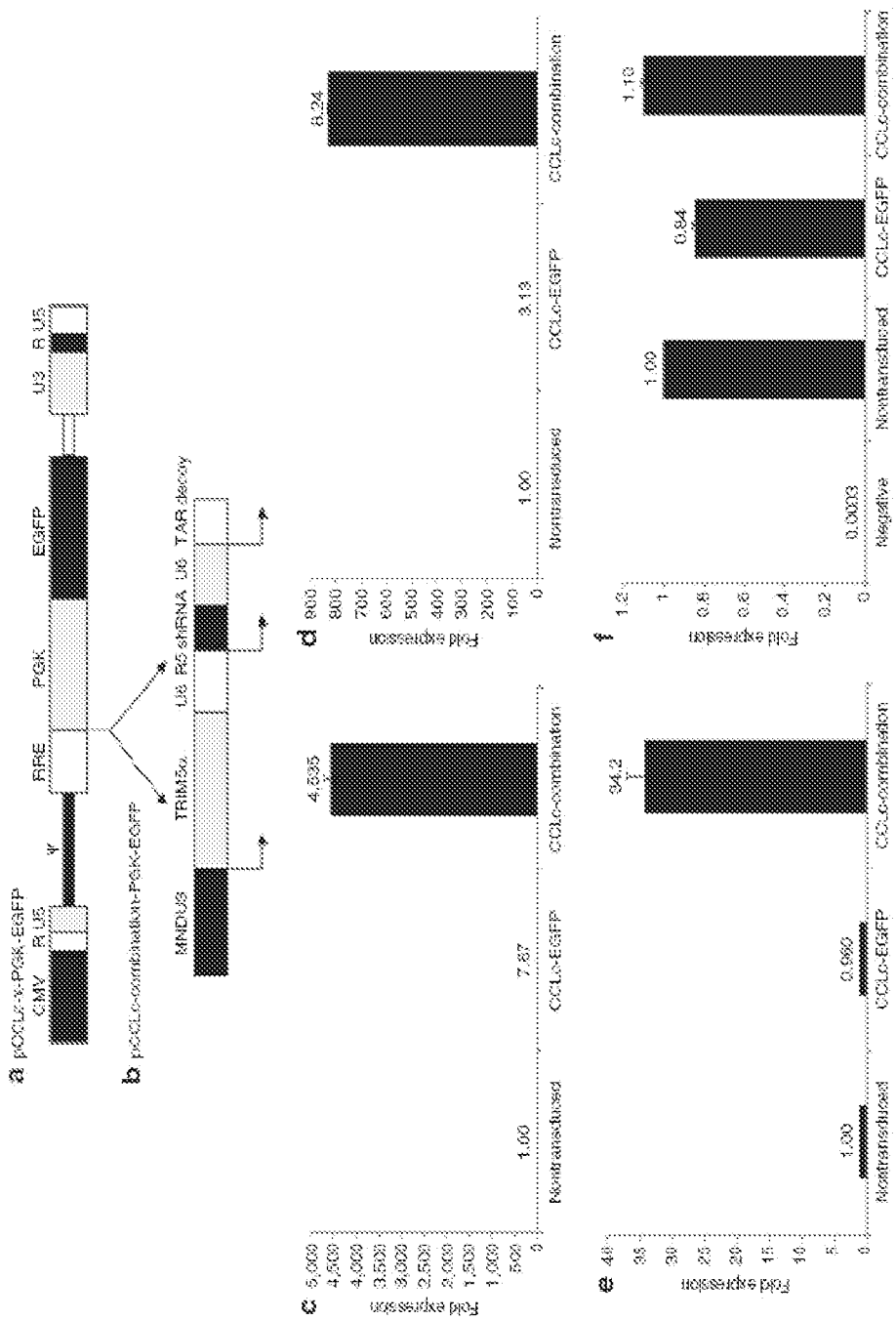
FIG. 8 shows a combination anti-HIV lentiviral vector: a third generation lentiviral vector, pCCLc-x-PGK-EGFP, which contains an EGFP reporter gene was used to generate the combination anti-HIV construct (a). The three transgenes, a chimeric human/rhesus macaque TRIM5α driven by the MNDU3 promoter, a CCR5 shRNA driven by the human polymerase-III small RNA U6 promoter, and a TAR decoy driven by the U6 promoter were inserted upstream of the EGFP reporter gene to derive pCCLc-Combination-PGK-EGFP (b). Ghost-R5-X4-R3 cells were left nontransduced or were transduced with the EGFP alone or combination lentiviral vectors. Total cellular RNA was extracted and analyzed by quantitative real-time PCR for expression of (c) TRIM5α, (d) the CCR5 shRNA, and (e) the TAR decoy using gene-specific primers. (f) U6 snRNA was used as an internal control. Experiments were performed in triplicate. EGFP, enhanced green fluorescent protein; HIV, human immunodeficiency virus; shRNA, short hairpin RNA; TAR, transactivation response element.

A third-generation HIV-derived lentiviral vector containing an EGFP reporter gene was used in this study, pCCLc-MNDU3-x-PGK-EGFP (FIG. 8a). A chimeric human/rhesus macaque TRIM5α gene was inserted into the lentiviral vector under the control of the MNDU3 promoter. The human polymerase-III U6 promoter driven CCR5 shRNA expression cassette was generated, as described previously, and inserted directly downstream of the MNDU3-TRIM5α gene [47]. The TAR decoy expression cassette was generated in a similar way to the CCR5 shRNA cassette and inserted directly downstream from the CCR5 shRNA gene. All three of these anti-HIV expression cassettes were inserted upstream of the EGFP reporter gene to derive pCCLc-Combination-PGK-EGFP (FIG. 8b). Sequencing of clones was confirmed by Laragen Inc., Los Angeles, Calif.

Lentiviral vectors were generated in HEK-293T cells. Twenty-five micrograms of the packaging construct, pΔ8.9 (packaging plasmid containing the gag and pol genes), 25 μg of pCCLc-MNDU3-x-PGK-EGFP (control empty vector) or the combination vector, pCCLc-MNDU3-TRIM5α-U6-CCR5shRNA-U6-TARdecoy-PGK-EGFP (transfer vector), and 5 μg of VSVG (envelope). DNA plasmids were transfected into cells in T225 flasks by lipofection. Vector supernatants were collected at 48 hours post-transfection and concentrated by ultrafiltration.

Example No. 7

Transduction of Cultured Cells and Primary CD34+ HPCs

Ghost-R5-X4-R3 cultured cells obtained from the AIDS Reference and Reagent Program were cultured in complete DMEM including 10% FBS supplemented with hygromycin, puromycin, and G418 according to the supplier's protocol. Cells were transduced with the lentiviral vectors, either EGFP-alone or the combination vector (MOI 10) for two hours at 37° C. with 8 μg/ml protamine sulfate. Complete medium was then added to the cells.

CD34+ hematopoietic progenitor cells (HPCs) were isolated from umbilical cord blood (NDRI, Philadelphia, Pa.) by Ficoll-Paque (GE Healthcare, Piscataway, N.J.) and purified by magnetic bead column separation (Miltenyi Biotec, Auburn, Calif.). CD34+ cell isolation purity (>93%) was routinely obtained. Total CD34+ cells were cultured in complete IMDM media containing 10% FBS and supplemented with 50 ng/ml SCF, Flt-3 ligand, and TPO. Cells were transduced with the lentiviral vectors EGFP-alone or the combination vector (MOI 10) for three hours at 37° C. with 8 ug/ml protamine sulfate. Two days post-transduction, cells were sorted based on EGFP expression and cultured in semi-solid methylcellulose medium with growth factors (Stem Cell Technologies, Vancouver, BC, Canada) for 12 days to derive mature macrophages. After differentiation, cells were removed from the methylcellulose medium and plated in 6-well plates in complete DMEM medium with 10% FBS supplemented with 10 ng/ml of GM-CSF and M-CSF. Media was changed every two days for four days to derive mature macrophages. Both nontransduced and lentiviral vector transduced cultured and primary CD34+ cell derived macrophages were used for subsequent experiments.

Example No. 8

Flow Cytometry and QRT-PCR

To determine if cells transduced with the combination lentiviral vector had decreased levels of CCR5 due to the expression of the CCR5 shRNA, cells were analyzed by FACS. Seventy-two hours post-transduction, transduced Ghost-R5-X4-R3 cells were stained with a PE-conjugated anti-human CCR5 antibody (BD Biosciences, San Jose, Calif.). CD34+ cell derived macrophages, nontransduced, EGFP-alone transduced, and combination vector transduced cells, were stained with antibodies to detect normal macrophage cell surface markers including, CD14-PE, CD4-PE, and CD68-PE (BD Biosciences, San Jose, Calif.). All FACS data was obtained on a Beckman Coulter Cytomics FC500 flow cytometer and analyzed on CXP analysis software.

To further quantitate the levels of CCR5 knockdown in combination lentiviral vector transduced cells, quantitative real-time PCR (QRT-PCR) was performed on transduced cell RNA. Total RNA was extracted from Ghost-R5-X4-R3 cells using RNA-STAT-60 (Tel-Test Inc., Friendswood, Tex.). First strand cDNA synthesis was performed using the High Capacity cDNA Reverse Transcription Kit (Applied Biosystems, Foster City, Calif.). QRT-PCR was then performed using the SYBR Green PCR Master Mix Kit (Applied Biosystems, Foster City, Calif.) with primers: 5'-ACTGCAAAAGGCT-GAAGAGC-3' (SEQ ID NO: 6) and 5'-AGCATAGTGAGC-CCAGAAGG-3' (SEQ ID NO: 7). GAPDH was used as an internal control.

To quantitate the levels of integrated HIV-1 provirus following viral challenge of transduced cells, QRT-PCR was performed on the cell's genomic DNA. Total genomic DNA was isolated from challenged cells using the Wizard Genomic DNA Isolation System (Promega, Madison, Wis.). QRT-PCR was performed using the Taqman PCR Core Reagents Kit (Applied Biosystems, Foster City, Calif.) using the primers 5'-CTGGCTACTATTTCTTTTGCTA-3' (SEQ ID NO: 8) and 5'-TGGCATGGGTACCAGCACA-3' (SEQ ID NO: 9) and probe 5'-TTTATCTACTTGTTCATTTCCTCCAAT-TCCTT-3' (SEQ ID NO: 10) (IDT DNA Technologies, Coralville, Iowa). The single copy albumin gene was used as an internal control.

Example No. 9

HIV-1 Challenge of Vector Transduced Cells

To determine whether the expression of the triple combination of anti-HIV genes conferred resistance to HIV-1 infection, transduced cells were challenged with R5, X4, and dual-tropic strains of HIV-1, BaL-1, NL4-3, and 89.6, respectively. Ghost-R5-X4-R3 cells, nontransduced, EGFP-alone, and combination vector transduced, were incubated with R5-tropic BaL-1 and X4-tropic NL4-3 strains of HIV-1, MOI 0.01 and 0.05, for two hours at 37° C. with 8 µg/ml polybrene. On various days post-infection, challenge supernatants were sampled for use in an HIV-1 p24 antigen ELISA and infectious virus assays. Nontransduced and transduced CD34+ cell derived macrophages were similarly challenged with BaL-1 at MOIs of 0.01 and 0.05. On various days post-infection, challenge supernatants were sampled for use in an HIV-1 p24 antigen ELISA (Zeptometrix Corp., Buffalo, N.Y.) and infectious virus assays.

Viral escape mutants can be generated after prolonged use with current anti-retroviral therapies. To determine if escape mutants were generated upon challenge of combination transduced cells, subsequent challenges were performed with culture supernatants from the initial HIV-1 challenge experiments. Naïve Ghost-R5-X4-R3 cells, nontransduced, EGFP-alone, and combination vector transduced, were challenged with culture supernatants from their respective day 25 HIV-1 challenge supernatants from the initial challenge experiment. On various days post-infection, culture supernatants were sampled for infectious virus. Briefly, supernatants (75 ul) from viral challenges were incubated on naïve nontransduced Ghost-R5-X4-R3 cells for 2 hours at 37° C. with 8 µg/ml polybrene. Complete cell culture media was added. Forty-eight hours post-infection, cells were analyzed by FACS for EGFP expression to quantitate the levels of infectious virus.

Example No. 10

Selective Survival Advantage of Combination Vector Transduced Cells

To evaluate whether combination vector transduced cells have a selective survival advantage over nontransduced cells, a mixed culture of both cell types was challenged with HIV-1. Mixed populations of cells, with ratios of 1:1 and 2:1, transduced cells (either EGFP-alone or combination vector transduced) to nontransduced cells, were challenged with R5 and X4-tropic strains of HIV-1, BaL-1 and NL4-3, respectively, at an MOI of 0.01. Cells were analyzed by FACS for EGFP expression on day 0 (pre-infection) and on day 21 post-infection to evaluate the survival advantage of the transduced cell populations.

Example No. 11

Immune Cell Activation Assay

The insertion of the rhesus macaque TRIM5α 13-aa patch into the C-terminal region of the human TRIM5α isoform may result in immune activation and rejection of cells expressing the chimeric TRIM5α molecule. To determine if immune system cells were capable of responding to the presentation of the 13-aa patch, an MTT cell activation assay was performed. Fresh PBMCs were isolated by Ficoll-Paque and plated in 96-well plates in complete RPMI with 10% FBS and supplemented with 10 ng/ml IL-2. Monocytes and dendritic cells were allowed to attach to the bottom of the wells. Lymphocytes were removed and plated in separate wells. Monocytes/dendritic cells were pulsed overnight with small peptides corresponding to either a human TRIM5α 11-aa patch (GARGTRYQTFV (SEQ ID NO: 4)) or the rhesus macaque TRIM5α 13-aa patch (QAPGTLFTFPSLT (SEQ ID NO: 5)) which was used to generate the chimeric TRIM5α isoform. Peptides were synthesized by Genscript (Piscataway, N.J.). A separate set of monocytes/dendritic cells were pulsed with LPS as a positive control. A fourth set of monocytes/dendritic cells were incubated with PHA 1 ug/ml to act as a positive T cell activation control. The fifth set of monocytes/dendritic cells were left unmanipulated to serve as a negative nonactivated control. Lymphocytes were added back to the cultures the following day. On various days post-addition of the lymphocytes, the MTT cell activation assay was performed on the cells according to the manufacturer's protocol (Roche Applied Science, Indianapolis, Ind.).

Experimental Results

High Titer Vector Production and Transduction with Lentiviral Vectors:

A third generation lentiviral vector, CCLC-MNDU3-X-PGK-EGFP, was utilized to construct the triple combination anti-HIV vector (FIG. 8a). The three genes inserted into this vector include a human/rhesus macaque TRIM5α isoform, a CCR5 shRNA, and a TAR decoy (FIG. 8b). By combining these three genes, a potent pre-integration block to HIV-1 infection could be established due to the pre-entry block by the knockdown of CCR5 expression and the post-entry/pre-integration block by the chimeric TRIM5α. If infectious virus is able to circumvent the potent inhibition established by the first two anti-HIV molecules, the TAR decoy will prevent upregulation of HIV-1 transcription.

With the incorporation of three anti-HIV genes into a single gene therapy vector which is based on HIV, detrimental effects on the quantity of vector production and titer due to the increased size of the vector payload and also the anti-HIV effects of the vector transgenes could be possible. Therefore, combination vector titers were compared to control EGFP-alone titers on HEK-293T cells. Combination vector titers, upon 100-fold concentration, were found to be, on average, ~5*$10^9$ TU/ml compared to EGFP-alone vector titers which generated ~3.5*$10^9$ TU/ml (data not shown). This excludes any negative effects on vector titer using our combination vector construct and packaging system.

Due to the complexity of this combination vector containing three anti-HIV expression cassettes and a fourth EGFP reporter gene, expression levels of the downstream transcripts, including the two polymerase (pol)-III transcription units, may be affected. Expression of all three anti-HIV genes was confirmed by quantitative real-time PCR (QRT-PCR). The expression levels of the chimeric TRIM5α (FIG. 8c), CCR5 shRNA (FIG. 8d), and TAR decoy (FIG. 8e) were 4,535-, 824-, and 34-fold higher, respectively, compared to control cells that do not express any of the anti-HIV genes. The levels of the internal control U6 snRNA were consistent among all cell types (FIG. 8f).

Figure 16:
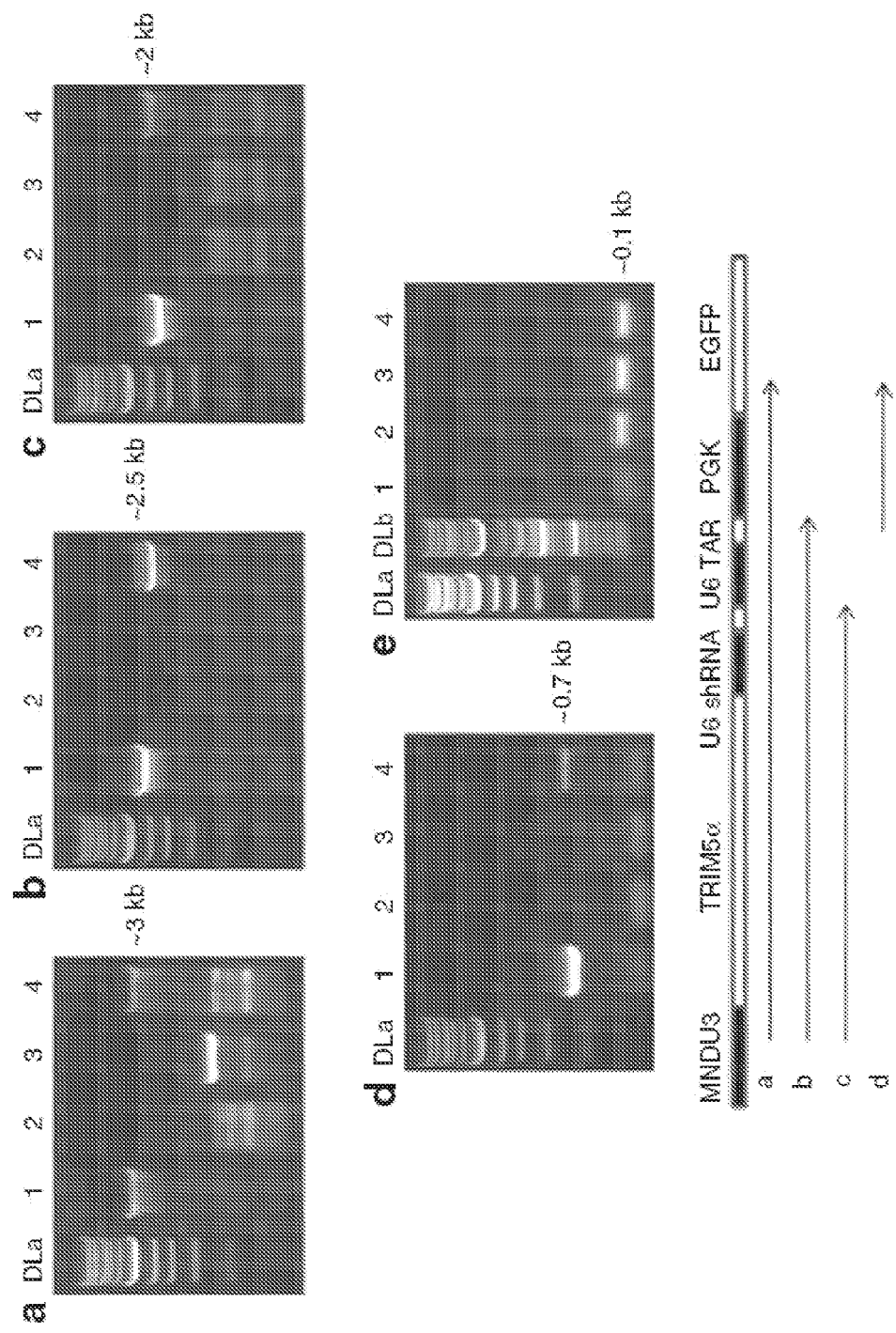
FIG. 16 shows gel pictures confirming stability of the combination vector in transduced cells. Ghost-R5-X4-R3 cells were left nontransduced or were transduced with the EGFP alone or combination lentiviral vectors. Total genomic DNA was extracted and analyzed by PCR with primers specific for the respective vector transgenes. (a) MNDU3 (forward) and EGFP (reverse), (b) MNDU3 (forward) and TAR decoy (reverse), (c) MNDU3 (forward) and CCR5 shRNA (reverse), (d) TAR decoy (forward) and EGFP (reverse), and (e) albumin (forward and reverse). One kilobase DNA ladder (DLa), log DNA ladder (DLb), combination transfer vector plasmid (lane 1), nontransduced cells (lane 2), EGFP-alone vector transduced (lane 3), and combination vector transduced (lane 4). A schematic of the PCR products is below the panels. EGFP, enhanced green fluorescent protein; kb, kilobase; TAR, transactivation response element.
Figure 17:
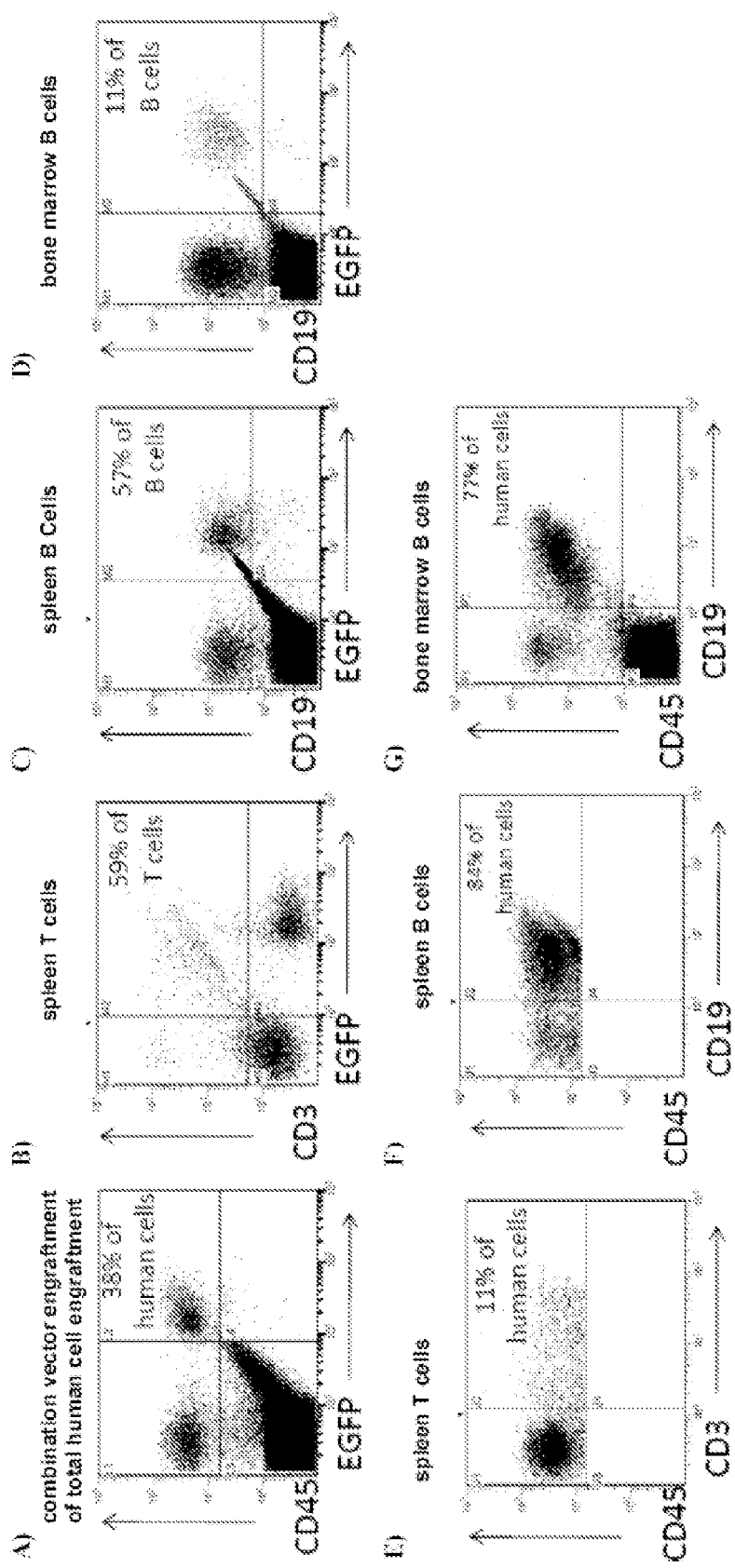
FIG. 17 is a FACS analysis of cells isolated from knock-out mice transplanted with CD34+ hematopoietic cells transduced with combination anti-HIV lentiviral vectors.

The stability of the vector in transduced cells is also a concern due to its complexity. To evaluate any vector deletions or rearrangements that may have occurred, genomic PCR was performed with vector transgene specific primers: FIG. 17a shows MNDU3 forward and EGFP reverse [~3 kilobases (kb)], FIG. 16b shows MNDU3 forward and TAR decoy reverse (~2.5 kb), FIG. 16c shows MNDU3 forward and CCR5 shRNA reverse (~2 kb), FIG. 16d shows TAR decoy forward and EGFP reverse (~0.7 kb), and FIG. 16e shows albumin forward and reverse (~0.1 kb). As displayed in FIG. 16, no deletions or rearrangements were detected, as PCR bands from genomic DNA from combination transduced Ghost-R5-X4-R3 cells (lane 4) corresponded to PCR bands amplified from the combination transfer vector plasmid (lane 1) used in vector preparations. This was in contrast to nontransduced (lane 2) and EGFP-alone-transduced cells (lane 3) that did not amplify the correct PCR products and only displayed background bands. A schematic of the theoretical PCR products is displayed below the panels.

Due to the insertion of the three anti-HIV genes, transduction efficiencies obtained with the combination vector could also be negatively affected. In order to determine if there was such an effect, both cultured Ghost-R5-X4-R3 cells and primary CD34+ hematopoietic progenitor cells (HPCs), were transduced with the control EGFP-alone vector and the anti-HIV gene combination vector. Transduction efficiencies were not affected by use of the combination vector, regardless of the MOI chosen, as observed by EGFP expression during FACS analysis. Transduction efficiencies in cultured Ghost-R5-X4-R3 cells and primary CD34+ HPCs at an MOI of 10 were greater than 95% and 50%, respectively, for each vector transduction (data not shown).

Figure 9:
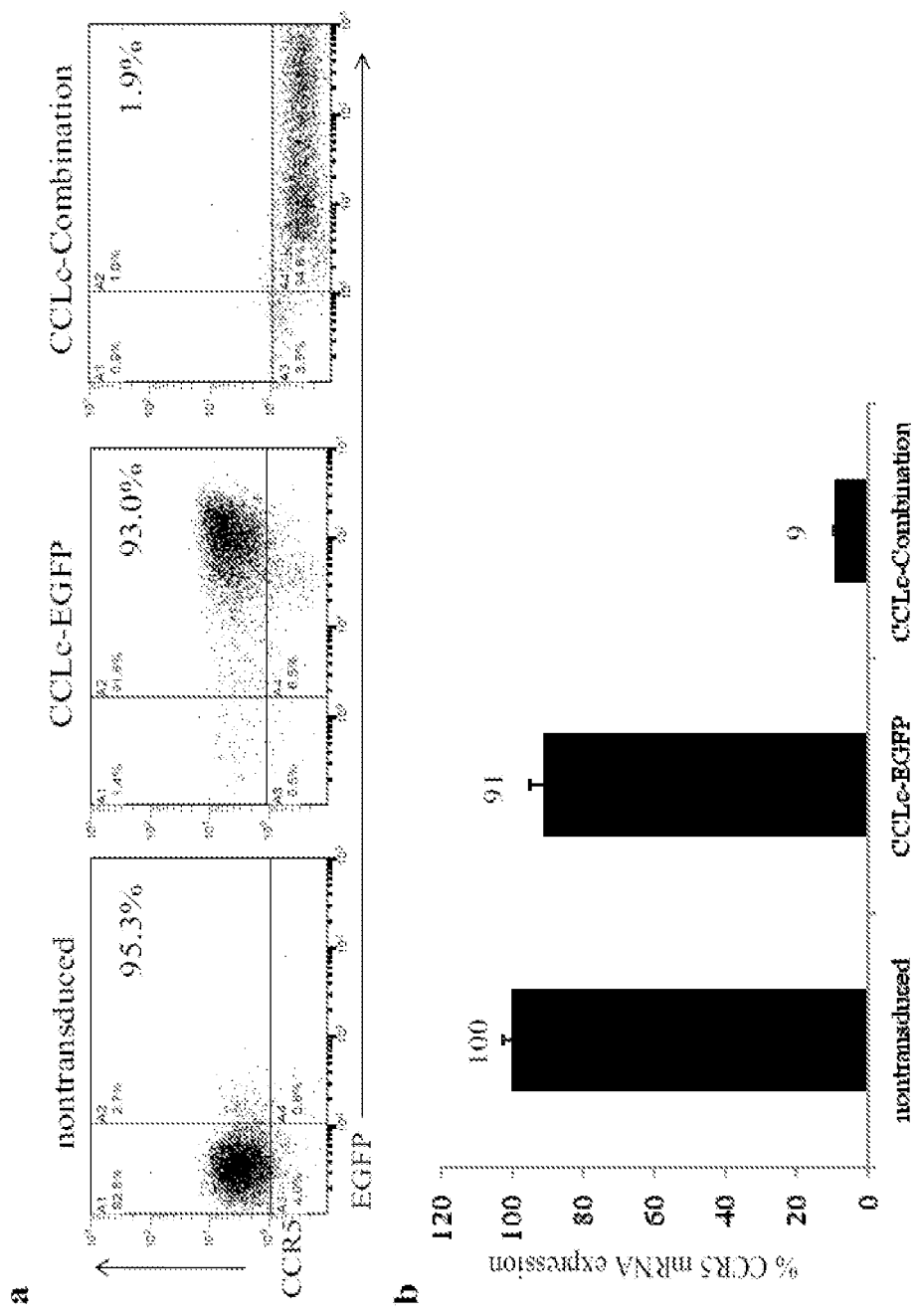
FIG. 9 shows down regulation of CCR5 surface expression and mRNA levels in transduced cells: lentiviral vector transduced Ghost-R5-X4-R3 cells were transduced with the EGFP-alone and combination lentiviral vectors. (a) Seventy-two hours post-transduction, the cells were analyzed for CCR5 expression by FACS. (b) Cells were also analyzed by QRT-PCR for intracellular CCR5 mRNA levels.

CCR5 Down-Regulation in Combination Vector Transduced Cells:

To determine if successful transduction of cells with the combination anti-HIV lentiviral vector conferred knockdown of CCR5 expression, transduced cells were analyzed by FACS for CCR5 surface expression. As seen in FIG. 9a, the combination vector transduced Ghost-R5-X4-R3 cells displayed dramatic knockdown of CCR5 expression (>92%) as compared to nontransduced and EGFP-alone transduced cells. To further quantitate the levels of CCR5 gene silencing in combination vector transduced cells, quantitative real-time PCR (QRT-PCR) was performed. Cells expressing the CCR5 shRNA displayed high levels of knockdown of CCR5 expression (>91%) as compared to nontransduced and EGFP-alone transduced cells (FIG. 9b). These data confirm a potent knockdown of CCR5 gene expression in cells transduced with the combination lentiviral vector.

Figure 10:
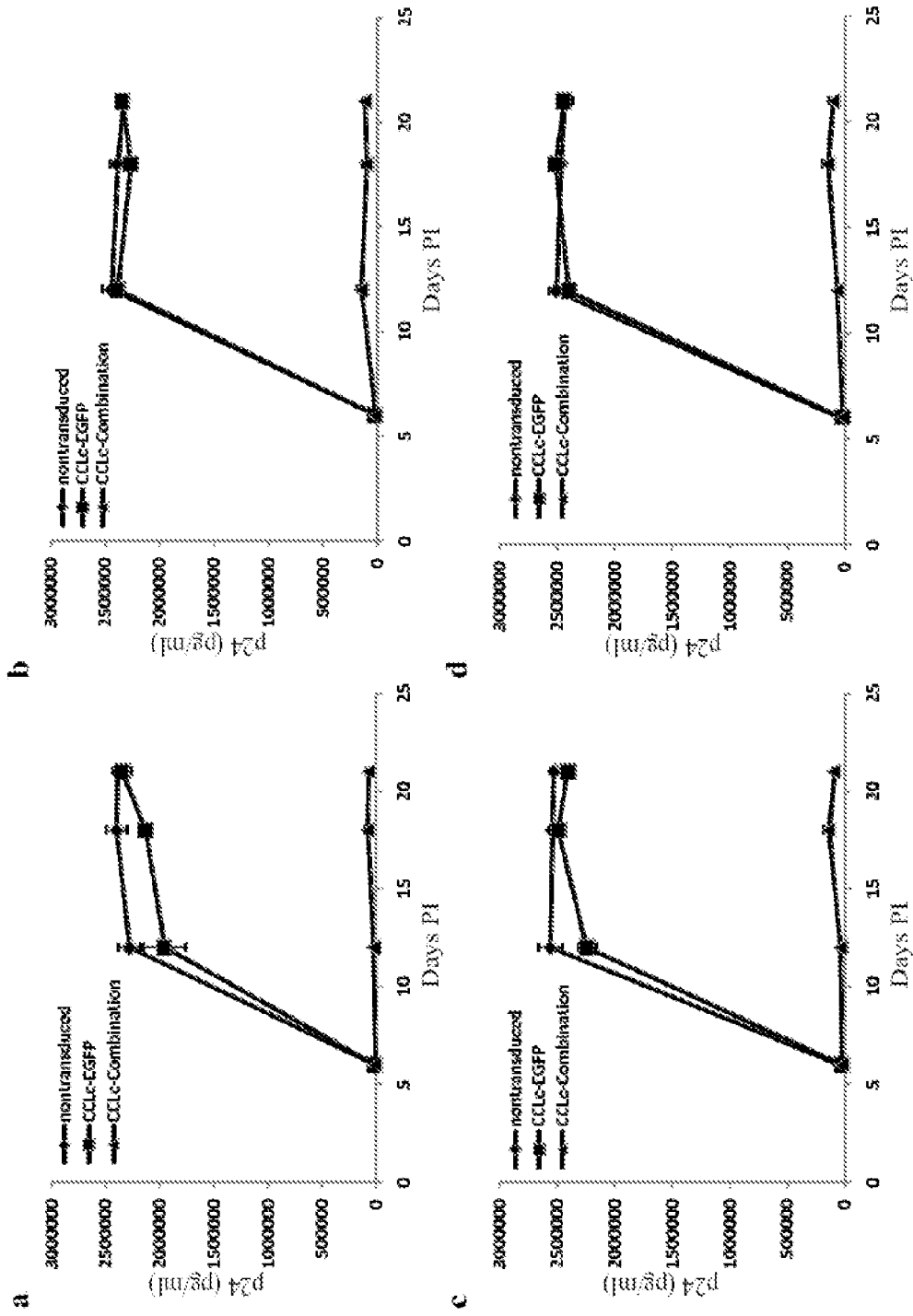
FIG. 10 shows HIV-1 challenge of combination vector transduced cultured cells: Ghost-R5-X4-R3 cells were transduced with the EGFP-alone (■) or the combination (▲) lentiviral vector. Nontransduced (♦) and vector transduced cells were subsequently challenged with the R5-tropic BaL-1 strain of HIV-1 at an MOI of (a) 0.01 and (b) 0.05. Cells were also challenged with the X4-tropic NL4-3 strain of HIV-1 at an MOI of (c) 0.01 and (d) 0.05. On various days post-infection, cell culture supernatants were analyzed for HIV-1 p24 antigen by ELISA.
Figure 11:
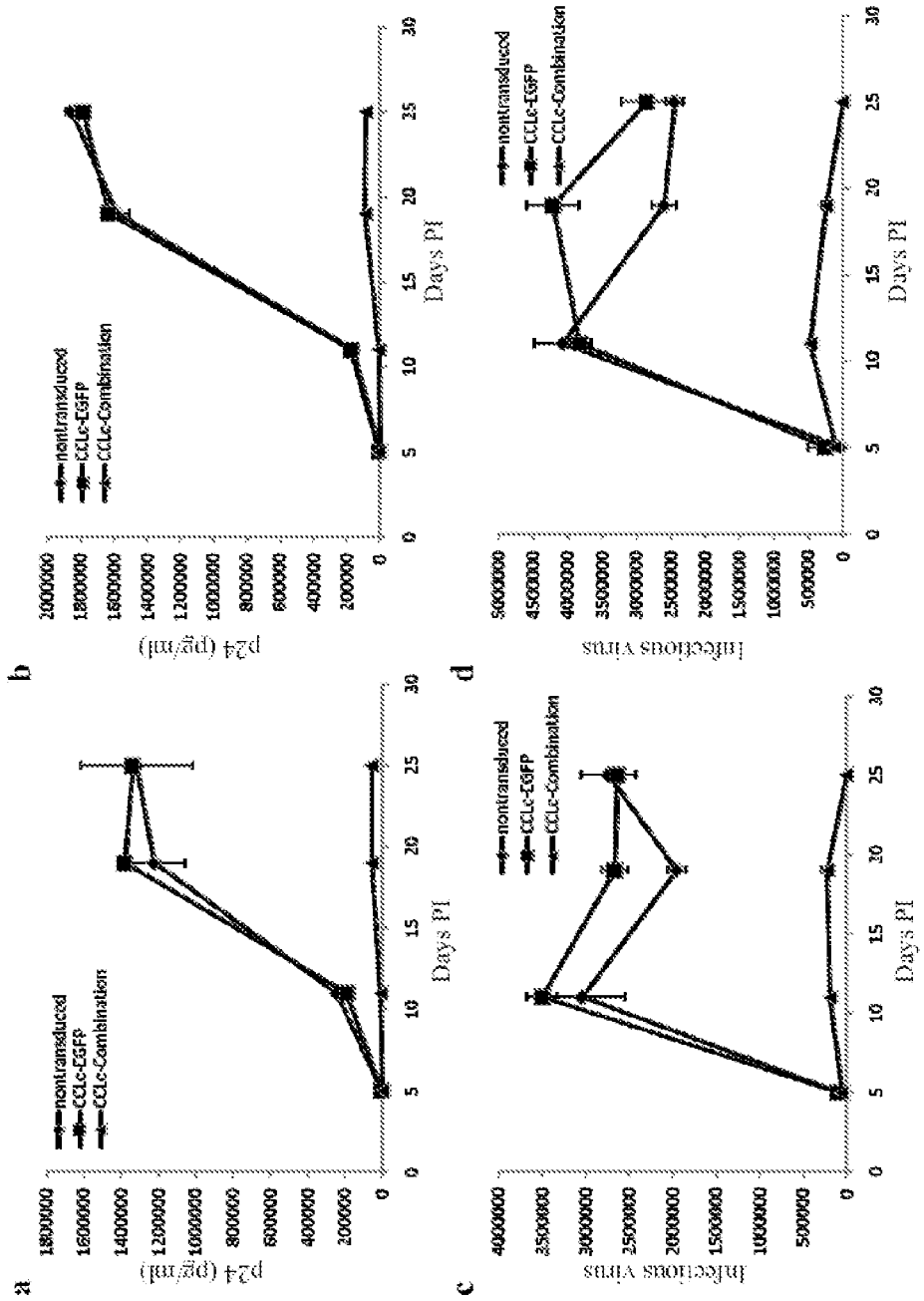
FIG. 11 shows HIV-1 challenge of combination vector transduced CD34+ HPC derived macrophages: CD34+ hematopoietic progenitor cells were transduced with the EGFP-alone (■) or the combination (▲) lentiviral vector and cultured in a macrophage differentiation medium. Upon development of mature macrophages, nontransduced (♦) and vector transduced cells were challenged with the R5-tropic BaL-1 strain of HIV-1. Cell culture supernatants were sampled and analyzed for HIV-1 p24 antigen by ELISA (a) (MOI 0.01) and (b) (MOI 0.05). Challenge supernatants were also analyzed for infectious virus by a Ghost cell assay (c) (MOI 0.01) and (d) (MOI 0.05).

HIV-1 Challenge of Combination Vector Transduced Cells:

Cultured Ghost-R5-X4-R3 cells and primary macrophages are susceptible to infection from R5 and X4-tropic strains of HIV-1. However, upon transduction with the combination anti-HIV lentiviral vector, transduced cells should be resistant to HIV-1 infection. To determine if transduction and expression of the three anti-HIV genes conferred viral resistance, cells were challenged with various strains of HIV-1. Combination vector transduced Ghost-R5-X4-R3 cells displayed strong HIV-1 resistance and inhibition of viral replication (>1.5 log) after challenge with both R5 (BaL-1) (FIG. 10a,b) and X4-tropic (NL4-3) (FIG. 10c,d) strains of HIV-1 at multiple MOIs (0.01 and 0.05) as compared to nontransduced and EGFP-alone vector transduced cells as measured by p24 antigen ELISA. CD34+ HPC derived macrophages transduced with the combination vector also displayed strong inhibition of R5-tropic BaL-1 HIV-1 infection (>1.5 log) at multiple MOIs compared to control nontransduced and EGFP-alone transduced cells Inhibition was observed by p24 antigen ELISA (FIG. 11a,b) and by quantitating total infectious virus using a Ghost cell assay (FIG. 11c,d).

Figure 12:
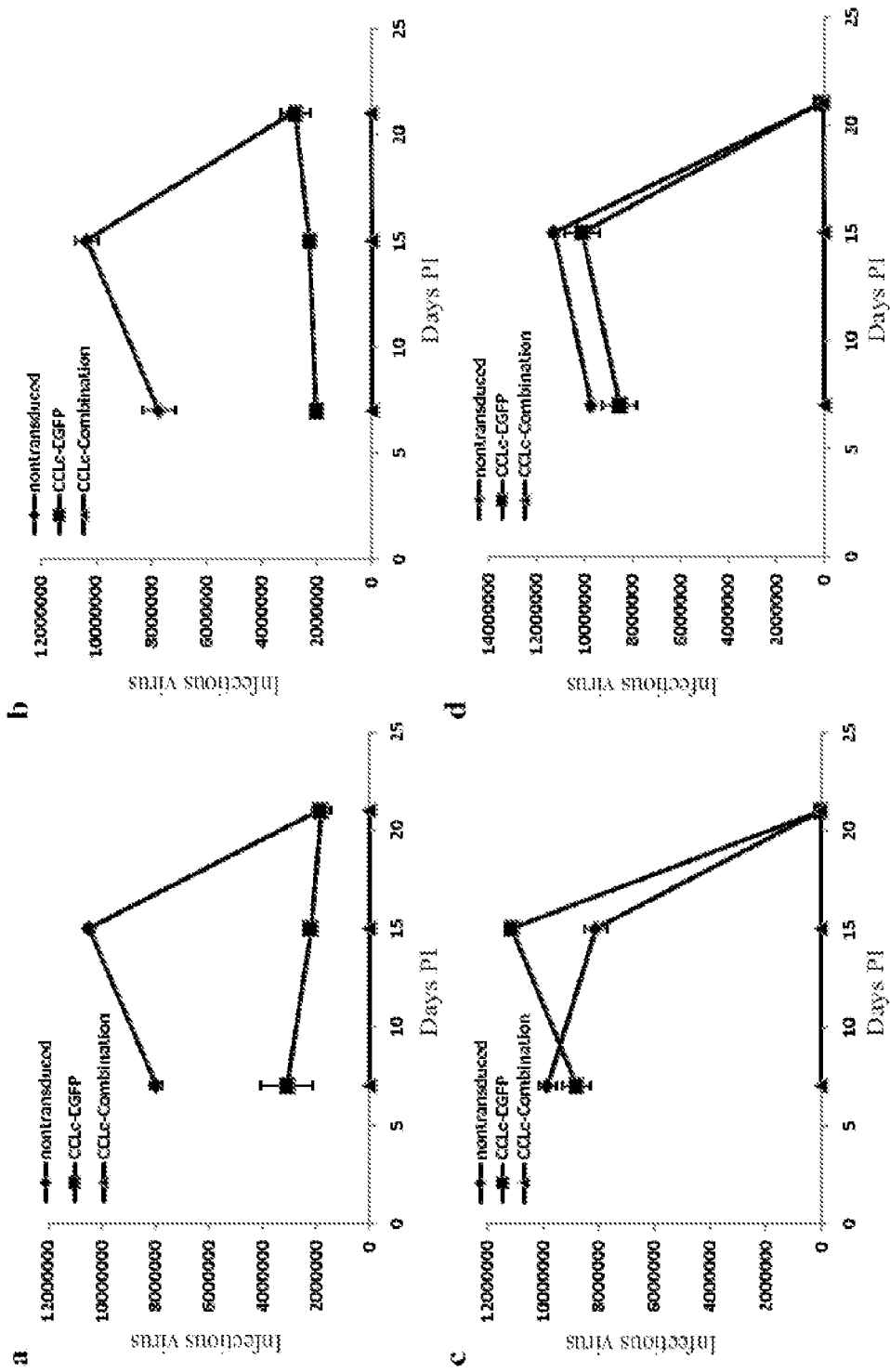
FIG. 12 shows a generation of escape mutants after long-term viral challenge: Naïve nontransduced (♦), EGFP-alone (■), and combination (▲) vector transduced Ghost-R5-X4-R3 cells were challenged with the day 25 culture supernatants from their respective initial viral challenges: (a) BaL-1 MOI 0.01, (b) BaL-1 MOI 0.05, (c) NL4-3 MOI 0.01, and (d) NL4-3 MOI 0.05. Cell culture supernatants were analyzed for infectious virus by a Ghost cell assay.

To evaluate the possible generation of escape mutants arising in long-term HIV-1 challenged combination vector transduced cells, a secondary challenge experiment was performed. Naïve cells, nontransduced, EGFP-alone, and combination vector transduced cells were challenged using the respective viral supernatant from the last time point (day 25) of the initial challenge experiment. Cell culture supernatants were monitored for three weeks to identify any virus replication resulting from the generation of escape mutants. As seen in FIG. 12, no viral replication was detected in challenged cells transduced with the combination lentiviral vector: BaL-1 MOI 0.01 (FIG. 12a), BaL-1 MOI 0.05 (FIG. 12b), NL4-3 MOI 0.01 (FIG. 12c), and NL4-3 MOI 0.05 (FIG. 12d). In contrast, control nontransduced and EGFP-alone vector transduced cells were successfully infected initially which resulted in detection of infectious virus. The levels of infectious virus then started to decrease after day 15 post-infection due to killing of infected cells within the cultures. The results from the secondary challenge experiments confirmed that no viral escape mutants could be detected in culture supernatants from combination vector transduced cells challenged long-term with HIV-1.

Figure 13:
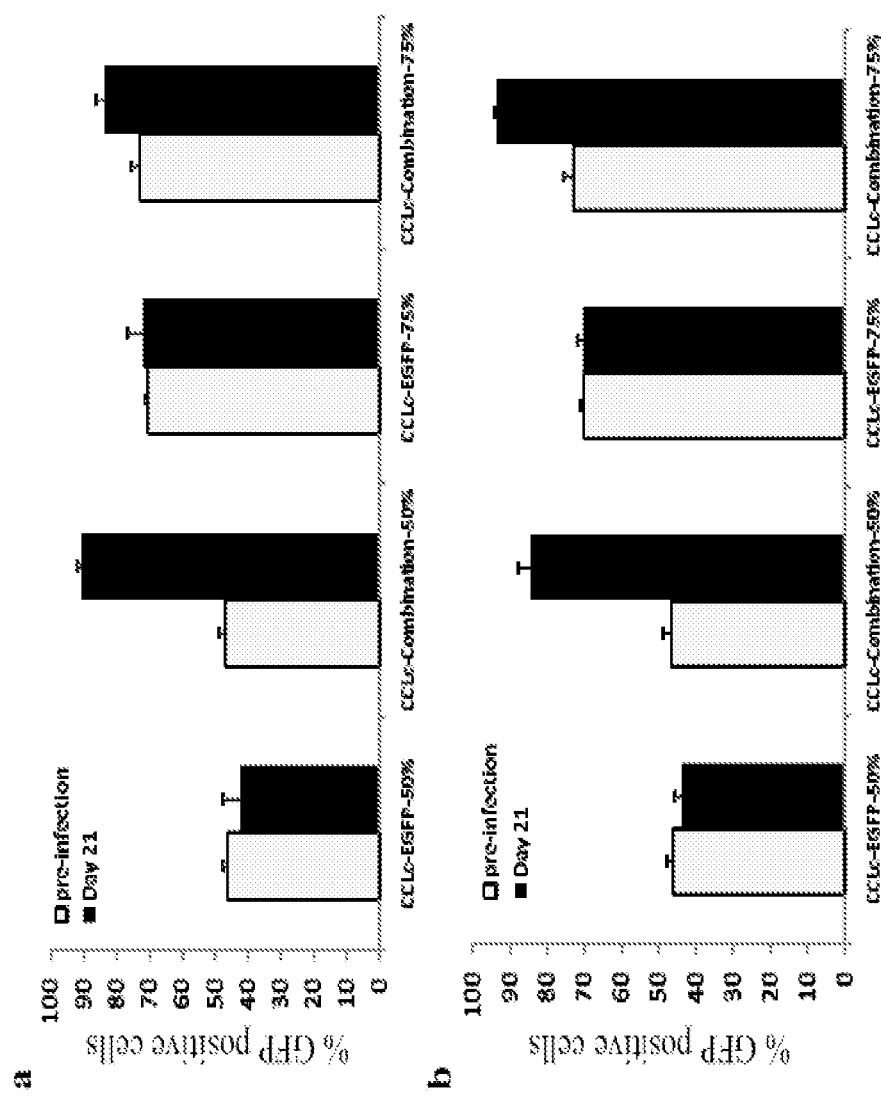
FIG. 13 shows a selective survival advantage of combination vector transduced cells: Ghost-R5-X4-R3 cells were transduced with the EGFP-alone or the combination lentiviral vector. Transduced cells were mixed with nontransduced cells at a ratio of 1:1 and 2:1 (transduced:nontransduced) and were challenged with the (a) R5-tropic BaL-1 or (b) X4-tropic strain of HIV-1 at an MOI of 0.01. Cells were analyzed by FACS for EGFP expression pre-infection and on day 21 post-infection.

It is expected that in a human clinical HIV gene therapy application, not all of an individual's HIV susceptible cells will be transduced with anti-HIV gene therapy vectors and will be capable of resisting viral infection and replication. Therefore, to evaluate the selective survival advantage of anti-HIV gene transduced cells, a mixed population of non-transduced and transduced cells, either EGFP-alone or combination vector transduced, were challenged with HIV-1, both BaL-1 and NL4-3. As seen in FIG. 13, a selective survival advantage was conferred and maintained in cultures containing the combination vector transduced cells demonstrated by an increase of the total percent EGFP positive cells by the end of the viral challenge. In cultures containing a 1:1 and 2:1 ratio of combination vector transduced cells to nontransduced cells, the pre-infection EGFP percentage being, ~46% and ~73% respectively, increased to >84% EGFP positive cells by day 21 post-infection for both BaL-1 (FIG. 13a) and NL4-3 (FIG. 13b). These results are in contrast to cultures containing EGFP-alone vector transduced cells where the EGFP percent positive cell population remained relatively constant on day 21 post-infection (~42% and ~72% for ratios of 1:1 and 2:1, respectively) compared to the pre-infection EGFP percentages of 46% and 70%. These results establish that the anti-HIV combination vector transduced cells were able to survive and increase in number during the course of the HIV-1 infection.

Figure 14:
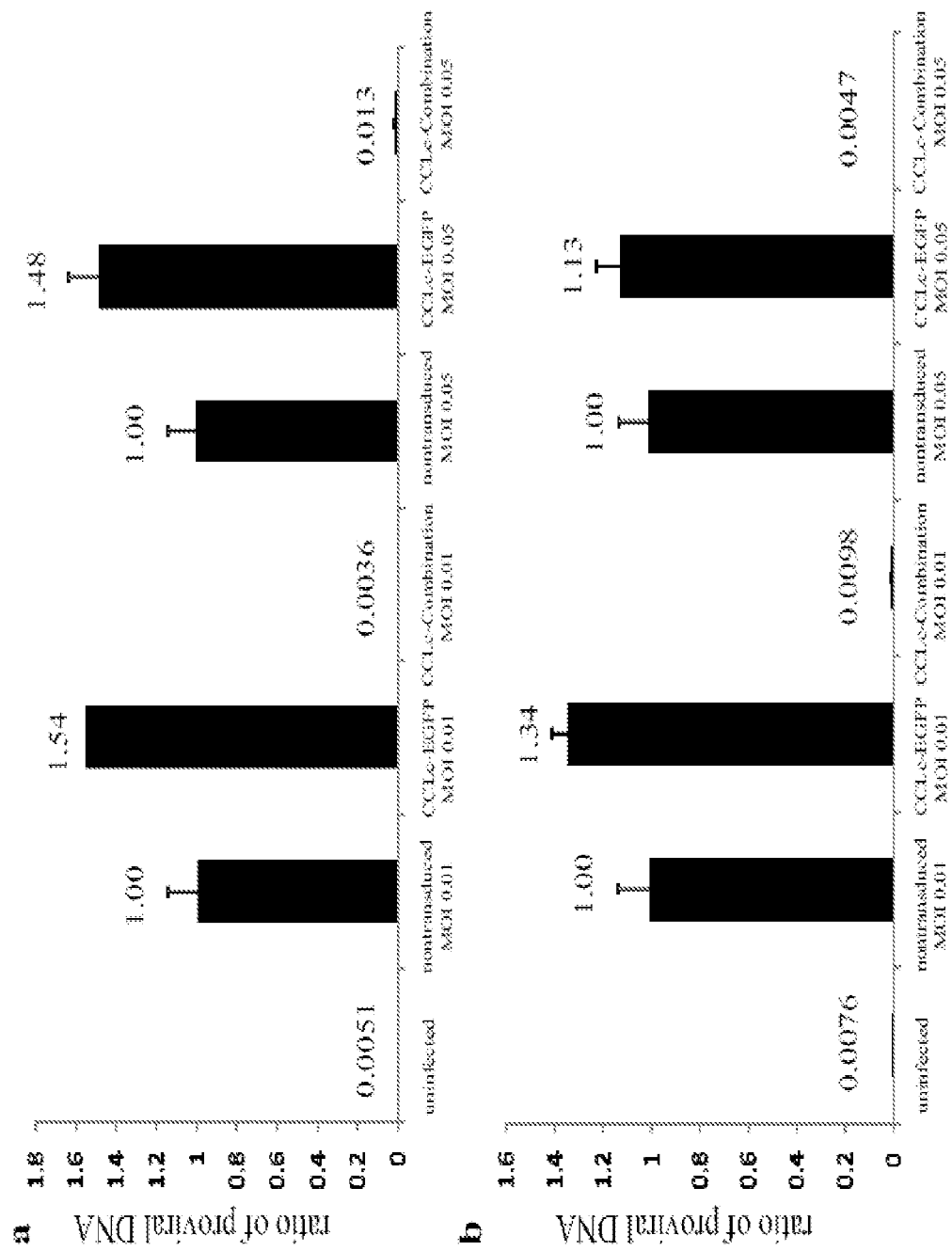
FIG. 14 shows detection of integrated HIV-1 provirus: Ghost-R5-X4-R3 nontransduced, EGFP-alone, and combination vector transduced cells were challenged with the (a) R5-tropic BaL-1 and (b) X4-tropic NL4-3 strain of HIV-1 at MOIs of 0.01 and 0.05. On day 25 post-infection, genomic DNA from virus challenged cells was analyzed by QRT-PCR for integrated HIV-1 provirus using primers specific for the pol gene.

Inhibition of HIV-1 Proviral Formation:

Viral reservoirs which are maintained in an HIV infected individual continue to be a major barrier for HIV eradication and curing patients with an established infection. To better eradicate the virus from infected individuals, the combination anti-HIV vector was designed to inhibit HIV-1 prior to integration, thus avoiding any provirus formation. To determine if viral inhibition was occurring at the stages of pre-entry (due to the CCR5 shRNA) and post-entry/pre-integration (due to TRIM5α), cells challenged with both BaL-1 and NL4-3 were further analyzed by QRT-PCR for genomic HIV-1 provirus. As seen in FIG. 14, a highly potent block of HIV-1 provirus formation could be demonstrated when genomic DNA from challenged cells (day 25 post-infection) was analyzed by QRT-PCR with primers specific for the HIV-1 pol gene. Combination vector transduced cells contained undetectable levels, similar to background levels in uninfected cells, of HIV-1 provirus as compared to control nontransduced and EGFP-alone vector transduced infected cells at MOIs of 0.01 and 0.05 for BaL-1 (FIG. 14*a*) and NL4-3 (FIG. 14*b*) strains of HIV-1. These data confirm that the combination vector, indeed, conferred a strong block to HIV-1 integration, therefore preventing HIV proviral DNA formation.

Figure 15:
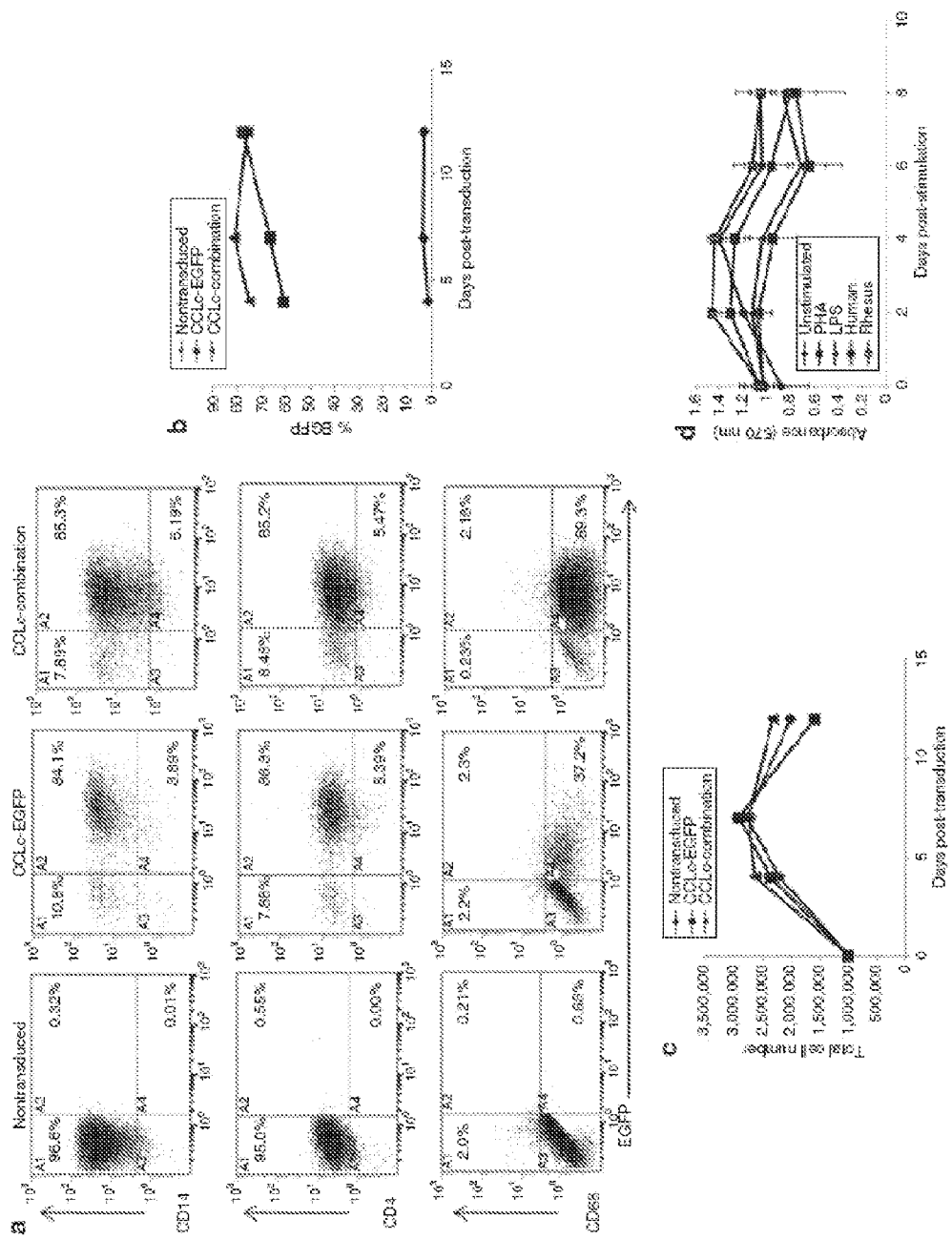
FIG. 15 depicts analysis to rule out possible adverse effects on progenitor cell proliferation and differentiation from combination vector transduction and expression of the anti-HIV transgenes: (a) CD34+ HPCs were transduced with the EGFP-alone or combination lentiviral vector and differentiated into mature macrophages. Cells were subsequently stained with the normal macrophage cell surface markers CD 14, CD4, and CD68 and analyzed by FACS. (b) Peripheral blood mononuclear cells (PBMCs) were transduced with the EGFP alone or combination vectors. On various post-transduction, the transduced cells were analyzed for EGFP expression by FACS or (c) total cell counts. (d) Monocytes and dendritic cells from fresh PBMCs were left unmanipulated or incubated with PHA, LPS, an 11-amino acid human peptide, or a 13-aa rhesus macaque peptide. Lymphocytes were added back to the culture and analyzed for various days for immune cell activation by the absorbance (570 nm) spectrum of MTT crystals formed from metabolically active cells.

Phenotypic Analysis of Transduced CD34+ HPC Derived Macrophages:

The introduction of foreign genes into cells has the potential to cause detrimental effects on their development. To evaluate whether lentiviral vector transduction of target cells and expression of the combination vector anti-HIV transgenes affected the differentiation of CD34+ HPCs into mature macrophages, cells were analyzed by FACS for macrophage specific cell surface markers. Combination vector transduced macrophages displayed normal levels of the surface markers CD14 (>93%), CD4 (>93%), and CD68 (an activation marker) (~2%) as compared to nontransduced and EGFP-alone transduced cells (FIG. 15*a*). Phenotypic analysis of these cells confirmed that normal differentiation had occurred from transduced CD34+ HPCs to mature macrophages and that transduced cells were indistinguishable from nontransduced cells.

Toxicity Studies of Vector-Transduced Cells

A previous report demonstrated that CCR5 shRNAs expressed by the U6 pol-III promoter were toxic to cells as compared to expression from the less robust H1 pol-III promoter.32 To evaluate the toxicity of the combination anti-HIV vector that contains a U6-expressed CCR5 shRNA, phytohemagglutinin-stimulated peripheral blood mononuclear cells (PBMCs) were either left nontransduced or transduced with the EGFP-alone or combination vectors. Cells were monitored on days 0, 4, 7, and 12 for both EGFP expression and total cell counts. Constant EGFP expression was observed for both the EGFP-alone and combination vector-transduced PBMCs throughout the experiment (FIG. 15*b*). Also, total cell counts were comparable between nontransduced, EGFP-alone-transduced, and combination vector-transduced PBMCs (FIG. 15*c*).

Detection of Immune Activation by the Chimeric TRIM5α Rhesus Macaque Amino Acid Sequence:

The expression of the chimeric TRIM5α isoform has the possibility of invoking an immune response due to the 13-aa patch from the rhesus macaque isoform which was inserted into the human isoform. To detect immune activation in response to presentation of the rhesus macaque 13-aa patch, an immune cell activation assay was performed. As displayed in FIG. 15*d*, no activation of immune cells had occurred in the samples which were pulsed with the rhesus macaque 13-aa peptide. The metabolic activity of the immune cells was similar to those observed in unmanipulated cells (day 6 P value=0.951 and day 8 P value=0.993) and the cell samples pulsed with the human 11-aa peptide (day 6 P value=0.938 and day 8 P value=0.419). However, activation of cells was observed in PHA and LPS stimulated cell samples as displayed by the decrease in total cell numbers. These results confirm that the rhesus macaque 13-aa patch located in the human/rhesus macaque chimeric TRIM5α isoform does not invoke immune cell activation when tested in a monocytes/dendritic cell culture system.

Experiment C—In Vivo Safety Data of a Combination Anti-HIV Lentiviral Vector

Human cord blood CD34+ hematopoietic progenitor cells were transduced with the combination anti-HIV lentiviral vector and transplanted into the humanized NOD/SCID-IL2 gamma receptor (NSG) knockout mouse model. After allowing 16 weeks for the mice and human cells to develop, the peripheral blood and lymphoid organs were analyzed by FACS for engraftment (EGFP+) of the anti-HIV gene modified human cells. EGFP+cells=anti-HIV gene modified cells. The data displayed in FIG. 17 demonstrates the in vivo safety of the combination anti-HIV lentiviral vector in an HIV stem cell gene therapy setting. Stem cells transduced with the vector were able to develop into mature human immune system cells and undergo normal distribution in the NSG mice.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

REFERENCES

1. Bacheler, L. T. et al. Human immunodeficiency virus type 1 mutations selected in patients failing efavirenz combination therapy. Antimicrob. Agents Chemother. 44, 2475-2484 (2000).
2. Martinez-Picado, J. et al. Antiretroviral resistance during successful therapy of HIV type 1 infection. Proc. Natl. Acad. Sci. USA. 97, 10948-10953 (2000).
3. Winters, M. A. et al. Frequency of antiretroviral drug resistance mutations in HIV-1 strains from patients failing triple drug regimens. The Terry Beirn Community Programs for Clinical Research on AIDS. Antivir. Ther. 5, 57-63 (2000).
4. Lafeuillade, A., Poggi, C., Hittinger, G. & Chadapaud, S. Phenotypic and genotypic resistance to nucleoside reverse transcriptase inhibitors in HIV-1 clinical isolates. HIV Med. 2, 231-235 (2002).
5. Marks, K. & Gulick, R. M. New antiretroviral agents for the treatment of HIV infection. Curr. HIV/AIDS Rep. 1, 82-88 (2004).
6. Barouch, D. H. Challenges in the development of an HIV-1 vaccine. Nature. 455, 613-619 (2008).
7. Rossi, J. J. The application of ribozymes to HIV infection. Curr. Opin. Mol. Ther. 1, 316-322 (1999).
8. Bai, J. et al. Characterization of Anti-CCR5 Ribozyme-Transduced CD34+ Hematopoietic Progenitor Cells in Vitro and in a SCID-hu Mouse Model in Vivo. Mol. Ther. 1, 244-254 (2002).
9. Ding, S. F., Lombardi, R., Nazari, R. & Joshi, S. A combination anti-HIV-1 gene therapy approach using a single transcription unit that expresses antisense, decoy, and sense RNAs, and transdominant negative mutant Gag and Env proteins. Front. Biosci. 7, a15-28 (2002).
10. Lee, N. S. et al. Expression of small interfering RNAs targeted against HIV-1 rev transcripts in human cells. Nat. Biotechnol. 20, 500-505 (2002).

11. Martinez, M. A. et al. Suppression of chemokine receptor expression by RNA interference allows for inhibition of HIV-1 replication. AIDS 16, 2385-2390 (2002).
12. Michienzi, A., Li, S., Zaia, J. A. & Rossi, J. J. A nucleolar TAR decoy inhibitor of HIV-1 replication. Proc. Natl. Acad. Sci. USA. 99, 14047-52 (2002).
13. Novina, C. D. et al. siRNA-directed inhibition of HIV-1 infection. Nat. Med. 8, 681-686 (2002).
14. Cordelier, P., Morse, B. & Strayer, D. S. Targeting CCR5 with siRNAs: using recombinant SV40-derived vectors to protect macrophages and microglia from R5-tropic HIV. Oligonucleotides 13, 281-294 (2003).
15. An, D. S. et al. Stable reduction of CCR5 by RNAi through hematopoietic stem cell transplant in non-human primates. Proc. Natl. Acad. Sci. USA. 104, 13110-13115 (2007).
16. Anderson, J. & Akkina, R. Complete knockdown of CCR5 by lentiviral vector-expressed siRNAs and protection of transgenic macrophages against HIV-1 infection. Gene Ther. 14, 1287-1297 (2007).
17. Kumar, P. et al. T cell-specific siRNA delivery suppresses HIV-1 infection in humanized mice. Cell 134, 577-586 (2008).
18. ter Brake, O. et al. Evaluation of safety and efficacy of RNAi against HIV-1 in the human immune system (Rag-2 (−/−)gammac(−/−)) mouse model. Gene Ther. 16, 148-153 (2009).
19. Kohn, D. B. et al. A clinical trial of retroviral-mediated transfer of a Rev-responsive element decoy gene into CD34+ cells from the bone marrow of human immunodeficiency virus-1-infected children. Blood 94, 368-371 (1999).
20. Bauer, G. et al. Gene therapy for pediatric AIDS. Ann. NY Acad. Sci. 918, 318-329 (2000).
21. Humeau, L. M. et al. Efficient lentiviral vector-mediated control of HIV-1 replication in CD4 lymphocytes from diverse HIV+ infected patients grouped according to CD4 count and viral load. Mol. Ther. 9, 902-13 (2004).
22. Anderson, J. et al. Safety and efficacy of a lentiviral vector containing three anti-HIV genes-CCR5 ribozyme, tat-rev siRNA, and TAR decoy-in SCID-hu mouse-derived T cells. Mol. Ther. 15, 1182-1188 (2007).
23. Mitsuyasu, R. T. et al. Phase 2 gene therapy trial of an anti-HIV ribozyme in autologous CD34+ cells. Nat. Med. 5, 285-292 (2009).
24. Fire, A. et al. Potent and specific genetic interference by double-stranded RNA in *Caenorhabditis elegans*. Nature 391, 806-811 (1998).
25. Elbashir, S. M. et al. Duplexes of 21-nucleotide RNAs mediate RNA interference in cultured mammalian cells. Nature 411, 494-498 (2001).
26. Huang, Y. et al. The role of a mutant CCR5 allele in HIV-1 transmission and disease progression. Nat. Med. 2, 1240-1243 (1996).
27. Liu, R. et al. Homozygous defect in HIV-1 coreceptor accounts for resistance of some multiply exposed individuals to HIV-1 infection. Cell 86, 267-377 (1996).
28. Naif, H. M. et al. A human immunodeficiency virus type 1 isolate from an infected person homozygous for CCR5Δ32 exhibits dual tropism by infecting macrophages and MT2 cells via CXCR4. J. Virol. 76, 3114-3124 (2002).
29. Hutter, G. et al. Long-Term Control of HIV by CCR5 Delta32/Delta32 Stem-Cell Transplantation. N. Engl. J. Med. 360, 692-698 (2009).
30. Hatziioannou, T., Delahaye, E., Martin, F., Russell, S. J. & Cosset, F-L. Retroviral Display of Functional Binding Domains Fused to the Amino Terminus of Influenza Hemagglutinin. Hum. Gene Ther. 10, 1533-1544 (1999).
31. Jiang, A. & Dornburg, R. In vivo cell type-specific gene delivery with retroviral vectors that display single chain antibodies. Gene Ther. 6, 1982-1987 (1999).
32. Engelstadter, M. et al. Targeted gene transfer to lymphocytes using murine leukaemia virus vectors pseudotyped with spleen necrosis virus envelope proteins. Gene Ther. 8, 1202-1206 (2001).
33. Lavillette, D., Russell, S. J. & Cosset, F-L. Retargeting gene delivery using surface-engineered retroviral vector particles. Curr. Opin. Biotechnol. 12, 461-466 (2001).
34. Lin, A. H. et al. Receptor-Specific Targeting Mediated by the Coexpression of a Targeted Murine Leukemia Virus Envelope Protein and a Binding-Defective Influenza Hemagglutinin Protein. Hum. Gene Ther. 12, 323-332 (2001).
35. Zhong, Q. et al. Efficient c-kit Receptor-Targeted Gene Transfer to Primary Human CD34-Selected Hematopoietic Stem Cells. J. Virol. 75, 10393-10400 (2001).
36. Maurice, M. et al. Efficient gene transfer into human primary blood lymphocytes by surface-engineered lentiviral vectors that display a T cell-activating polypeptide. Blood 99, 2342-2350 (2002).
37. Chandrashekran, A., Gordon, M. Y. & Casimir, C. Targeted retroviral transduction of c-kit+ hematopoietic cells using novel ligand display technology. Blood 104, 2697-2703 (2004).
38. Verhoeyen, E. et al. Novel lentiviral vectors displaying "early-acting cytokines" selectively promote survival and transduction of NOD/SCID repopulating human hematopoietic stem cells. Blood 106, 3386-3395 (2005).
39. Yang, L., Bailey, L., Baltimore, D. & Wang, P. Targeting lentiviral vectors to specific cell types in vivo. Proc. Natl. Acad. Sci. USA. 103, 11479-11484 (2006).
40. Yang, L. et al. Engineered lentivector targeting of dendritic cells for in vivo immunization. Nat. Biotechnol. 26, 326-334 (2008).
41. Silva, F. A. D., Costa, M. J. L., Corte-Real, S. & Goncalves, J. Celltype-specific targeting with Sindbis pseudotyped lentiviral vectors displaying anti-CCR5 single-chain antibodies. Hum. Gene Ther. 16, 223-234 (2005).
42. Bonyhadi M, Moss K, Voytovich A, Auten J, Kalfoglou C, Plavec I, et al. (1997). RevM10-expressing T cells derived in vivo from transduced human hematopoietic stem-progenitor cells inhibit human immunodeficiency virus replication. J Virol; 71: 4707-4716.
43. Anderson J, Akkina R (2008). Human immunodeficiency virus type 1 restriction by human-rhesus chimeric tripartite motif 5alpha (TRIM 5alpha) in CD34+(+) cell-derived macrophages in vitro and in T cells in vivo in severe combined immunodeficient (SCID-hu) mice transplanted with human fetal tissue. Hum Gene Ther; 19: 217-228.
44. Berger E A, Murphy P M, Farber J M (1999). Chemokine receptors as HIV-1 coreceptors: roles in viral entry, tropism, and disease. Annu Rev Immunol; 17: 657-700.
45. Stremlau M, Owens C M, Perron M J, Kiessling M, Autissier P, Sodroski J (2004). The cytoplasmic body component TRIM5alpha restricts HIV-1 infection in Old World monkeys. Nature; 427: 848-853.
46. Sawyer S L, Wu L I, Emerman M, Malik H S (2005). Positive selection of primate TRIM5alpha identifies a critical species-specific retroviral restriction domain. Proc Natl Acad Sci USA; 102: 2832-2837.
47. Castanotto D, Li H, Rossi J (2002). Functional siRNA expression from transfected PCR products. RNA; 8: 1454-1460.

48. Ohno, K., Sawai, K., Iijima, Y., Levin, B. & Meruelo, D. Cell-specific targeting of Sindbis virus vectors displaying IgG-binding domains of protein A. Nat. Biotechnol. 15, 763-767 (1997).
49. Morizono, K., Bristol, G., Xie, Y. M., Kung, S. K. & Chen, I. S. Antibody-directed targeting of retroviral vectors via cell surface antigens. J. Virol. 75, 8016-8020 (2001).
50. Iijima, Y. et al. Cell-specific targeting of a thymidine kinase/gancyclovir gene therapy system using a recombinant Sindbis virus vector. Int. J. Cancer. 80, 110-118 (1999).
51. Morizono, K. et al. Lentiviral vector retargeting to P-glycoprotein on metastatic melanoma through intravenous injection. Nat. Med. 11, 346-352 (2005).
52. Morizono, K. & Chen, I. S. Targeted gene delivery by intravenous injection of retroviral vectors. Cell Cycle 4, 854-856 (2005).
53. Liang, M., Pariente, N., Morizono, K. & Chen, I. S. Targeted transduction of CD34+ hematopoietic progenitor cells in nonpurified human mobilized peripheral blood mononuclear cells. J. Gene Med. 11, 185-196 (2009).

What is claimed is:

1. A lentiviral vector comprising:
   (a) a lentiviral backbone comprising SEQ ID NO. 18 or a polynucleotide having at least 80% sequence identity to SEQ ID NO: 18;
   (b) a nucleic acid encoding a CCR5 RNAi;
   (c) an expression control element that regulates expression of the nucleic acid encoding the RNAi of element (b).

2. The lentiviral vector of claim 1, wherein the expression control element is a promoter.

3. The lentiviral vector of claim 1, wherein the expression control element is a Polymerase-III promoter or a Polymerase II promoter.

4. The lentiviral vector of claim 2, wherein the expression control element is a Polymerase-III promoter.

5. The lentiviral vector of claim 4, wherein the Polymerase III promoter comprises the U6 promoter sequence of nucleotides 1-283 of SEQ ID NO: 11 or an equivalent thereof.

6. The lentiviral vector of claim 1, wherein the nucleic acid encoding an CCR5 RNAi comprises a CCR5 shRNA polynucleotide.

7. The lentiviral vector of claim 1, wherein the CCR5 RNAi is one or more of the group shRNA, siRNA, miRNA or dsRNA.

8. The lentiviral vector of claim 1, further comprising a nucleic acid encoding a reporter marker.

9. A lentiviral packaging system comprising:
   (a) the lentiviral vector of claim 1;
   (b) an packaging plasmid; and
   (c) an envelope plasmid.

10. The lentiviral packaging system of claim 9, wherein the envelope plasmid is a plasmid comprising a S. aureus ZZ domain sequence.

11. The lentiviral packaging system of claim 9 or 10, wherein the envelope plasmid comprises the polynucleotide shown in SEQ ID NO: 26 or an equivalent thereto.

12. The lentiviral packaging system of claim 9, further comprising (d) a packaging cell line.

13. The lentiviral packaging system of claim 12, wherein the packaging cell line is HEK-293 cell.

14. A method for producing a pseudotyped lentiviral particle, comprising transducing a packaging cell line with the system of claim 9 under conditions suitable to package the lentiviral vector.

15. The method of claim 14, wherein the packaging cell line is HEK-293.

16. An isolated pseudotyped lentiviral particle produced by the method of claim 14 or 15.

17. An isolated host cell comprising the lentiviral vector of claim 1.

18. The isolated host cell of claim 17, wherein the isolated host cell is a stem cell.

19. The pseudotyped lentiviral particle of claim 16, conjugated to one or more antibody that may be the same or different.

20. A method to inhibit HIV replication in a cell infected with HIV, comprising contacting the cell with an effective amount of the pseudotyped lentiviral particle of claim 16.

21. A method to inhibit HIV replication in a subject, comprising administering to the subject in need thereof an effective amount of pseudotyped lentiviral particle of claim 16.

22. A lentiviral vector comprising:
   (a) a lentiviral backbone comprising SEQ ID NO. 18 or a polynucleotide having at least 80% identity thereto;
   (b) a nucleic acid encoding a CCR5 RNAi;
   (c) a nucleic acid encoding a TRIM5alpha sequence;
   (d) a nucleic acid encoding an HIV TAR sequence; and
   (e) one or more expression control elements that separately regulate expression of the nucleic acid encoding the elements (b), (c) and (d).

23. The lentiviral vector of claim 22, wherein at least one of the expression control elements is a promoter.

24. The lentiviral vector of claim 22, wherein the one or more expression control element is a Polymerase-III promoter or a Polymerase II promoter that regulates expression of the CCR5 RNAi or the HIV TAR sequence.

25. The lentiviral vector of claim 22, wherein the one or more expression control element is a Polymerase II promoter that regulates expression of the nucleic acid encoding the TRIM5alpha sequence.

26. The lentiviral vector of claim 22, wherein the Polymerase-III promoter comprises the U6 promoter sequence or an equivalent thereof.

27. The lentiviral vector of claim 22, wherein the Polymerase II promoter comprises the MNDU3 Polymerase-II promoter or an equivalent thereof.

28. The lentiviral vector of claim 22, wherein CCR5 RNAi is one or more of the group shRNA, siRNA, miRNA or dsRNA.

29. The lentiviral vector of claim 22, wherein the nucleic acid encoding an CCR5 RNAi comprises CCR5 shRNA.

30. The lentiviral vector of claim 22, wherein the nucleic acid encoding the TRIM5alpha sequences comprises the polynucleotide shown in SEQ ID NO: 17 or an equivalent thereof.

31. The lentiviral vector of claim 22, wherein the nucleic acid encoding the TAR sequence comprises the TAR decoy polynucleotide of SEQ ID NO: 19 or an equivalent thereof.

32. The lentiviral vector of claim 22, further comprising a nucleic acid encoding a reporter marker.

33. A lentiviral packaging system comprising:
   (a) the lentiviral vector of claim 22;
   (b) a packaging plasmid; and
   (c) an envelope plasmid.

34. The lentiviral packaging system of claim 33, wherein the envelope plasmid is a plasmid comprising S. aureus ZZ domain sequence.

35. The lentiviral system of claim 33 or 34, wherein the envelope plasmid comprises the polynucleotide shown in SEQ ID NO: 26 or an equivalent thereof.

36. The lentiviral system of claim 33, further comprising (d) a packaging cell line.

37. The lentiviral system of claim 36, wherein the packaging cell line is HEK-293 cell.

38. A method for producing a pseudotyped lentiviral particle, comprising transducing a packaging cell line with the system of claim 33 under conditions suitable to package the lentiviral vector.

39. The method of claim 38, wherein the packaging cell line is HEK-293.

40. The method of claim 38 or 39, further comprising isolating the pseudotyped lentiviral particle.

41. A pseudotyped lentiviral particle produced by the method of claim 40.

42. An isolated cell conjugated to the pseudotyped lentiviral particle of claim 41.

43. A method to inhibit HIV replication in a cell infected with HIV, comprising contacting the cell with an effective amount of the cell of the pseudotyped lentiviral vector particle of claim 41.

44. A method to inhibit HIV replication, comprising administering to a subject in need thereof an effective amount of the pseudotyped lentiviral vector particle of claim 41.

45. A method to prevent HIV replication, comprising administering to a subject in need thereof an effective amount of the pseudotyped lentiviral vector particle of claim 41.

46. The method of claim 45, wherein the contacting is in vitro or in vivo.

47. A method to treat an HIV infection in a subject in need thereof, comprising administering to the subject an effective amount of the pseudotyped lentiviral vector particle of claim 41.

48. A method to treat an HIV infection in a subject in need thereof, comprising administering to the subject an effective amount of the cell of claim 18.

\* \* \* \* \*

SEQUENCE LISTING

<160> NUMBER OF SEQ ID NOS: 26

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgacttaaaa tcgctagcca gatctgagcc tgggagctct ctggctag                48

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggtctctct ggttagacca gatttgagcc tgggagctct ctggctaact agggaaccc   59

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgaagcttg atcccgtttg ccggtcgatc gcttcga                           37

<210> SEQ ID NO 4
<211> LENGTH: 11
<212> TYPE: PRT
<213> ORGANISM: Homo sapiens

<400> SEQUENCE: 4

Gly Ala Arg Gly Thr Arg Tyr Gln Thr Phe Val
1               5                   10

<210> SEQ ID NO 5
<211> LENGTH: 13
<212> TYPE: PRT
<213> ORGANISM: Macaca mulatta

<400> SEQUENCE: 5

Gln Ala Pro Gly Thr Leu Phe Thr Phe Pro Ser Leu Thr
1               5                   10

-continued

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actgcaaaag gctgaagagc                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcatagtga gcccagaagg                                                 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctggctacta tttcttttgc ta                                              22

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggcatgggt accagcaca                                                  19

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tttatctact tgttcatttc ctccaattcc tt                                   32

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
agatccagtt tggggatcca aggtcgggca ggaagagggc ctatttccca tgattccttc     60
atatttgcat atacgataca aggctgttag agagataatt agaattaatt tgactgtaaa   120
cacaaagata ttagtacaaa atacgtgacg tagaaagtaa taatttcttg ggtagtttgc   180
```

```
agttttaaaa ttatgtttta aaatggacta tcatatgctt accgtaacct gaaagtattt        240
cgatttcttg gctttatata tcttgtggaa aggacgaaac accgagcatg actgacatct        300
acttcaagag agtagatgtc agtcatgctc tttttt                                  336
```

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12

```
gtgtcaagtc caatctatga catcaattat atgtgaattg atgtcataga ttggacttga        60
cac                                                                       63
```

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13

```
gttcagaaac tacctcttaa tatgtgtaag aggtagtttc tgaac                         45
```

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14

```
gttcagaaac tacctcttag tcttcttcat atgtggaaga agactaagag gtagtttctg        60
aac                                                                       63
```

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15

```
gagcatgact gacatctacc tgctcaacat atgtggttga gcaggtagat gtcagtcatg        60
ctc                                                                       63
```

<210> SEQ ID NO 16
<211> LENGTH: 324
<212> TYPE: DNA
<213> ORGANISM: Homo sapiens

<400> SEQUENCE: 16

```
gacatccaga tgacccagtc tccatcctcc ctgtctgcat ctgtaggaga cagagtcacc        60
atcacttgcc aggcgagtca gggcattcgc aaatatttaa attggtatca gcaaaaacca       120
gggaaagtcc ctaagctcct gatctacgat gcatccaatt tggaaacagg ggtcccatca       180
aggttcagtg gaagtggatc agggacagat tttactttcg ccatcagcag cctgcagccg       240
```

```
gaagatactg caacatatta ctgtcaacaa tatgatgatt tccccttcac cttcggccag      300
gggacacgac tggagattaa acgt                                             324
```

<210> SEQ ID NO 17
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gctactatgg cttctggaat cctggttaat gtaaaggagg aggtgacctg ccccatctgc       60
ctggaactcc tgacacaacc cctgagcctg gactgcggcc acagcttctg ccaagcatgc      120
ctcactgcaa accacaagaa gtccatgcta gacaaaggag agagtagctg ccctgtgtgc      180
cggatcagtt accagcctga gaacatacgg cctaatcggc atgtagccaa catagtggag      240
aagctcaggg aggtcaagtt gagcccagag gggcagaaag ttgatcattg tgcacgccat      300
ggagagaaac ttctactctt ctgtcaggag gacgggaagg tcatttgctg gctttgtgag      360
cggtctcagg agcaccgtgg tcaccacacg ttcctcacag aggaggttgc ccgggagtac      420
caagtgaagc tccaggcagc tctggagatg ctgaggcaga agcagcagga agctgaagag      480
ttagaagctg acatcagaga agagaaagct tcctggaaga ctcaaataca gtatgacaaa      540
accaacgtct tggcagattt tgagcaactg agagacatcc tggactggga ggagagcaat      600
gagctgcaaa acctggagaa ggaggaggaa gacattctga aaagccttac gaactctgaa      660
actgagatgg tgcagcagac ccagtccctg agagagctca tctcagatct ggagcatcgg      720
ctgcaggggt cagtgatgga gctgcttcag ggtgtggatg gcgtcataaa aaggacggag      780
aacgtgacct tgaagaagcc agaaactttt ccaaaaaatc aaaggagagt gtttcgagct      840
cctgatctga aggaatgctc agaagtgttt agagagctga cagatgtccg acgctactgg      900
gttgatgtga cagtggctcc aaacaacatt tcatgtgctg tcatttctga agataagaga      960
caagtgagct ctccgaaacc acagataata tcaggcac cagggacatt atttacgttt      1020
ccgtcactca cgaatttcaa ttattgtact ggcatcctgg gctctcaaag tatcacatca      1080
gggaaacatt actgggaggt agacgtgtcc aagaaaactg cttggatcct gggggtatgt      1140
gctggcttcc aacctgatgc aatgtgtaat attgaaaaaa atgaaaatta tcaacctaaa      1200
tacggctact gggttatagg gttagaggaa ggagttaaat gtagtgcttt ccaggatagt      1260
tccttccata ctccttctgt tcctttcatt gtgcccctct ctgtgattat ttgtcctgat      1320
cgtgttggag ttttcctaga ctatgaggct tgcactgtct cattcttcaa tatcacaaac      1380
catggattct tcatctataa gttttctcac tgttcttttt ctcagcctgt atttccatat      1440
ttaaatccta gaaatgtgg agtccccatg actctgtgct caccaagctc tggcggctac      1500
ccatacgacg tcccagacta cgcttgagcc tga                                  1533
```

<210> SEQ ID NO 18
<211> LENGTH: 7865
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
caggtggcac ttttcgggga aatgtgcgcg gaaccctat ttgtttattt ttctaaatac        60
```

```
attcaaatat gtatccgctc atgagacaat aaccctgata aatgcttcaa taatattgaa    120
aaaggaagag tatgagtatt caacatttcc gtgtcgccct tattccctttt tttgcggcat   180 tttgccttcc tgttttttgct cacccagaaa cgctggtgaa agtaaaagat gctgaagatc   240
agttgggtgc acgagtgggt tacatcgaac tggatctcaa cagcggtaag atccttgaga   300
gttttcgccc cgaagaacgt tttccaatga tgagcacttt taaagttctg ctatgtggcg   360
cggtattatc ccgtattgac gccgggcaag agcaactcgg tcgccgcata cactattctc   420
agaatgactt ggttgagtac tcaccagtca cagaaaagca tcttacggat ggcatgacag   480
taagagaatt atgcagtgct gccataacca tgagtgataa cactgcggcc aacttacttc   540
tgacaacgat cggaggaccg aaggagctaa ccgcttttttt gcaacaacatg ggggatcatg   600 taactcgcct tgatcgttgg gaaccggagc tgaatgaagc cataccaaac gacgagcgtg   660
acaccacgat gcctgtagca atggcaacaa cgttgcgcaa actattaact ggcgaactac   720
ttactctagc ttcccggcaa caattaatag actggatgga ggcggataaa gttgcaggac   780
cacttctgcg ctcggccctt ccggctggct ggtttattgc tgataaatct ggagccggtg   840
agcgtgggtc tcgcggtatc attgcagcac tggggccaga tggtaagccc tcccgtatcg   900
tagttatcta cacgacgggg agtcaggcaa ctatggatga acgaaataga cagatcgctg   960
agataggtgc ctcactgatt aagcattggt aactgtcaga ccaagtttac tcatatatac   1020
tttagattga tttaaaactt cattttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc cttttttttct gcgcgtaatc tgctgcttgc   1200
aaacaaaaaa accaccgcta ccagcggtgg tttgtttgcc ggatcaagag ctaccaactc   1260 ttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt cgtgcacac   1500 agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca gggggggcgga   1740 gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
```

-continued

```
cgccaatagg gactttccat tgacgtcaat gggtggagta tttacggtaa actgcccact    2520
tggcagtaca tcaagtgtat catatgccaa gtacgccccc tattgacgtc aatgacggta    2580
aatggcccgc ctggcattat gcccagtaca tgaccttatg ggactttcct acttggcagt    2640
acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa aatcaacggg actttccaaa atgtcgtaac aactccgccc    2820
cattgacgca aatgggcggt aggcgtgtac ggtgggaggt ctatataagc agagctcgtt    2880
tagtgaaccg ggtctctct ggttagacca gatctgagcc tgggagctct ctggctaact    2940
agggaaccca ctgcttaagc ctcaataaag cttgccttga gtgcttcaag tagtgtgtgc    3000
ccgtctgttg tgtgactctg gtaactagag atccctcaga ccctttagt cagtgtggaa    3060 aatctctagc agtggcgccc gaacaggggac ctgaaagcga agggaaacc agaggagctc    3120 tctcgacgca ggactcggct tgctgaagcg cgcacggcaa gaggcgaggg gcggcgactg    3180
gtgagtacgc caaaaatttt gactagcgga ggctagaagg agagagatgg gtgcgagagc    3240
gtcagtatta agcggggggag aattagatcg cgatgggaaa aaattcggtt aaggccaggg    3300
ggaaagaaaa aatataaatt aaaacatata gtatgggcaa gcagggagct agaacgattc    3360
gcagttaatc ctggcctgtt agaaacatca gaaggctgta gacaaatact gggacagcta    3420
caaccatccc ttcagacagg atcagaagaa cttagatcat tatataatac agtagcaacc    3480
ctctattgtg tgcatcaaag gatagagata aaagacacca aggaagcttt agacaagata    3540
gaggaagagc aaaacaaaag taagaccacc gcacagcaag cggccgctga tcttcagacc    3600
tggaggagga gatatgaggg acaattggag aagtgaatta tataaatata aagtagtaaa    3660
aattgaacca ttaggagtag cacccaccaa ggcaaagaga agagtggtgc agagagaaaa    3720
aagagcagtg ggaataggag cttttgttcct tgggttcttg ggagcagcag gaagcactat    3780
gggcgcagcc tcaatgacgc tgacggtaca ggccagacaa ttattgtctg gtatagtgca    3840
gcagcagaac aatttgctga gggctattga ggcgcaacag catctgttgc aactcacagt    3900
ctggggcatc aagcagctcc aggcaagaat cctggctgtg gaaagatacc taaaggatca    3960
acagctcctg gggatttggg gttgctctgg aaaactcatt tgcaccactg ctgtgccttg    4020
gaatgctagt tggagtaata atctctggaa acagattgga atcacacgac ctggatggag    4080
tgggacagag aaaattaaca attacacaag cttaatacact ccttaattga agaatcgcaa    4140
aaccagcaag aaaagaatga acaagaatta ttggaattag ataaatgggc aagtttgtgg    4200
aattggttta acataacaaa ttggctgtgg tatataaaat tattcataat gatagtagga    4260
ggcttggtag gtttaagaat agttttttgct gtactttcta tagtgaatag agttaggcag    4320
ggatattcac cattatcgtt tcagacccac ctcccaaccc cgaggggacc cgacaggccc    4380
gaaggaatag aagaagaagg tggagagaga cacagagaca gatccattcg attagtgaac    4440
ggatctcgac ggtatcgata agctaattca caaatggcag tattcatcca caattttaaa    4500
agaaaagggg ggattggggg gtacagtgca ggggaaagaa tagtagacat aatagcaaca    4560
gacatacaaa ctaaagaatt acaaaaacaa attacaaaaa ttcaaaattt tcgggtttat    4620
tacagggaca gcagagatcc agtttgggaa ttagcttgat cgattagtcc aatttgttaa    4680
agacaggata tcagtggtcc aggctctagt tttgactcaa caatatcacc agctgaagcc    4740
tatagagtac gagccataga tagaataaaa gatttatttt agtctccaga aaaggggggg    4800
aatgaaagac cccacctgta ggtttggcaa gctaggatca aggttaggaa cagagagaca    4860
```

```
gcagaatatg ggccaaacag atatctgtg gtaagcagtt cctgcccgg ctcagggcca    4920 agaacagttg gaacagcaga atatgggcca acaggatat ctgtggtaag cagttcctgc    4980
cccggctcag ggccaagaac agatggtccc cagatgcggt cccgcccctca gcagtttcta    5040 gagaaccatc agatgtttcc agggtgcccc aaggacctga aatgaccctg tgccttattt    5100
gaactaacca atcagttcgc ttctcgcttc tgttcgcgcg cttctgctcc ccgagctcaa    5160
taaaagagcc cacaacccct cactcggcgc gatctagatc tcgaatcgaa ttctaccggg    5220 tagggaggc gcttttccca aggcagtctg gagcatgcgc tttagcagcc ccgctggcac    5280
ttggcgctac acaagtggcc tctggcctcg cacacattcc acatccaccg gtaggcgcca    5340
accggctccg ttcttggtg gcccttcgc gccaccttct actcctcccc tagtcaggaa    5400 gttcccccc gccccgcagc tcgcgtcgtg caggacgtga caaatggaag tagcacgtct    5460
cactagtctc gtgcagatgg acagcaccgc tgagcaatgg aagcgggtag gcctttgggg    5520
cagcggccaa tagcagcttt gctccttcgc tttctgggct cagaggctgg gaaggggtgg    5580 gtccggggc gggctcaggg gcgggctcag gggcggggcg ggcgcccgaa ggtcctccgg    5640
aggcccggca ttctcgcacg cttcaaaagc gcacgtctgc cgcgctgttc tcctcttcct    5700
catctccggg cctttcgacc atctagatcc accggtcgcc accatggtga gcaagggcga    5760
ggagctgttc accggggtgg tgcccatcct ggtcgagctg gacggcgacg taaacgccca    5820
caagttcagc gtgtccggcg agggcgaggg cgatgccacc tacggcaagc tgaccctgaa    5880
gttcatctgc accaccggca agctgcccgt gccctggccc accctcgtga ccaccctgac    5940
ctacggcgtg cagtgcttca gccgctaccc cgaccacatg aagcagcacg acttcttcaa    6000
gtccgccatg cccgaaggct acgtccagga gcgcaccatc ttcttcaagg acgacggcaa    6060
ctacaagacc cgcgccgagg tgaagttcga gggcgacacc ctggtgaacc gcatcgagct    6120
gaagggcatc gacttcaagg aggacggcaa catcctgggg cacaagctgg agtacaacta    6180
caacagccac aacgtctata tcatggccga caagcagaag aacggcatca aggtgaactt    6240
caagatccgc cacaacatcg aggacggcag cgtgcagctc gccgaccact accagcagaa    6300
cacccccatc ggcgacggcc ccgtgctgct gcccgacaac cactacctga gcacccagtc    6360
cgccctgagc aaagacccca acgagaagcg cgatcacatg gtcctgctgg agttcgtgac    6420
cgccgccggg atcactctcg gcatggacga gctgtacaag taaagcggcc aactcgaggg    6480
atcccccggg gtcgactgat caaattcgag ctcggtacct ttaagaccaa tgacttacaa    6540
ggcagctgta gatcttagcc acttttaaa agaaaagggg gactggaag ggctaattca    6600 ctcccaacga agacaagatc tgcttttgc ttgtactggg tctctctggt tagaccagat    6660
ctgagcctgg gagctctctg gctaactagg gaacccactg cttaagcctc aataaagctt    6720
gccttgagtg cttcaagtag tgtgtgcccg tctgttgtgt gactctggta actagagatc    6780
cctcagaccc ttttagtcag tgtggaaaat ctctagcagt agtagttcat gtcatcttat    6840
tattcagtat ttataacttg caaagaaatg aatatcagag agtgagagga acttgtttat    6900
tgcagcttat aatggttaca aataaagcaa tagcatcaca aatttcacaa ataaagcatt    6960
tttttcactg cattctagtt gtggtttgtc caaactcatc aatgtatctt atcatgtctg    7020
gctctagcta tcccgcccct aactccgccc atccgcccc taactccgcc cagttccgcc    7080
cattctccgc cccatggctg actaattttt tttatttatg cagaggccga ggccgcctcg    7140
gcctctgagc tattccagaa gtagtgagga ggcttttttg gaggcctagg cttttgcgtc    7200
gagacgtacc caattcgccc tatagtgagt cgtattacgc gcgctcactg gccgtcgttt    7260
```

```
tacaacgtcg tgactgggaa aaccctggcg ttacccaact taatcgcctt gcagcacatc    7320
cccctttcgc cagctggcgt aatagcgaag aggcccgcac cgatcgccct tcccaacagt    7380
tgcgcagcct gaatggcgaa tggcgcgacg cgcctgtag cggcgcatta agcgcggcgg     7440
gtgtggtggt tacgcgcagc gtgaccgcta cacttgccag cgccctagcg cccgctcctt    7500
tcgctttctt cccttccttt ctcgccacgt tcgccggctt tccccgtcaa gctctaaatc    7560
gggggctccc tttagggttc cgatttagtg ctttacggca cctcgacccc aaaaaacttg    7620
attagggtga tggttcacgt agtgggccat cgccctgata cacggttttt cgccctttga    7680
cgttggagtc cacgttcttt aatagtggac tcttgttcca aactggaaca cactcaacc    7740 ctatctcggt ctattctttt gatttataag ggattttgcc gatttcggcc tattggttaa    7800
aaaatgagct gatttaacaa aaatttaacg cgaattttaa caaatatta acgtttacaa     7860 tttcc                                                                 7865

<210> SEQ ID NO 19
<211> LENGTH: 421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
agatccagtt tggggatcca aggtcgggca ggaagagggc ctatttccca tgattccttc      60
atatttgcat atacgataca aggctgttag agagataatt agaattaatt tgactgtaaa    120
cacaaagata ttagtacaaa atacgtgacg tagaaagtaa taatttcttg ggtagtttgc    180
agttttaaaa ttatgtttta aaatggacta tcatatgctt accgtaactt gaaagtattt    240
cgatttcttg gctttatata tcttgtggaa aggacgaaac accgtcgacc ttgcaatgat    300
gtcgtaattt gcgtcttact ctgttctcag cgacagccag atctgagcct gggagctctc    360
tggctgtcag taagctggta cagaaggttg acgaaaattc ttactgagca agaaattttt    420
t                                                                    421

<210> SEQ ID NO 20
<211> LENGTH: 12061
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3044)..(3044)
<223> OTHER INFORMATION: a, c, t, g, unknown or other
<220> FEATURE:
<221> NAME/KEY: modified_base
<222> LOCATION: (3054)..(3054)
<223> OTHER INFORMATION: a, c, t, g, unknown or other
<220> FEATURE:
<221> NAME/KEY: modified_base
<222> LOCATION: (3060)..(3060)
<223> OTHER INFORMATION: a, c, t, g, unknown or other
<220> FEATURE:
<221> NAME/KEY: modified_base
<222> LOCATION: (3088)..(3088)
<223> OTHER INFORMATION: a, c, t, g, unknown or other
<220> FEATURE:
<221> NAME/KEY: modified_base
<222> LOCATION: (4213)..(4213)
<223> OTHER INFORMATION: a, c, t, g, unknown or other
<220> FEATURE:
<221> NAME/KEY: modified_base
```

```
<222> LOCATION: (5850)..(5850)
<223> OTHER INFORMATION: a, c, t, g, unknown or other
<220> FEATURE:
<221> NAME/KEY: modified_base
<222> LOCATION: (7167)..(7167)
<223> OTHER INFORMATION: a, c, t, g, unknown or other
<220> FEATURE:
<221> NAME/KEY: modified_base
<222> LOCATION: (7370)..(7370)
<223> OTHER INFORMATION: a, c, t, g, unknown or other
<220> FEATURE:
<221> NAME/KEY: modified_base
<222> LOCATION: (7850)..(7851)
<223> OTHER INFORMATION: a, c, t, g, unknown or other

<400> SEQUENCE: 20
taattcgagc tcgcccgaca ttgattattg actagttatt aatagtaatc aattacgggg      60
tcattagttc atagcccata tatggagttc cgcgttacat aacttacggt aaatggcccg     120
cctggctgac cgcccaacga cccccgccca ttgacgtcaa taatgacgta tgttcccata     180
gtaacgccaa tagggacttt ccattgacgt caatgggtgg agtatttacg gtaaactgcc     240
cacttggcag tacatcaagt gtatcatatg ccaagtacgc cccctattga cgtcaatgac     300
ggtaaatggc ccgcctggca ttatgcccag tacatgacct tatgggactt tcctacttgg     360
cagtacatct acgtattagt catcgctatt accatggtga tgcggttttg gcagtacatc     420
aatgggcgtg atagcggttt gactcacggg gattccaag tctcacccca ttgacgtcaa     480
tgggagtttg ttttggcacc aaaatcaacg ggactttcca aatgtcgta caactccgc     540
cccattgacg caaatgggcg gtaggcgtgt acggtgggag gtctatataa gcagagctcg     600
tttagtgaac cgtcagatcg cctggagacg ccatccacgc tgttttgacc tccatagaag     660
acaccgggac cgatcctagc ctccgcggcc gggaacggtg cattggaacg cggattcccc     720
gtgccaagag tgacgtaagt accgcctata gagtctatag gcccaccccc ttggcttctt     780
atgcgacgga tcgatcccgt aataagcttc gaggtccgcg gccggccgcg ttgacgcgca     840
cggcagaggc gatggggctg cgactggtg agagatgggt gcgagagcgt cagtattaag     900
cgggggagaa ttagatcgat gggaaaaaat tcggttaagg ccaggggaa agaaaaaata     960
taaattaaaa catatagtat gggcaagcag ggagctagaa cgattcgcag ttaatcctgg    1020
cctgttagaa acatcagaag gctgtagaca atactgggga cagctacaac catcccttca    1080
gacaggatca gaagaactta gatcattata taatacagta gcaaccctct attgtgtgca    1140
tcaaaggata gagataaaag acaccaagga agctttagac aagatagagg aagagcaaaa    1200
caaaagtaag aaaaaagcac agcaagcagc agctgacaca ggacacagca atcaggtcag    1260
ccaaaattac cctatagtgc agaacatcca ggggcaaatg gtacatcagg ccatatcacc    1320
tagaacttta aatgcatggg taaaagtagt agaagagaag gctttcagcc cagaagtgat    1380
acccatgttt tcagcattat cagaaggagc caccccacaa gatttaaaca ccatgctaac    1440
acagtggggg gacatcaagc agccatgcaa atgttaaaag agaccatcaa tgaggaagct    1500
gcagaatggg atagagtgca tccagtgcat gcagggccta ttgcaccagg ccagatgaga    1560
gaaccaaggg gaagtgacat agcaggaact actagtaccc ttcaggaaca aataggatgg    1620
atgacacata atccacctat cccagtagga gaaatctata aaagatggat aatcctggga    1680
ttaaataaaa tagtaagaat gtatagccct accagcattc tggacataag acaaggacca    1740
aaggaaccct ttagagacta tgtagaccga ttctataaaa ctctaagagc cgagcaagct    1800
tcacaagagg taaaaaattg gatgacagaa accttgttgg tccaaaatgc gaacccagat    1860
tgtaagacta ttttaaaagc attgggacca ggagcgacac tagaagaaat gatgacagca    1920
```

```
tgtcagggag tgggggggacc cggccataaa gcaagagttt tggctgaagc aatgagccaa    1980
gtaacaaatc cagctaccat aatgatacag aaaggcaatt ttaggaacca agaaaagact    2040
gttaagtgtt tcaattgtgg caaagaaggg cacatagcca aaaattgcag ggcccctagg    2100
aaaagggctg ttggaaatgt ggaaaggaag gacacccaat gaaagattgt actgagagac    2160
aggctatttt ttagggaaga tctggccttc cacaggaagg gccagggaat tttcttcaga    2220
gcagaccaga gccaacagcc ccaccagaag agagcttcag gtttgggaa gagacaacaa     2280 ctccctctca gaagcaggag ccgatagaca aggaactgtg tcctttagct tccctcagat    2340
cactctttgg cagcgacccc tcgtcacaat aaagatagg gggcaattaa aggaagctct    2400
attagataca ggagcagatg atacagtatt agaagaaatg aatttgccag gaagatggaa    2460
accaaaaatg ataggggaa ttggaggttt tatcaaagta ggacagtatg atcagatact    2520
catagaaatc tgcggacata aagctatagg tacagtatta gtaggaccta cacctgtcaa    2580
cataattgga agaaatctgt tgactcagat tggctgcact ttaaattttc ccattagtcc    2640
tattgagact gtaccagtaa aattaaagcc aggaatggat ggcccaaaag ttaaacaatg    2700
gccattgaca gaagaaaaaa taaaagcatt agtagaaatt tgtacagaaa tggaaaagga    2760
aggaaaaatt tcaaaaattg ggcctgaaaa tccatacaat actccagtat ttgccataaa    2820
gaaaaaagac agtactaaat ggagaaaatt agtagatttc agagaactta ataagagaac    2880
tcaagatttc tgggaagttc aattaggaat accacatcct gcagggttaa aacagaaaaa    2940
atcagtaaca gtactggatg tgggcgatgc atattttca gttcccttag ataaagactt    3000
caggaagtat actgcattta ccatacctag tataaacaat gagnacacca gggnattagn    3060
atatcagtac aatgtgcttc cacagggnat ggaaaggatc accagcaata ttccagtgta    3120
gcatgacaaa atcttagag cctttagaa aacaaaatcc agacatagtc atctatcaat      3180
acatggatga tttgtatgta ggatctgact tagaaataggg gcagcataga acaaaaatag    3240
aggaactgag acaacatctg ttgaggtggg gatttaccac accagacaaa aaacatcaga    3300
aagaacctcc attcctttgg atgggttatg aactccatcc tgataaatgg acagtacagc    3360
ctatagtgct gccagaaaag gacagctgga ctgtcaatga catacagaaa ttagtgggaa    3420
aattgaattg ggcaagtcag atttatgcag ggattaaagt aaggcaatta tgtaaacttc    3480
ttaggggaac caaagcacta acagaagtag taccactaac agaagaagca gagctagaac    3540
tggcagaaaa cagggagatt ctaaaagaac cggtacatgg agtgtattat gacccatcaa    3600
aagacttaat agcagaaata cagaagcagg ggcaaggcca atggacatat caaatttatc    3660
aagagccatt taaaaatctg aaaacaggaa aatatgcaag aatgaagggt gcccacacta    3720
atgatgtgaa acaattaaca gaggcagtac aaaaaatagc cacagaaagc atagtaatat    3780
ggggaaagac tcctaaattt aaattaccca tacaaaagga acatgggaa gcatggtgga    3840 cagagtattg gcaagccacc tggattcctg agtgggagtt tgtcaatacc cctcccttag    3900
tgaagttatg gtaccagtta gagaaagaac ccataatagg agcagaaact ttctatgtag    3960
atggggcagc caatagggaa actaaattag gaaaagcagg atatgtaact gacagaggaa    4020
gacaaaaagt tgtcccccta acggacacaa caaatcagaa gactgagtta caagcaattc    4080
atctagcttt gcaggattcg ggattagaag taaacatagt gacagactca caatatgcat    4140
tgggaatcat tcaagcacaa ccagataaga gtgaatcaga gttagtcagt caaataatag    4200
agcagttaat aanaaaagga aaagtctac ctggcatggg taccagcaca caaggaatt      4260 ggaggaaatg aacagtagat aaattggtca gtgctggaat caggaaagta ctattttag    4320
```

```
atggaataga taaggcccaa gaagaacatg agaaatatca cagtaattgg agagcaatgg    4380
ctagtgattt taacctacca cctgtagtag caaaagaaat agtagccagc tgtgataaat    4440
gtcagctaaa aggggaagcc atgcatggac aagtagactg tagcccagga atatggcagc    4500
tagattgtac acatttagaa ggaaaagtta tcttggtagc agttcatgta gccagtggat    4560
atatagaagc agaagtaatt ccagcagaga cagggcaaga aacagcatac ttcctcttaa    4620
aattagcagg aagatggcca gtaaaaacag tacatacaga caatggcagc aatttcacca    4680
gtactacagt taaggccgcc tgttggtggg cggggatcag caggaatttg gcattcccta    4740
caatccccaa agtcaaggag taatagaatc tatgaataaa gaattaaaga aaattatagg    4800
acaggtaaga gatcaggctg aacatcttaa gacagcagta caaatggcag tattcatcca    4860
caattttaaa agaaaagggg ggattggggg gtacagtgca ggggaaagaa tagtagacat    4920
aatagcaaca gacatacaaa ctaaagaatt acaaaaacaa attacaaaaa ttcaaaattt    4980
tcgggtttat tacagggaca gcagagatcc agtttggaaa ggaccagcaa agctcctctg    5040
gaaaggtgaa ggggcagtag taatacaaga taatagtgac ataaaagtag tgccaagaag    5100
aaaagcaaag atcatcaggg attatggaaa acagatggca ggtgatgatt gtgtggcaag    5160
tagacaggat gaggattaac acatggaatt ctgcaacaac tgctgtttat ccatttcaga    5220
attgggtgtc gacatagcag aataggcgtt actcgacaga ggagagcaag aaatggagcc    5280
agtagatcct agactagagc cctggaagca tccaggaagt cagcctaaaa ctgcttgtac    5340
caattgctat tgtaaaaagt gttgctttca ttgccaagtt tgtttcatga caaaagcctt    5400
aggcatctcc tatggcagga agaagcggag acagcgacga agagctcatc agaacagtca    5460
gactcatcaa gcttctctat caaagcagta agtagtacat gtaatgcaac ctataatagt    5520
agcaatagta gcattagtag tagcaataat aatagcaata gttgtgtggt ccatagtaat    5580
catagaatat aggaaaatgg ccgctgatct tcagacctgg aggaggagat atgagggaca    5640
attggagaag tgaattatat aaatataaag tagtaaaaat tgaaccatta ggagtagcac    5700
ccaccaaggc aaagaagaa gtggtgcaga gagaaaaaag agcagtggga ataggagctt    5760
tgttccttgg gttcttggga gcagcaggaa gcactatggg cgcagcgtca atgacgctga    5820
cggtacaggc cagacaatta ttgtctggtn tagtgcagca gcagaacaat ttgctgaggg    5880
ctattgaggc gcaacagcat ctgttgcaac tcacagtctg gggcatcaag cagctccagg    5940
caagaatcct ggctgtggaa agatacctaa aggatcaaca gctcctgggg atttggggtt    6000
gctctggaaa actcatttgc accactgctg tgccttggaa tgctagttgg agtaataaat    6060
ctctggaaca gatttggaat cacacgacct ggatggagtg ggacagagaa attaacaatt    6120
acacaagctt aatacactcc ttaattgaag aatcgcaaaa ccagcaagaa aagaatgaac    6180
aagaattatt ggaattagat gaatgggcaa gtttgtggaa ttggtttaac ataacaaatt    6240
ggctgtggta tataaaatta ttcataatga tagtaggagg cttggtaggt ttaagaatag    6300
tttttgctgt actttctata gtgaatagag ttaggcaggg atattcacca ttatcgtttc    6360
agacccacct cccaacccg aggggacccg acaggcccga aggaatagaa gaagaaggtg    6420
gagagagaga cagagacaga tccattcgat tagtgaacgg atccttggca cttatctggg    6480
acgatctgcg gagcctgtgc ctcttcagct accaccgctt gagagactta ctcttgattg    6540
taacgaggat tgtggaactt ctgggacgca ggggtggga agccctcaaa tattggtgga    6600
atctcctaca atattggagt caggagctaa agaatagtgc tgttagcttg ctcaatgcca    6660
cagccatagc agtagctgag gggacagata gggttataga agtagtacaa ggagcttgta    6720
```

```
gagctattcg ccacatacct agaagaataa gacagggctt ggaaaggatt ttgctataag    6780
ctcgaggccg ccccggtgac cttcagacct tggcactgga ggtggcccgg cagaagcgcg    6840
gcatcgtgga tcagtgctgc accagcatct gctctctcta ccaactggag aactactgca    6900
actaggccca ccactaccct gtccaccccT ctgcaatgaa taaaaccttt gaaagagcac    6960
tacaagttgt gtgtacatgc gtgcatgtgc atatgtggtg cgggggggaac atgagtgggg    7020
ctggctggag tggcgatgat aagctgtcaa acatgagaat taattcttga agacgaaagg    7080
gcctcgtgat acgcctattt ttataggtta atgtcatgat aataatggtt tcttagtcta    7140
gaattaattc cgtgtattct atagtgncac ctaaatcgta tgtgtatgat acataaggtt    7200
atgtattaat tgtagccgcg ttctaacgac aatatgtaca agcctaattg tgtagcatct    7260
ggcttactga agcagaccct atcatctctc tcgtaaactg ccgtcagagt cggtttggtt    7320
ggacgaacct tctgagtttc tggtaacgcc gtcccgcacc cgcacccggn aaatggtcag    7380
cgaaccaatc agcagggtca tcgctagcca gatcctctac gccggacgca tcgtggccgg    7440
catcaccggc gccacaggtg cggttgcatg gcgcctatat cgccgacatc accgatgggg    7500
aagatcgggc tcgccacttc gggctcatga gcgcttgttt cggcgtgggt atggtggcag    7560
gccccgtggc cgggggactg ttgggcgcca tctccttgca tgcaccattc cttgcggcgg    7620
cggtgctcaa cggcctcaac ctactactgg gctgcttcct aatgcaggag tcgcataagg    7680
gagagcgtcg aatggtgcac tctcagtaca atctgctctg atgccgcata gttaagccag    7740
ccccgacacc cgccaacacc cgctgacgcg ccctgacggg cttgtctgct cccggcatcc    7800
gcttacagac aagctgtgac cgtctccggg agctgcatgt gtcagaggtn ntcaccgtca    7860
tcaccgaaac gcgcgagacg aaagggcctc gtgatacgcc tattttTata ggttaatgtc    7920
atgataataa tggtttctta gacgtcaggt ggcactttTc ggggaaatgt gcgcggaacc    7980
cctatttgtt tattttTcta aatacattca aatatgtatc cgctcatgag acaataaccc    8040
tgataaatgc ttcaataata ttgaaaaagg aagagtatga gtattcaaca tttccgtgtc    8100
gcccttattc cctttttTgc ggcatttTgc cttcctgtTt ttgctcaccc agaaacgctg    8160
gtgaaagtaa aagatgctga agatcagttg ggtgcacgag tgggttacat cgaactggat    8220
ctcaacagcg gtaagatcct tgagagtttT cgccccgaag aacgttttcc aatgatgagc    8280
acttTtaaag ttctgctatg tggcgcggta ttatcccgta ttgacgccgg caagagcaa    8340
ctcggtcgcc gcatacacta ttctcagaat gacttggttg agtactcacc agtcacagaa    8400
aagcatctta cggatggcat gacagtaaga gaattatgca gtgctgccat aaccatgagt    8460
gataacactg cggccaactt acttctgaca acgatcggag gaccgaagga gctaaccgct    8520
ttTttgcaca acatggggga tcatgtaact cgccttgatc gttgggaacc ggagctgaat    8580
gaagccatac caaacgacga gcgtgacacc acgatgcctg tagcaatggc aacaacgttg    8640
cgcaaactat taactggcga actacttact ctagcttccc ggcaacaatt aatagactgg    8700
atggaggcgg ataaagttgc aggaccactt ctgcgctcgg cccttccggc tggctggTtt    8760
attgctgata atctggagc cggtgagcgt gggtctcgcg gtatcattgc agcactgggg    8820
ccagatggta agccctcccg tatcgtagtt atctacacga cggggagtca ggcaactatg    8880
gatgaacgaa atagacagat cgctgagata ggtgcctcac tgattaagca ttggtaactg    8940
tcagaccaag tTtactcata tatactttag attgatttaa aacttcattt ttaattTaaa    9000
aggatctagg tgaagatcct tTttgataat ctcatgacca aaatccctta acgtgagttt    9060
tcgttccact gagcgtcaga ccccgtagaa aagatcaaag gatcttcttg agatccttTt    9120
```

```
tttctgcgcg taatctgctg cttgcaaaca aaaaaaccac cgctaccagc ggtggtttgt   9180
ttgccggatc aagagctacc aactcttttt ccgaaggtaa ctggcttcag cagagcgcag   9240
ataccaaata ctgtccttct agtgtagccg tagttaggcc accacttcaa gaactctgta   9300
gcaccgccta catacctcgc tctgctaatc ctgttaccag tggctgctgc cagtggcgat   9360
aagtcgtgtc ttaccgggtt ggactcaaga cgatagttac cggataaggc gcagcggtcg   9420
ggctgaacgg ggggttcgtg cacacagccc agcttggagc gaacgaccta caccgaactg   9480
agatacctac agcgtgagca ttgagaaagc gccacgcttc ccgaagggag aaaggcggac   9540
aggtatccgg taagcggcag ggtcggaaca ggagagcgca cgagggagct tccaggggga   9600
aacgcctggt atctttatag tcctgtcggg tttcgccacc tctgacttga gcgtcgattt   9660
ttgtgatgct cgtcaggggg gcggagccta tggaaaaacg ccagcaacgc ggcctttttta   9720
cggttcctgg ccttttgctg gccttttgct cacatgttct ttcctgcgtt atcccctgat   9780
tctgtggata accgtattac cgcctttgag tgagctgata ccgctcgccg cagccgaacg   9840
accgagcgca gcgagtcagt gagcgaggaa gcggaagagc gcccaatacg caaaccgcct   9900
ctccccgcgc gttggccgat tcattaatgc agctgtggaa tgtgtgtcag ttagggtgtg   9960
gaaagtcccc aggctcccca gcaggcagaa gtatgcaaag catgcatctc aattagtcag  10020
caaccaggtg tggaaagtcc ccaggctccc cagcaggcag aagtatgcaa agcatgcatc  10080
tcaattagtc agcaaccata gtcccgcccc taactccgcc catcccgccc ctaactccgc  10140
ccagttccgc ccattctccg ccccatggct gactaatttt ttttatttat gcagaggccg  10200
aggccgcctc ggcctctgag ctattccaga agtagtgagg aggcttttttt ggaggcctag  10260
gcttttgcaa aaagcttgga cacaagacag gcttgcgaga tatgtttgag aataccactt  10320
tatcccgcgt cagggagagg cagtgcgtaa aaagacgcgg actcatgtga aatactggtt  10380
tttagtgcgc cagatctcta taatctcgcg caacctattt tcccctcgaa cacttttta  10440
gccgtagata acaggctgg gacacttcac atgagcgaaa aatacatcgt cacctgggac  10500
atgttgcaga tccatgcacg taaactcgca agccgactga tgccttctga caatggaaaa  10560
ggcattattg ccgtaagccg tggcggtctg taccgggtgc gttactggcg cgtgaactgg  10620
gtattcgtca tgtcgatacc gtttgtattt ccagctacga tcacgacaac cagcgcgagc  10680
ttaaagtgct gaaacgcgca gaaggcgatg gcgaaggctt catcgttatt gatgacctgg  10740
tggataccgg tggtactgcg gttgcgattc gtgaaatgta ccaaaagcg cactttgtca  10800
ccatcttcgc aaaaccggct ggtcgtccgc tggttgatga ctatgttgtt gatatcccgc  10860
aagatacctg gattgaacag ccgtgggata tgggcgtcgt attcgtcccg ccaatctccg  10920
gtcgctaatc ttttcaacgc ctggcactgc cgggcgttgt tctttttaac ttcaggcggg  10980
ttacaatagt ttccagtaag tattctggag gctgcatcca tgacacaggc aaacctgagc  11040
gaaaccctgt tcaaaccccg ctttaaacat cctgaaacct cgacgctagt ccgccgcttt  11100
aatcacggcg cacaaccgcc tgtgcagtcg gcccttgatg gtaaaaccat ccctcactgg  11160
tatcgcatga ttaaccgtct gatgtggatc tggcgcggca ttgacccacg cgaaatcctc  11220
gacgtccagg cacgtattgt gatgagcgat gccgaacgta ccgacgatga tttatacgat  11280
acggtgattg gctaccgtgg cggcaactgg atttatgagt gggcccccga tctttgtgaa  11340
ggaaccttac ttctgtggtg tgacataatt ggacaaacta cctacagaga tttaaagctc  11400
taaggtaaat ataaaatttt taagtgtata atgtgttaaa ctactgattc taattgtttg  11460
tgtatttag attccaacct atggaactga tgaatgggag cagtggtgga atgcctttaa  11520
```

```
tgaggaaaac ctgttttgct cagaagaaat gccatctagt gatgatgagg ctactgctga    11580
ctctcaacat tctactcctc caaaaagaa gagaaggta gaagacccca aggactttcc      11640
ttcagaattg ctaagttttt tgagtcatgc tgtgtttagt aatagaactc ttgcttgctt    11700
tgctatttac accacaaagg aaaagctgc actgctatac aagaaaatta tggaaaaata     11760
ttctgtaacc tttataagta ggcataacag ttataatcat aacatactgt tttttcttac    11820
tccacacagg catagagtgt ctgctattaa taactatgct caaaaattgt gtacctttag    11880 cttttttaatt tgtaaagggg ttaataagga atatttgatg tatagtgcct tgactagaga   11940
tcataatcag ccataccaca tttgtagagg ttttacttgc tttaaaaaac ctccccacac    12000 ctcccccctga acctgaaaca taaaatgaat gcaattgttg ttgttgggct gcagtatgaa   12060
t                                                                   12061
```

<210> SEQ ID NO 21
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgtccgcag caccactggt cacggcaatg tgtttgctcg gaatgtgag cttcccatgc      60 gaccgcccgc ccacatgcta tacccgcgaa ccttccagag ccctcgacat ccttgaagag    120
aacgtgaacc atgaggccta cgataccctg ctcaatgcca tattgcggtg cggatcgtct    180
ggcagaagca aaga                                                      195
```

<210> SEQ ID NO 22
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
agcgtcactg acgactttac cctgaccagc ccctacttgg gcacatgctc gtactgccac      60
catactgaac cgtgcttcag ccctgttaag atcgagcagg tctgggacga agcggacgat    120
aacaccatac gcatacagac ttccgcccag tttggatacg accatagcgg agcagcaagc    180
gcaaacaagt accgctacat gtcgcttaag caggtaacca acgtagacaa caaattcaac    240
aaagaacaac aaaacgcgtt ctatgagatc ttacatttac ctaacttaaa cgaagaacaa    300
cgaaacgcct tcatccaaag tttaaaagat gacccaagcc aaagcgctaa ccttttagca    360
gaagctaaaa agctaaatga tgctcaggcg ccgaaagtag acaacaaatt caacaaagaa    420
caacaaaacg cgttctatga gatcttacat ttacctaact taaacgaaga caacgaaac    480 gccttcatcc aaagtttaaa agatgaccca agcaaagcg ctaaccttttt agcagaagct    540 aaaaagctaa atgatgctca ggcgccgaaa gtagacgcga attcgagctc ggtacccgta    600
accaccgtta agaaggcac catggatgac atcaagatta gcacctcagg accgtgtaga    660
aggcttagct acaaaggata ctttctcctc gcaaaatgcc ctccagggga cagcgtaacg    720
gttagcatag tgagtagcaa ctcagcaacg tcatgtacac tggcccgcaa gataaaacca    780
aaattcgtgg gacgggaaaa atatgatcta cctcccgttc acgtaaaaaa aattccttgc    840
acagtgtacg accgtctgaa agaaacaact gcaggctaca tcactatgca caggccggga    900
```

```
ccgcacgctt atacatccta cctggaagaa tcatcaggga aagtttacgc aaagccgcca    960
tctgggaaga acattacgta tgagtgcaag tgcggcgact acaagaccgg aaccgtttcg   1020
acccgcaccg aaatcactgg ttgcaccgcc atcaagcagt gcgtcgccta taagagcgac   1080
caaacgaagt gggtcttcaa ctcaccggac ttgatcagac atgacgacca cacggcccaa   1140
gggaaattgc atttgccttt caagttgatc ccgagtacct gcatggtccc tgttgcccac   1200
gcgccgaatg taatacatgg ctttaaacac atcagcctcc aattagatac agaccacttg   1260
acattgctca ccaccaggag actagggca aaccccggaac caaccactga atggatcgtc   1320
ggaaagacgg tcagaaactt caccgtcgac cgagatggcc tggaatacat atggggaaat   1380
catgagccag tgagggtcta tgcccaagag tcagcaccag agaccctca cggatggcca   1440 cacgaaatag tacagcatta ctaccatcgc catcctgtgt acaccatctt agccgtcgca   1500
tcagctaccg tggcgatgat gattggcgta actgttgcag tgttatgtgc ctgtaaagcg   1560
cgccgtgagt gcctgacgcc atacgccctg gccccaaacg ccgtaatccc aacttcgctg   1620
gcactcttgt gctgcgttag gtcggccaat gct                                1653
```

```
<210> SEQ ID NO 23
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gaaacgttca ccgagaccat gagttacttg tggtcgaaca gtcagccgtt cttctgggtc     60
cagttgtgca tacctttggc cgctttcatc gttctaatgc gctgctgctc ctgctgcctg    120
ccttttttag tggttgccgg cgcctacctg gcgaaggtag acgcc                    165
```

```
<210> SEQ ID NO 24
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tacgaacatg cgaccactgt tccaaatgtg ccacagatac cgtataaggc acttgttgaa     60
agggcagggt atgccccgct caatttggag atcactgtca tgtcctcgga ggttttgcct    120
tccaccaacc aagagtacat tacctgcaaa ttcaccactg tggtccccct cccaaaaatc    180
aaatgctgcg gctccttgga atgtcagccg gccgctcatg cagactatac ctgcaaggtc    240
ttcggagggg tctaccctt tatgtgggga ggagcgcaat gttttgcga cagtgagaac    300 agccagatga gtgaggcgta cgtcgaattg tcagcagatt gcgcgtctga ccacgcgcag    360
gcgattaagg tgcacactgc cgcgatgaaa gtaggactgc gtatagtgta cgggaacact    420
accagtttcc tagatgtgta cgtgaacgga gtcacaccag gaacgtctaa agacttgaaa    480
gtcatagctg gaccaatttc agcatcattt acgccattcg atcataaggt cgttatccat    540
cgcggcctgg tgtacaacta tgacttcccg gaatatggag cgatgaaacc aggagcgttt    600
ggagacattc aagctaccct cttgactagc aaggatctca tcgccagcac agacattagg    660
ctactcaagc cttccgccaa gaatgtgcat gtcccgtaca cgcaggccgc atcaggattt    720
gagatgtgga aaaacaactc aggccgccca ttgcaggaaa ccgcacctt cgggtgtaag    780
```

| | |
|---|---|
| attgcagtaa atccgctccg agcggtggac tgttcatacg ggaacattcc catttctatt | 840 |
| gacatcccga acgctgcctt tatcaggaca tcagatgcac cactggtctc aacagtcaaa | 900 |
| tgtgaagtca gtgagtgcac ttattcagca gacttcgacg ggatggccac cctgcagtat | 960 |
| gtatccgacc gcgaaggtca atgccccgta cattcgcatt cgagcacagc aactctccaa | 1020 |
| gagtcgacag tacatgtcct ggagaaagga gcggtgacag tacactttag caccgcgagt | 1080 |
| ccacaggcga actttatcgt atcgctgtgt gggaagaaga caacatgcaa tgcagaatgt | 1140 |
| aaaccaccag ctgaccatat cgtgagcacc ccgcacaaaa atgaccaaga atttcaagcc | 1200 |
| gccatctcaa aaacatcatg gagttggctg tttgcccttt tcggcggcgc ctcgtcgcta | 1260 |
| ttaattatag gacttatgat ttttgcttgc agcatgatgc tgactagcac acgaagatga | 1320 |

<210> SEQ ID NO 25
<211> LENGTH: 6612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

| | |
|---|---|
| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattccctt tttgcggcat | 180 |
| tttgccttcc tgttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |
| agaatgactt ggttgagtac tcaccagtca cagaaaagca tcttacggat ggcatgacag | 480 |
| taagagaatt atgcagtgct gccataacca tgagtgataa cactgcggcc aacttacttc | 540 |
| tgacaacgat cggaggaccg aaggagctaa ccgcttttt gcacaacatg ggggatcatg | 600 |
| taactcgcct tgatcgttgg gaaccggagc tgaatgaagc cataccaaac gacgagcgtg | 660 |
| acaccacgat gcctgtagca atggcaacaa cgttgcgcaa actattaact ggcgaactac | 720 |
| ttactctagc ttcccggcaa caattaatag actggatgga ggcggataaa gttgcaggac | 780 |
| cacttctgcg ctcggccctt ccggctggct ggtttattgc tgataaatct ggagccggtg | 840 |
| agcgtgggtc tcgcggtatc attgcagcac tggggccaga tggtaagccc tcccgtatcg | 900 |
| tagttatcta cacgacgggg agtcaggcaa ctatggatga acgaaataga cagatcgctg | 960 |
| agataggtgc ctcactgatt aagcattggt aactgtcaga ccaagtttac tcatatatac | 1020 |
| tttagattga tttaaaactt catttttaat ttaaaaggat ctaggtgaag atccttttg | 1080 |
| ataatctcat gaccaaaatc ccttaacgtg agttttcgtt ccactgagcg tcagaccccg | 1140 |
| tagaaaagat caaaggatct tcttgagatc cttttttct gcgcgtaatc tgctgcttgc | 1200 |
| aaacaaaaaa accaccgcta ccagcggtgg tttgtttgcc ggatcaagag ctaccaactc | 1260 |
| tttttccgaa ggtaactggc ttcagcagag cgcagatacc aaatactgtc cttctagtgt | 1320 |
| agccgtagtt aggccaccac ttcaagaact ctgtagcacc gcctacatac ctcgctctgc | 1380 |
| taatcctgtt accagtggct gctgccagtg gcgataagtc gtgtcttacc gggttggact | 1440 |
| caagacgata gttaccggat aaggcgcagc ggtcgggctg aacggggggt tcgtgcacac | 1500 |

```
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gattttgtg atgctcgtca gggggcgga     1740 gcctatggaa aaacgccagc aacgcggcct ttttacggtt cctggccttt gctggcctt    1800 ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga gagcgcccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg gactttcct acttggcagt    2640 acatctacgt attagtcatc gctattacca tggtgatgcg gttttggcag tacatcaatg   2700
ggcgtggata gcggtttgac tcacggggat ttccaagtct ccacccatt gacgtcaatg     2760 ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga ccctttagt cagtgtggaa     3060 aatctctagc agtggcgccc gaacaggac ctgaaagcga aagggaaacc agaggagctc      3120
tctcgacgca ggactcggct tgctgaagcg cgcacggcaa gaggcgaggg gcggcgactg   3180
gtgagtacgc caaaattttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata agtagtaaa    3660 aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcc tcaatgacgc tgacggtaca ggccagacaa ttattgtctg gtatagtgca   3840
gcagcagaac aatttgctga gggctattga ggcgcaacag catctgttgc aactcacagt   3900
```

```
ctggggcatc aagcagctcc aggcaagaat cctggctgtg gaaagatacc taaaggatca    3960
acagctcctg gggatttggg gttgctctgg aaaactcatt tgcaccactg ctgtgccttg    4020
gaatgctagt tggagtaata aatctctgga acagattgga atcacacgac ctggatggag    4080
tgggacagag aaattaacaa ttacacaagc ttaatacact ccttaattga agaatcgcaa    4140
aaccagcaag aaaagaatga acaagaatta ttggaattag ataaatgggc aagtttgtgg    4200
aattggttta acataacaaa ttggctgtgg tatataaaat tattcataat gatagtagga    4260
ggcttggtag gtttaagaat agttttttgct gtacttttcta tagtgaatag agttaggcag    4320
ggatattcac cattatcgtt tcagacccac ctcccaaccc cgaggggacc cgacaggccc    4380
gaaggaatag aagaagaagg tggagagaga gacagagaca gatccattcg attagtgaac    4440
ggatctcgac ggtatcgata agctaattca caaatggcag tattcatcca caattttaaa    4500
agaaaagggg ggattggggg gtacagtgca ggggaaagaa tagtagacat aatagcaaca    4560
gacatacaaa ctaaagaatt acaaaaacaa attacaaaaa ttcaaaattt tcgggtttat    4620
tacagggaca gcagagatcc agtttgggaa ttagcttgat cgattagtcc aatttgttaa    4680
agacaggata tcagtggtcc aggctctagt tttgactcaa caatatcacc agctgaagcc    4740
tatagagtac gagccataga tagaataaaa gattttattt agtctccaga aaaggggggg    4800
aatgaaagac cccaccctgta ggtttggcaa gctaggatca aggttaggaa cagagagaca    4860
gcagaatatg ggccaaacag gatatctgtg gtaagcagtt cctgccccgg ctcagggcca    4920
agaacagttg gaacagcaga atatgggcca aacaggatat ctgtggtaag cagttcctgc    4980
cccggctcag ggccaagaac agatggtccc cagatgcggt cccgccctca gcagtttcta    5040
gagaaccatc agatgtttcc agggtgcccc aaggacctga aatgaccctg tgccttattt    5100
gaactaacca atcagttcgc ttctcgcttc tgttcgcgcg cttctgctcc ccgagctcaa    5160
taaaagagcc cacaacccct cactcggcgc gatctagatc tcgaatcgaa ttcgttaacc    5220
tcgagggatc ccccggggtc gactgatcaa attcgagctc ggtacctttta agaccaatga    5280 cttacaaggc agctgtagat cttagccact ttttaaaaga aaaggggggga ctggaagggc    5340 taattcactc ccaacgaaga caagatctgc tttttgcttg tactgggtct ctctggttag    5400
accagatctg agcctgggag ctctctggct aactagggaa cccactgctt aagcctcaat    5460 aaaagcttgcc ttgagtgctt caagtagtgt gtgcccgtct gttgtgtgac tctggtaact    5520
agagatccct cagacccttt tagtcagtgt ggaaaatctc tagcagtagt agttcatgtc    5580
atcttattat tcagtattta aacttgcaa agaaatgaat atcagagagt gagaggaact    5640
tgtttattgc agcttataat ggttacaaat aaagcaatag catcacaaat ttcacaaata    5700
aagcattttt ttcactgcat tctagttgtg gtttgtccaa actcatcaat gtatcttatc    5760
atgtctggct ctagctatcc cgccctaac tccgcccatc ccgcccctaa ctccgcccag    5820
ttccgcccat tctccgcccc atggctgact aattttttttt atttatgcag aggccgaggc    5880
cgcctcggcc tctgagctat tccagaagta gtgaggaggc ttttttggag gcctaggctt    5940
ttgcgtcgag acgtacccaa ttcgccctat agtgagtcgt attacgcgcg ctcactggcc    6000
gtcgttttac aacgtcgtga ctgggaaaac cctggcgtta cccaacttaa tcgccttgca    6060
gcacatcccc ctttcgccag ctggcgtaat agcgaagagg cccgcaccga tcgcccttcc    6120
caacagttgc gcagcctgaa tggcgaatgg cgcgacgcgc cctgtagcgg cgcattaagc    6180
gcggcgggtg tggtggttac gcgcagcgtg accgctacac ttgccagcgc cctagcgccc    6240
gctcctttcg ctttcttccc ttcctttctc gccacgttcg ccggctttcc ccgtcaagct    6300
```

```
ctaaatcggg ggctcccttt agggttccga tttagtgctt tacggcacct cgaccccaaa    6360
aaacttgatt agggtgatgg ttcacgtagt gggccatcgc cctgatagac ggttttttcgc   6420 cctttgacgt tggagtccac gttctttaat agtggactct tgttccaaac tggaacaaca    6480
ctcaacccta tctcggtcta ttcttttgat ttataaggga ttttgccgat ttcggcctat    6540
tggttaaaaa atgagctgat ttaacaaaaa tttaacgcga atttaacaa aatattaacg     6600 tttacaattt cc                                                       6612

<210> SEQ ID NO 26
<211> LENGTH: 9061
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
catggccaag ttgaccagtg ccgttccggt gctcaccgcg cgcgacgtcg ccggagcggt      60
cgagttctgg accgaccggc tcggttctc ccgggacttc gtggaggacg acttcgccgg     120
tgtggtccgg gacgacgtga ccctgttcat cagcgcggtc caggaccagg tggtgccgga    180
caacaccctg gcctgggtgt gggtgcgcgg cctggacgag ctgtacgccg agtggtcgga    240
ggtcgtgtcc acgaacttcc gggacgcctc cgggccggcc atgaccgaga tcggcgagca    300
gccgtggggg cgggagttcg ccctgcgcga cccggccggc aactgcgtgc acttcgtggc    360
cgaggagcag gactgacacg tgctacgaga tttcgattcc accgccgcct tctatgaaag    420
gttgggcttc ggaatcgttt tccgggacgc cggctggatg atcctccagc gcgggatct     480 catgctggag ttcttcgccc accccaactt gtttattgca gcttataatg ttacaaata     540 aagcaatagc atcacaaatt tcacaaataa agcatttttt tcactgcatt ctagttgtgg    600
tttgtccaaa ctcatcaatg tatcttatca tgtctgtata ccgtcgacct ctagctagag    660
cttggcgtaa tcatggtcat agctgtttcc tgtgtgaaat tgttatccgc tcacaattcc    720
acacaacata cgagccggaa gcataaagtg taaagcctgg ggtgcctaat gagtgagcta    780
actcacatta attgcgttgc gctcactgcc cgctttccag tcgggaaacc tgtcgtgcca    840
gctgcattaa tgaatcggcc aacgcgcggg gagaggcggt ttgcgtattg ggcgctcttc    900
cgcttcctcg ctcactgact cgctgcgctc ggtcgttcgg ctgcggcgag cggtatcagc    960
tcactcaaag gcggtaatac ggttatccac agaatcaggg gataacgcag gaaagaacat   1020
gtgagcaaaa ggccagcaaa aggccaggaa ccgtaaaaag gccgcgttgc tggcgttttt   1080
ccataggctc cgcccccctg acgagcatca caaaaatcga cgctcaagtc agaggtggcg   1140
aaacccgaca ggactataaa gataccaggc gtttccccct ggaagctccc tcgtgcgctc   1200
tcctgttccg accctgccgc ttaccggata cctgtccgcc tttctccctt cgggaagcgt   1260
ggcgctttct caatgctcac gctgtaggta tctcagttcg gtgtaggtcg ttcgctccaa   1320
gctgggctgt gtgcacgaac cccccgttca gcccgaccgc tgcgccttat ccggtaacta   1380
tcgtcttgag tccaacccgg taagacacga cttatcgcca ctggcagcag ccactggtaa   1440
caggattagc agagcgaggt atgtaggcgg tgctacagag ttcttgaagt ggtggcctaa   1500
ctacggctac actagaagga cagtatttgg tatctgcgct ctgctgaagc cagttacctt   1560
cggaaaaaga gttggtagct cttgatccgg caaacaaacc accgctggta gcggtggttt   1620
ttttgtttgc aagcagcaga ttacgcgcag aaaaaaagga tctcaagaag atcctttgat   1680
cttttctacg gggtctgacg ctcagtggaa cgaaaactca cgttaaggga ttttggtcat   1740
```

```
gagattatca aaaaggatct tcacctagat cctttaaat taaaaatgaa gttttaaatc   1800
aatctaaagt atatatgagt aaacttggtc tgacagttac caatgcttaa tcagtgaggc   1860
acctatctca gcgatctgtc tatttcgttc atccatagtt gcctgactcc ccgtcgtgta   1920
gataactacg atacgggagg gcttaccatc tggccccagt gctgcaatga taccgcgaga   1980
cccacgctca ccggctccag atttatcagc aataaaccag ccagccggaa gggccgagcg   2040
cagaagtggt cctgcaactt tatccgcctc catccagtct attaattgtt gccgggaagc   2100
tagagtaagt agttcgccag ttaatagttt gcgcaacgtt gttgccattg ctacaggcat   2160
cgtggtgtca cgctcgtcgt ttggtatggc ttcattcagc tccggttccc aacgatcaag   2220
gcgagttaca tgatccccca tgttgtgcaa aaagcggtt agctccttcg gtcctccgat    2280
cgttgtcaga agtaagttgg ccgcagtgtt atcactcatg gttatggcag cactgcataa   2340
ttctcttact gtcatgccat ccgtaagatg cttttctgtg actggtgagt actcaaccaa   2400
gtcattctga aatagtgta tgcggcgacc gagttgctct tgcccggcgt caatacggga    2460
taataccgcg ccacatagca gaactttaaa agtgctcatc attggaaaac gttcttcggg   2520
gcgaaaactc tcaaggatct taccgctgtt gagatccagt tcgatgtaac ccactcgtgc   2580
acccaactga tcttcagcat cttttacttt caccagcgtt tctgggtgag caaaaacagg   2640
aaggcaaaat gccgcaaaaa agggaataag ggcgacacgg aaatgttgaa tactcatact   2700
cttccttttt caatattatt gaagcattta tcagggttat tgtctcatga gcggatacat   2760
atttgaatgt atttagaaaa ataaacaaat aggggttccg cgcacatttc cccgaaaagt   2820
gccacctgac gtcgacggat cgggagatct cccgatcccc tatggtcgac tctcagtaca   2880
atctgctctg atgccgcata gttaagccag tatctgctcc ctgcttgtgt gttggaggtc   2940
gctgagtagt gcgcgagcaa aatttaagct acaacaaggc aaggcttgac cgacaattgc   3000
atgaagaatc tgcttagggt taggcgtttt gcgctgcttc gcgatgtacg ggccagatat   3060
acgcgttgac attgattatt gactagttat taatagtaat caattacggg gtcattagtt   3120
catagcccat atatggagtt ccgcgttaca taacttacgg taaatggccc gcctggctga   3180
ccgcccaacg acccccgccc attgacgtca ataatgacgt atgttcccat agtaacgcca   3240
atagggactt tccattgacg tcaatgggtg gactatttac ggtaaactgc ccacttggca   3300
gtacatcaag tgtatcatat gccaagtacg cccctattg acgtcaatga cggtaaatgg    3360
cccgcctggc attatgccca gtacatgacc ttatgggact ttcctacttg gcagtacatc   3420
tacgtattag tcatcgctat taccatggtg atgcggtttt ggcagtacat caatgggcgt   3480
ggatagcggt ttgactcacg gggatttcca agtctccacc ccattgacgt caatgggagt   3540
ttgttttggc accaaaatca acgggacttt ccaaaatgtc gtaacaactc cgccccattg   3600
acgcaaatgg gcggtaggcg tgtacggtgg gaggtctata taagcagagc tctctggcta   3660
actagagaac ccactgctta ctggcttatc gaaattaata cgactcacta gggagacc    3720 caagctggct agcgtttaaa cttaagctta tgaatagagg attcttaac atgctcggcc    3780 gccgcccctt cccggccccc actgccatgt ggaggccgcg gagaaggagg caggcggccc   3840
cgatgcctgc ccgcaacggg ctggcttctc aaatccagca actgaccaca gccgtcagtg   3900
ccctagtcat tggacaggca actagacctc aacccccacg tccacgcccg ccaccgcgcc   3960
agaagaagca ggcgcccaag caaccaccga agccgaagaa accaaaaacg caggagaaga   4020
agaagaagca acctgcaaaa cccaaacccg gaaagagaca gcgcatggca cttaagttgg   4080
aggccgacag attgttcgac gtcaagaacg aggacggaga tgtcatcggg cacgcactgg   4140
```

```
ccatggaagg aaaggtaatg aaacctctgc acgtgaaagg aaccatcgac caccctgtgc   4200
tatcaaagct caaatttacc aagtcgtcag catacgacat ggagttcgca cagttgccag   4260
tcaacatgag aagtgaggca ttcacctaca ccagtgaaca ccccgaagga ttctataact   4320
ggcaccacgg agcggtgcag tatagtggag gtagatttac catccctcgc ggagtaggag   4380
gcagaggaga cagcggtcgt ccgatcatgg ataactccgg tcgggttgtc gcgatagtcc   4440
tcggtggagc tgatgaagga acacgaactg ccctttcggt cgtcacctgg aatagtaaag   4500
ggaagacaat taagacgacc ccggaaggga cagaagagtg gtccgcagca ccactggtca   4560
cggcaatgtg tttgctcgga aatgtgagct tcccatgcga ccgcccgccc acatgctata   4620
cccgcgaacc ttccagagcc ctcgacatcc ttgaagagaa cgtgaaccat gaggcctacg   4680
atacccctgct caatgccata ttgcggtgcg gatcgtctgg cagaagcaaa agaagcgtca   4740
ctgacgactt taccctgacc agcccctact tgggcacatg ctcgtactgc caccatactg   4800
aaccgtgctt cagccctgtt aagatcgagc aggtctggga cgaagcggac gataacacca   4860
tacgcataca gacttccgcc cagtttggat acgaccatag cggagcagca agcgcaaaca   4920
agtaccgcta catgtcgctt aagcaggtaa ccgacaacaa attcaacaaa gaacaacaaa   4980
acgcgttcta tgagatctta catttaccta acttaaacga agaacaacga aacgccttca   5040
tccaaagttt aaaagatgac ccaagccaaa gcgctaacct tttagcagaa gctaaaaagc   5100
taaatgatgc tcaggcgccg aaagtagaca acaaattcaa caagaacaa caaaacgcgt   5160
tctatgagat cttacattta cctaacttaa acgaagaaca acgaaacgcc ttcatccaaa   5220
gtttaaaaga tgacccaagc caaagcgcta acctttttagc agaagctaaa aagctaaatg   5280
atgctcaggc gccgaaagta gacgcgaatt cgagctcggt acccggggat ccggtaacca   5340
ccgttaaaga aggcaccatg gatgacatca agattagcac ctcaggaccg tgtagaaggc   5400
ttagctacaa aggatacttt ctcctcgcaa aatgccctcc aggggacagc gtaacggtta   5460
gcatagtgag tagcaactca gcaacgtcat gtacactggc ccgcaagata aaaccaaaat   5520
tcgtgggacg ggaaaaatat gatctacctc ccgttcacgg taaaaaaatt ccttgcacag   5580
tgtacgaccg tctgaaagaa acaactgcag gctacatcac tatgcacagg ccgggaccgc   5640
acgcttatac atcctacctg gaagaatcat cagggaaagt ttacgcaaag ccgccatctg   5700
ggaagaacat tacgtatgag tgcaagtgcg gcgactacaa gaccggaacc gtttcgaccc   5760
gcaccgaaat cactggttgc accgccatca agcagtgcgt cgcctataag agcgaccaaa   5820
cgaagtgggt cttcaactca ccggacttga tcagacatga cgaccacacg gcccaaggga   5880
aattgcattt gcctttcaag ttgatcccga gtacctgcat ggtccctgtt gcccacgcgc   5940
cgaatgtaat acatggcttt aaacacatca gcctccaatt agatacagac cacttgacat   6000
tgctcaccac caggagacta ggggcaaacc cggaaccaac cactgaatgg atcgtcggaa   6060
agacggtcag aaacttcacc gtcgaccgag atggcctgga atacatatgg ggaaatcatg   6120
agccagtgag ggtctatgcc caagagtcag caccaggaga ccctcacgga tggccacacg   6180
aaatagtaca gcattactac catcgccatc ctgtgtacac catcttagcc gtcgcatcag   6240
ctaccgtggc gatgatgatt ggcgtaactg ttgcagtgtt atgtgcctgt aaagcgcgcc   6300
gtgagtgcct gacgccatac gccctggccc caaacgcgcg aatcccaact tcgctggcac   6360
tcttgtgctg cgttaggtcg gccaatgctg aaacgttcac cgagaccatg agttacttgt   6420
ggtcgaacag tcagccgttc ttctgggtcc agttgtgcat acctttggcc gctttcatcg   6480
ttctaatgcg ctgctgctcc tgctgcctgc cttttttagt ggttgccggc gcctacctgg   6540
```

```
cgaaggtaga cgcctacgaa catgcgacca ctgttccaaa tgtgccacag ataccgtata     6600
aggcacttgt tgaaagggca gggtatgccc cgctcaattt ggagatcact gtcatgtcct     6660
cggaggtttt gccttccacc aaccaagagt acattacctg caaattcacc actgtggtcc     6720
cctccccaaa aatcaaatgc tgcggctcct tggaatgtca gccggccgct catgcagact     6780
atacctgcaa ggtcttcgga ggggtctacc cctttatgtg gggaggagcg caatgttttt     6840
gcgacagtga gaacagccag atgagtgagg cgtacgtcga attgtcagca gattgcgcgt     6900
ctgaccacgc gcaggcgatt aaggtgcaca ctgccgcgat gaaagtagga ctgcgtatag     6960
tgtacgggaa cactaccagt ttcctagatg tgtacgtgaa cggagtcaca ccaggaacgt     7020
ctaaagactt gaaagtcata gctgaccaa tttcagcatc atttacgcca ttcgatcata      7080
aggtcgttat ccatcgcggc ctggtgtaca actatgactt cccggaatat ggagcgatga     7140
aaccaggagc gtttggagac attcaagcta cctccttgac tagcaaggat ctcatcgcca     7200
gcacagacat taggctactc aagccttccg ccaagaatgt gcatgtcccg tacacgcagg     7260
ccgcatcagg atttgagatg tggaaaaaca actcaggccg cccattgcag gaaaccgcac     7320
cttcggggtg taagattgca gtaaatccgc tccgagcggt ggactgttca tacgggaaca     7380
ttcccatttc tattgacatc ccgaacgctg cctttatcag gacatcagat gcaccactgg     7440
tctcaacagt caaatgtgaa gtcagtgagt gcacttattc agcagacttc gacgggatgg     7500
ccaccctgca gtatgtatcc gaccgcgaag gtcaatgccc cgtacattcg cattcgagca     7560
cagcaactct ccaagagtcg acagtacatg tcctggagaa aggagcggtg acagtacact     7620
ttagcaccgc gagtccacag gcgaacttta tcgtatcgct gtgtgggaag aagacaacat     7680
gcaatgcaga atgtaaacca ccagctgacc atatcgtgag cacccgcac aaaaatgacc       7740 aagaatttca agccgccatc tcaaaaacat catggagttg gctgtttgcc cttttcggcg     7800
gcgcctcgtc gctattaatt ataggactta tgattttgc ttgcagcatg atgctgacta       7860
gcacacgaag atgacgggcc cgtttaaacc cgctgatcag cctcgactgt gccttctagt     7920
tgccagccat ctgttgtttg cccctccccc gtgccttcct tgaccctgga aggtgccact     7980
cccactgtcc tttcctaata aaatgaggaa attgcatcgc attgtctgag taggtgtcat     8040
tctattctgg ggggtggggt ggggcaggac agcaagggg aggattggga agacaatagc        8100
aggcatgctg gggatgcggt gggctctatg gcttctgagg cggaaagaac cagctggggc     8160
tctagggggt atccccacgc gccctgtagc ggcgcattaa gcgcggcggg tgtggtggtt     8220
acgcgcagcg tgaccgctac acttgccagc gccctagcgc ccgctccttt cgctttcttc     8280
ccttcctttc tcgccacgtt cgccggcttt ccccgtcaag ctctaaatcg ggcatccct       8340 ttagggttcc gatttagtgc tttacggcac ctcgacccca aaaaacttga ttagggtgat     8400
ggttcacgta gtgggccatc gccctgatag acggtttttc gccctttgac gttggagtcc     8460
acgttcttta atagtggact cttgttccaa actggaacaa cactcaaccc tatctcggtc     8520 tattctttg atttataagg gattttgggg atttcggcct attggttaaa aaatgagctg      8580
atttaacaaa aatttaacgc gaattaattc tgtggaatgt gtgtcagtta gggtgtggaa     8640
agtccccagg ctccccaggc aggcagaagt atgcaaagca tgcatctcaa ttagtcagca     8700
accaggtgtg gaaagtcccc aggctcccca gcaggcagaa gtatgcaaag catgcatctc     8760
aattagtcag caaccatagt cccgccccta actccgccca tcccgcccct aactccgccc     8820
agttccgccc attctccgcc ccatggctga ctaattttt ttatttatgc agaggccgag       8880
gccgcctctg cctctgagct attccagaag tagtgaggag gcttttttgg aggcctaggc     8940
```

```
                                                    -continued ttttgcaaaa agctcccggg agcttgtata tccattttcg gatctgatca gcacgtgttg    9000
acaattaatc atcggcatag tatatcggca tagtataata cgacaaggtg aggaactaaa    9060
c                                                                    9061
```